United States Patent [19]

Ackermann et al.

[11] Patent Number: 5,405,854
[45] Date of Patent: Apr. 11, 1995

[54] SULFONAMIDOCARBOXAMIDES

[75] Inventors: Jean Ackermann; David Banner, both of Basel, Switzerland; Klaus Gubernator, Freiburg, Germany; Kurt Hilpert, Hofstetten; Gérard Schmid, Kienberg, both of Switzerland

[73] Assignee: Hoffmann-La Roche Inc., Nutley, N.J.

[21] Appl. No.: 21,919

[22] Filed: Feb. 24, 1993

[30] Foreign Application Priority Data

Mar. 6, 1992 [CH] Switzerland ............................ 728/92
Jan. 21, 1993 [CH] Switzerland ............................ 180/93

[51] Int. Cl.$^6$ .................... A61K 31/445; C07D 211/14
[52] U.S. Cl. .................................. 514/315; 514/331; 546/231; 546/247
[58] Field of Search ................ 546/231, 247; 514/315, 514/331

[56] References Cited

U.S. PATENT DOCUMENTS

| | | | |
|---|---|---|---|
| 4,227,006 | 10/1980 | Okamoto et al. | 560/10 |
| 4,258,192 | 3/1981 | Okamoto et al. | 546/166 |
| 4,879,313 | 11/1989 | Tjoeng et al. | 514/616 |
| 5,037,808 | 8/1991 | Tjoeng et al. | 514/20 |
| 5,053,393 | 10/1991 | Tjoeng et al. | 514/18 |
| 5,260,307 | 11/1993 | Ackermann et al. | 514/323 |

FOREIGN PATENT DOCUMENTS

| | | | |
|---|---|---|---|
| 9179490 | 7/1991 | Australia | 546/247 |
| 468231 | 7/1991 | European Pat. Off. | 546/247 |
| 0502536 | 3/1992 | European Pat. Off. | |

OTHER PUBLICATIONS

Drugs of the Future, 17, 1992, 1087–90.
J. Med. Chem. 33, 1990, 1406–1413, Kato et al.
Biochem. J. 55, 1955, 170–171, Dixon.
J. Heterocycl. Chem. 23, 1986 929–933, Grande et al.
J. Med. Chem. 1980, 23, 1293–1299, vol. 12, Kikumoto et al.
Pharmazie 39, 1984, 226–230, Wagner et al.
Thrombosis and Haemotasis 67, 1992, 56–59, Knabb et al.

*Primary Examiner*—Mary C. Lee
*Assistant Examiner*—Joseph K. McKane
*Attorney, Agent, or Firm*—George M. Gould; George W. Johnston; Robert A. Silverman

[57] ABSTRACT

Sulfonamidocarboxamides of the formula

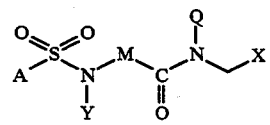

wherein A, M, Q, X and Y have the significance given in the description, as well as hydrates, solvates and salts thereof, which inhibit thrombin-induced blood platelet aggregation and clotting of fibrinogen in plasma, as described. The compounds of formula I can be prepared by amidination of a cyclic amino group standing for grouping X or by C(O)N(Q) amide formation.

36 Claims, No Drawings

SULFONAMIDOCARBOXAMIDES

BRIEF SUMMARY OF THE INVENTION

The invention relates to sulfonamidocarboxamides of the formula

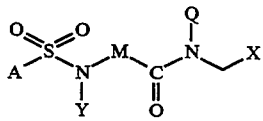

wherein

X is a group of the formula

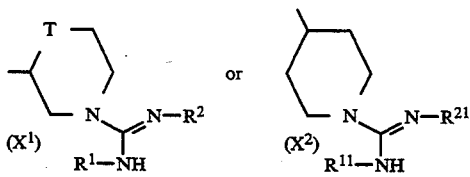

T is $CH_2$ or O, $R^1$, $R^2$, $R^{11}$ and $R^{21}$ are each, independently, hydrogen or —COO-lower-alkyl, Y is hydrogen or, when X is a group $X^2$ or when X is a group $X^1$ in which at least one of $R^1$ and $R^2$ is not hydrogen, then Y can also be —$CH_2COOH$ or —$SO_2$—A', A and A' are aryl, heteroaryl, heterocyclyl, alkyl or cycloalkyl, Q is hydrogen, lower-alkyl or lower-alkyl substituted by OH, —COOH or —COO-lower alkyl, M is a group of the formula $M^1$ or, when X is a group $X^2$ or when X is a group $X^1$ and at least one of $R^1$, $R^2$ and Q is not hydrogen and/or when A is alkyl or cycloalkyl, then M can also be a group of one of the formulae $M^2$ to $M^8$:

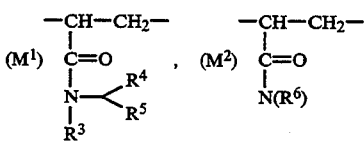

—$CH_2CH(NH(CO)_{1-2}R^7)$ ($M^3$),

—$CH_2CH(NHC(O)O$-benzyl)— ($M^4$),

=$CH(CH_2)_{1-2}R^7$ ($M^5$),

=$CHCH_2C(O)R^8$ ($M^6$),

=$CHCH_2NH(CO)_{1-2}R^7$ ($M^7$)

or

=$CHCH_2NHC(O)O$-benzyl ($M^8$), $R^3$ is hydrogen, lower-alkyl or -alkenyl, aryl, heteroaryl, cycloalkyl, aryl-lower alkyl, heteroaryl-lower alkyl or cycloalkyl-lower alkyl, $R^4$ is hydrogen, lower-alkyl, aryl, cycloalkyl, aryl-lower alkyl or cycloalkyl-lower alkyl, $R^5$ is hydrogen, lower-alkyl or a group $R^{51}$ optionally bonded via lower-alkylene, $R^{51}$ is —COOH, —COO-lower-alkyl, lower-alkanoyl, OH, lower-alkanoyloxy, lower-alkoxy, aryl-lower alkoxy, —$CONH_2$, —$CONHCH_2CH_2OH$, —CONHOH, —$CONHOCH_3$, —CONHO-benzyl, —$CONHSO_2$-lower-alkyl, —$CONHCH_2CH_2$-aryl, —CONH-cycloalkyl, —$CONHCH_2$-heteroaryl, $NH_2$, —NHCOO-lower-alkyl, —NHCOO-lower-aralkyl, —$NHSO_3H$, (—$NHSO_2$ or —$NHSO_3$)-lower-alkyl, —NH-lower-alkanoyl, —NHCOCOOH, —NHCOCOO-lower-alkyl, —NH-cycloalkyl, —NH-(3,4-dioxo-2-hydroxy-cyclobut-1-enyl), —NH-[2-lower-(alkoxy or -alkenyloxy)-3,4-dioxocyclobut-1-enyl], —$NHCH_2$-heteroaryl, —NHCOCO-(aryl or lower-alkyl), —$NHCOCH_2Cl$, —$NHCOCH_2O$-aryl, —$NHCOCH_2$-aryl, —NHCO-aryl, —NHCO— heteroaryl, —$NHPO_3(R_9,R^{10})$, heteroaryl or —$CON(CH_2)_{4-9}$ optionally interrupted by or S and optionally substituted by up to 2 substituents from the group of lower-alkyl, —COOH. —COO-lower alkyl, —$CH_2OH$ and —$CH_2O$-benzyl.

$R^9$ and $R^{10}$ are hydrogen, lower-alkyl or phenyl, provided that $R^4$ can be phenyl, when Q, $R^1$, $R^2$, $R^3$ and $R^5$ are simultaneously hydrogen, $N(R^6)$ is benzylamino or —$N(CH_2)_{4-9}$ optionally interrupted by O or S and optionally ring substituted by up to 2 substituents from the group of lower-alkyl, —COOH, —COO— lower alkyl, —$CH_2OH$ and —$CH_2O$— benzyl, $R^7$ and $R^8$ are aryl, heteroaryl, cycloalkyl or heterocyclyl, or $R^8$ is —$N(CH_2)_{4-9}$ optionally substituted by up to 2 substituents selected from the group consisting of oxo, —COO-lower-alkyl, —$(CH_2)_{0-1}OH$, —$(CH_2)_{0-1}$ OCO-lower-alkyl, —$CONH_2$, —CONH-lower-alkyl or —CON(lower-alkyl)$_2$, as well as hydrates or solvates and physiologically compatible salts thereof.

The compounds of formula I, their solvates and their salts inhibit not only thrombin-induced platelet aggregation, but also thrombin-induced clotting of fibrinogen in blood plasma. The said compounds influence not only platelet-induced, but also plasmatic blood clotting. They, therefore, prevent especially the formation of hyaline thrombin and of platelet-rich thrombin and can be used in the control or prevention of illnesses such as thrombosis, stroke, cardiac infarct, inflammation and arteriosclerosis. Further, these compounds have an effect on tumor cells and prevent the formation of metastases. Accordingly, they can also be used as antitumor agents.

DETAILED DESCRIPTION OF THE INVENTION

The invention relates to sulfonamidocarboxamides of the formula

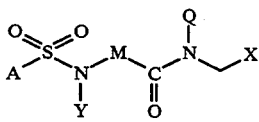

wherein

X is a group of the formula

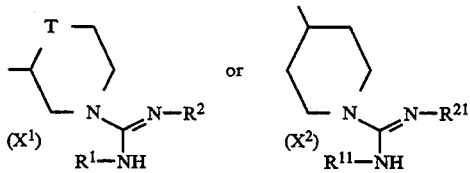

T is CH$_2$ or O,

R$^1$, R$^2$, R$^{11}$ and R$^{21}$ are each, independently, hydrogen or —COO— lower-alkyl, Y is hydrogen or, when X is a group X$^2$ or when X is a group X$^1$ in which at least one of R$^1$ and R$^2$ is not hydrogen, then Y can also be —CH$_2$COOH or —SO$_2$—A', A and A' are aryl, heteroaryl, heterocyclyl, alkyl or cycloalkyl, Q is hydrogen, lower-alkyl or lower-alkyl substituted by OH, —COOH or —COO-lower alkyl, M is a group of the formula M$^1$ or, when X is a group X$^2$ or when X is a group X$^1$ and at least one of R$^1$, R$^2$ and Q is not hydrogen and/or when A is alkyl or cycloalkyl, then M can also be a group of one of the formulae M$^2$ to M$^8$:

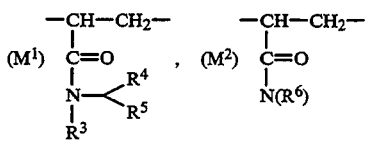

—CH$_2$CH(NH(CO)$_{1-2}$R$^7$)— (M$^3$),

—CH$_2$CH(NHC(O)O-benzyl)— (M$^4$),

=CH(CH$_2$)$_{1-2}$R$^7$ (M$^5$),

=CHCH$_2$C(O)R$^8$ (M$^6$),

=CHCH$_2$NH(CO)$_{1-2}$R$^7$ (M$^7$)

or

=CHCH$_2$NHC(O)O-benzyl (M$^8$),

R$^3$ is hydrogen, lower-alkyl or -alkenyl, aryl, heteroaryl, cycloalkyl, aryl-lower alkyl, heteroaryl-lower alkyl or cycloalkyl-lower alkyl, R$^4$ is hydrogen, lower-alkyl, aryl, cycloalkyl, aryl-lower alkyl or cycloalkyl-lower alkyl, R$^5$ is hydrogen, lower-alkyl or a group R$^{51}$ optionally bonded via lower-alkylene, R$^{51}$ is —COOH, —COO-lower-alkyl, lower-alkanoyl, OH, lower-alkanoyloxy, lower-alkoxy, aryl-lower alkoxy, —CONH$_2$, —CONHCH$_2$CH$_2$OH, —CONHOH, —CONHOCH$_3$, —CONHO-benzyl, —CONHSO$_2$-lower-alkyl, —CONHCH$_2$CH$_2$-aryl, —CONH-cycloalkyl, —CONHCH$_2$-heteroaryl, NH$_2$, —NHCOO-lower-alkyl, —NHCOO-lower-aralkyl, —NHSO$_3$H, (—NHSO$_2$ or —NH-SO$_3$)-lower-alkyl, —NH-lower-alkanoyl, —NH-COCOOH, —NHCOCOO-lower-alkyl, —NH-cycloalkyl, —NH—(3,4-dioxo-2-hydroxy-cyclobut-1-enyl), —NH-[2-lower-(alkoxy or -alkenyloxy)-3,4-dioxocyclobut-1-enyl], —NHCH$_2$-heteroaryl, —NHCOCO-(aryl or lower-alkyl), —NHCOCH$_2$Cl, —NHCOCH$_2$O-aryl, —NH-COCH$_2$-aryl, —NHCO-aryl, —NHCO— heteroaryl, —NHPO$_3$(R$^9$,R$^{10}$), heteroaryl or —CON(CH$_2$)$_{4-9}$ optionally interrupted by O or S and optionally substituted by up to 2 substituents from the group of lower-alkyl, —COOH, —COO-lower alkyl,—CH$_2$OH and —CH$_2$O-benzyl.

R$^9$ and R$^{10}$ are hydrogen, lower-alkyl or phenyl, provided that R$^4$ can not be phenyl, when Q, R$^1$, R$^2$, R$^3$ and R$^5$ are simultaneously hydrogen, N(R$^6$) is benzylamino or —N(CH$_2$)$_{4-9}$ optionally interrupted by O or S and optionally ring substituted by up to 2 substituents from the group of lower-alkyl, HOOC—, —COO— lower alkyl, —CH$_2$OH and —CH$_2$O— benzyl, R$^7$ and R$^8$ are aryl, heteroaryl, cycloalkyl or heterocyclyl, or R$^8$ is —N(CH$_2$)$_{4-9}$ optionally substituted by up to 2 substituents selected from the group consisting of oxo, —COO-lower-alkyl, —(CH$_2$)$_{0-1}$OH, —(CH$_2$)$_{0-1}$ OCO-lower-alkyl, —CONH$_2$, —CONH-lower-alkyl or —CON(lower-alkyl)$_2$, as well as hydrates or solvates and physiologically compatible salts thereof.

Further, the invention is concerned with a process for the preparation of the above compounds, pharmaceutical preparations which contain such compounds as well as the use of these compounds in the manufacture of pharmaceutical preparations.

Examples of physiologically usable salts of the compounds of formula I are salts with physiologically compatible mineral acids, such as, hydrochloric acid, sulfuric acid, sulfurous acid or phosphoric acid; or with organic acids such as methanesulfonic acid, p-toluenesulfonic acid, acetic acid, trifluoroacetic acid, citric acid, fumaric acid, maleic acid, tartaric acid, succinic acid, salicylic acid or the like. The compounds of formula I which have a free carboxy group can also form salts with physiologically compatible bases. Alkali metal, alkaline earth metal, ammonium and alkylammonium salts, such as, Na, K, Ca or tetramethylammonium salts are examples of such salts. The compounds of formula I can also be present in the form of zwitterions.

The compounds of formula I can be solvated, especially hydrated. The hydration can be effected in the course of the manufacturing process or can occur gradually as a consequence of hygroscopic properties of an initially anhydrous compound of formula I.

The compounds of formula I contain at least two asymmetric C atoms and can therefore be present as a mixture of diastereomers or as an optically pure compound.

As used herein, the term "lower" denotes groups which contain 1 to 6, preferably 1 to 4, C atoms. Thus, lower-alkyl, alone or in combination, denotes a straight or branched group containing 1 to 6, preferably 1 to 4, C atoms, such as, methyl, ethyl, propyl, isopropyl, butyl, t-butyl, 2-butyl, pentyl and the like. Lower alkyl groups are preferred as alkyl groups for A. Allyl is an example of alkenyl.

Aryl denotes groups such as phenyl and 1- or 2-naphthyl, optionally substituted by one or more substituents, such as, halogen, for example, chlorine, or lower-alkyl, lower alkoxy, OH, phenyl, CF$_3$, OCF$_3$, cyclopentyl, CN, COOH, COOCH$_3$, COOC$_2$H$_5$, CONH$_2$ or tetrazolyl. Preferred lower-alkyl or alkoxy are CH$_3$, t-butyl and OCH$_3$.

Heteroaryl groups are 5- to 10-membered aromatic groups which consist of one or 2 rings and which contain one or more N and/or O atoms. Examples thereof are 2-, 3- or 4-pyridyl, also in the form of their N-oxides, tetrazolyl, oxadiazolyl, pyrazinyl and quinolyl. Said groups can be substituted, for example, by lower-alkyl, such as, $CH_3$ or halogen, such as, chlorine.

Cycloalkyl groups contain 3 to 8 C atoms. Cyclopropyl, cyclopentyl and cyclohexyl are examples of these.

Heterocyclyl denotes 5- to 10-membered non-aromatic, partially or completely saturated groups, such as, tetrahydroquinolyl, which contain one or two rings and at least one hetero atom, for example, a N atom, and which are optionally substituted by one or more substituents, such as, lower alkyl, for example, methyl.

Examples of tetra- to nonamethyleneimino groups $N(CH_2)_{4-9}$ optionally interrupted by O are hexahydroazepino and morpholino.

Examples of compounds of formula I are those in which:

X is a group $X^1$ in which the guanidino group is unprotected,

Y is hydrogen,

A is aryl, heteroaryl or heterocyclyl,

Q has the above significance,

M is either a group $M^1$ in which $R^3$ and $R^4$ have the above significance, with the proviso that $R^4$ must not be hydrogen or phenyl, when Q, $R^3$ and $R^5$ are simultaneously hydrogen, $R^5$ is hydrogen, lower-alkyl or a group $R^{52}$ optionally bonded via lower-alkylene, $R^{52}$ is —COOH, —COO-lower-alkyl, lower-alkanoyl, OH, lower-alkanoyloxy, $NH_2$, —NHCOO-lower-alkyl, —$NHSO_3H$, —($NHSO_2$ or —$NH-SO_3$)-lower-alkyl, —NH-lower-alkanoyl, —NH-COCOOH, —NHCOCOO-lower-alkyl or —$NH-PO_3(R^9, R^{10})$, or, where Q is not hydrogen, then M can also be a group $M^2$ in which $N(R^6)$ is —$N(CH_2)_{4-9}$ optionally ring-substituted by —COOH or —COO-lower-alkyl.

Additional examples of compounds of formula I are those in which Y is hydrogen, X is a group $X^1$ and M is a group $M^1$ and, where at least one of $R^1$ and $R^2$ (in $X^1$) is not hydrogen and/or when Q is not hydrogen and/or when A is alkyl or cycloalkyl, then M can also be a group $M^2$.

Other examples of compounds of formula I are those in which Y is hydrogen, X is a group $X^2$ and M is a group $M^1$ or $M^2$;

those in which Y is hydrogen, X is a group $X^1$ and M is a group $M^5$ or $M^6$, provided that at least one of $R^1$ and $R^2$ (in $X^1$) is not hydrogen and/or that Q is not hydrogen and/or that A is alkyl or cycloalkyl;

those in which Y is hydrogen, X is a group $X^1$ and M is a group $M^3$ or $M^7$, provided that at least one of $R^1$ and $R^2$ (in $X^1$) is not hydrogen and/or that Q is not hydrogen and/or that A is alkyl or cycloalkyl;

those in which Y and Q are hydrogen, X is a group $X^1$ and M is a group $M^1$ and, when at least one of $R^1$ and $R^2$ (in $X^1$) is not hydrogen and/or when A is alkyl or cycloalkyl, then M can also be a group $M^2$.

Preferred compounds of formula I are those in which Y is hydrogen, Q is lower-alkyl substituted by (OH, —COOH or —COO-lower alkyl), X is a group $X^1$ and M is a group $M^1$ or $M^2$;

those in which X is a group $X^1$, T is $CH_2$, one of $R^1$ and $R^2$ is hydrogen and the other is hydrogen or —COO-(methyl, ethyl, isobutyl or t-butyl);

those in which X is a group $X^1$, T is O, one of $R^1$ and $R^2$ is hydrogen and the other is hydrogen or —$COOC_2H_5$;

those in which X is a group $X^2$ and $R^{11}$ and $R^{21}$ are hydrogen.

Further, A is preferably naphthyl, methylquinolyl, methyltetrahydroquinolyl, methyl, pyridyl or phenyl substituted by t-butyl, $CF_3$, phenyl, cyclopentyl, carboxy, methoxycarbonyl, ethoxycarbonyl, $OCF_3$, CN, $CONH_2$ or tetrazolyl and Q is preferably hydrogen, $CH_3$, $CH_2COOH$, $CH_2CH_2OH$ or $CH_2COOC_2H_5$.

When M is the group $M^1$, $R^3$ is preferably hydrogen, $CH_3$, propyl, isopropyl, butyl, pentyl, allyl, cyclopropyl, cyclopentyl, cyclohexyl, cyclopropylmethyl, cyclohexylmethyl, pyridylmethyl or benzyl, optionally substituted by chlorine or methoxy, and $R^4$ is hydrogen, isopropyl, 2-butyl, isobutyl, phenyl, benzyl or cyclohexyl.

Also, in the group $M^1$, $R^5$ is preferably the group $(CH_2)_{0-2}$—$R^{50}$ and $R^{50}$ is hydrogen, OH, $C(CH_3)_2OH$, $COCH_3$, $OCOCH_3$, COO(hydrogen, $CH_3$ or $C_2H_5$), $NHCOOCH_3$, $NHCOCH_3$, tetrazolyl, $CONH_2$, methyloxadiazolyl, $OCH_3$, benzyloxy, morpholinocarbonyl, $CONHOCH_3$, CONHO-benzyl, $CONHSO_2CH_3$, —$CONHCH_2$-pyridyl, —CONH-cyclopropyl, $CONHCH_2CH_2$—$C_6H_3(OH)_2$, $CONHCH_2CH_2OH$, NHCOCOOH, $NHCOCOOCH_3$, $NHCOCOOC_2H_5$, $NHSO_3H$, $NHSO_2CH_3$, —NHCOO-benzyl, $NHCOCH_2Cl$, $NHCOCH_2OC_6H_5$, $NHCOCOC_6H_5$, $NHCOCOCH_3$, —NHCO-pyrazinyl, —NHCO-pyridyl N-oxide, —NHCO-pyrazinyl, $NHCOCH_2C_6H_3(OH)_2$, $NHPO(OC_6H_5)_2$, $NHPO(OC_2H_5)_2$, NH-(3,4-dioxo-2-hydroxycyclobut-1-enyl) or NH-(2-allyloxy-3,4-dioxocyclobut-1-enyl).

When M is the group $M^2$, —$N(R^6)$ is preferably hexamethyleneimino.

The following are examples of preferred compounds of formula I:

(S)-N4-[(S)-1-(Amino-imino-methyl)piperidin-3-ylmethyl]-N1-carboxymethyl-N1-cyclopentyl-2-(naphthalene-2-sulfonylamino)succinamide,

[(S)-3-[(S)-2-(amino-imino-methyl)piperidin-3-ylmethylcarbamoyl]-2-(naphthalene-2-sulfonylamino)propionyl]-propylaminoacetic acid, N-[N4-[[(S)-1-amidino-3-piperidinyl]methyl]-N2-(2-naphthylsulfonyl)-L-asparaginyl]-N-(o-chlorobenzyl)glycine,

[2-[[(S)-3-[(S)-1-(amino-imino-methyl)piperidin-3-ylmethylcarbamoyl]-2-(naphthalene-2-sulfonylamino)-propionyl]-butylaminolethyl]oxamic acid, (S)-N4-[(S)-1-(amino-imino-methyl)piperidin-3-ylmethyl]-N1-butyl-2-(naphthalene-2-sulfonylamino)-N1-(2-sulfoamino-ethyl)succinamide,

[(S)-3-[(S)-1-(amino-imino-methyl)piperidin-3-ylmethylcarbamoyl]-2-(4-t-butylphenylsulfonylamino)-propionylcyclopropyl-amino]-acetic acid, 2-[(S)-2-[(S)-1-(amino-imino-methyl)-piperidin-3 ylmethylcarbarmoyl]-1-[cyclopropyl-(2-carboxy-ethyl)-carbamoyl]ethylsulfamoyl]-benzoic acid, 3-[[(S)-3-[(S)-1-(amino-imino-methyl)-piperidin-3-ylcarbamoyl]-2-(4-cyano-phenylsulfonylamino)-propionyl]-cyclopropyl-amino]-propionic acid, (S)-N4-[4-(amino-imino-methyl)-morpholin-2-ylmethyl]N1-cyclopropyl-N1-[2-(tetrazol-5-yl)-ethyl]-2-(naphthalen-2-ylsulfonyl)succinamide, ethyl [[(S)-3-[4-amino-imino-methyl)-morpholin-2-ylmethylcarbamoyl]-2-(naphthalen-2-ylsulfonyl)-propionyl]cyclopropylamino]-acetate,

[[(S)-3-[4-(amino-imino-methyl)-morpholin-2-ylmethyl-carbamoyl]-2-(naphthalen-2-ylsulfonyl)-propionyl]-cyclopropylamino]-acetic acid, 2-[[(S)-3-[(S)-1-(amino-imino-methyl)-piperidin-3-ylmethylcarbamoyl]-2-(naphthalen-2-ylsulfonylamino)-propionyl]-cyclopropyl-amino]-ethylsulfamic acid, (S)-N4-[(S)-1-(amino-imino-methyl)-piperidin-3-ylmethyl]-N1-(2-chloroacetylamino-ethyl)-N1-cyclopropyl-2(naphthalen-2-ylsulfonylamino)-succinamide, (S)-N4-[(S)-1-(amino-imino-methyl)-piperidin-3-ylmethyl]-N1-cyclopropyl-2-(naphthalen-2-ylsulfonylamino)-N1-(2-phenoxyacetylamino-ethyl)-succinamide, (S)-N4-[(S)-1-(amino-imino-methyl)-piperidin-3-ylmethyl]-N1-cyclopropyl-2-(naphthalen-2-ylsulfonylamino)-N1-[2-oxo-2-phenylacetylamino)-ethyl]-succinamide, (S)-N4-[(S)-1-(amino-imino-methyl)-piperidin-3-ylmethyl]-N1-cyclopropyl-2-(naphthalen-2-ylsulfonylamino)-N1-[2-(2-oxopropionylamino)-ethyl]-succinimide, (S)-N4-[(S)-1-(amino-imino-methyl)-piperidin-3-ylmethyl]-N1-cyclopropyl-2-(naphthalen-2-ylsulfonylamino)-N1[2-(pyridin-3-ylcarbonylamino)-ethyl]-succinamide, (S)-N4-[(S)-1-(amino-imino-methyl)-piperidin-3-ylmethyl]-N1-cyclopropyl-2-(naphthalen-2-ylsulfonylamino)-N1-[2-(1-oxynicotinoylamino)-ethyl]-succinamide.

Especially preferred are:
N-[N4-[[(S)-1-Amidino-3-piperidinyl]methyl]-N2-(2-naphthylsulfonyl)-L-asparaginyl]-N-cyclopropylglycine, (S)-[[3-[(S)-1-(amino-imino-methyl)piperidin-3-ylmethylcarbamoyl]-2-(naphthalene-2-sulfonylamino)propionyl]cyclopropylamino]propionic acid,

[(S)-3-[(S)-1-(amino-imino-methyl)piperidin-3-ylmethylcarbamoyl]-2-(4-trifluoromethyl-phenylsulfonylamino)-propionylcyclopropyl-amino]acetic acid, 3-[[(S)-3-[(S)-1-(amino-imino-methyl)-piperidin-3-ylcarbamoyl]-2-(4-carbamoyl-phenylsulfonylamino)-propionyl]-cyclopropyl-amino]-propionic acid, (S)-N4-[(S)-1-(amino-imino-methyl)-piperidin-3-ylmethyl]-N1-cyclopropyl-2-(naphthalen-2-ylsulfonylamino)-N1-[2-pyrazin-2-ylcarbonylamino)-ethyl]-succinamide, (S)-N4-[(S)-1-(amino-imino-methyl)-piperidin-3-ylmethyl]-N1-cyclopropyl-N1-[2-(3,4-dihydroxy-phenyl)ethylcarbamoylmethyl]-2-(naphthalen-2-ylsulfonylamino)-succinamide.

The compounds of formula I can be prepared in a known manner by:

a) reacting an acid of the formula

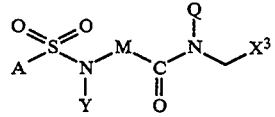   II with an amine of the formula

Q—NHCH$_2$—X   III or a salt thereof, with intermediary protection of functional groups present in the groups A, Y and M (in II) and Q (in III), or b) reacting an amine of the formula

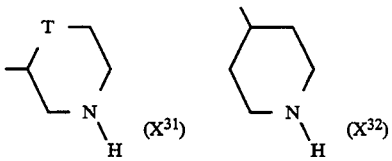   IV wherein X$^3$ is X$^{31}$ or X$^{32}$:

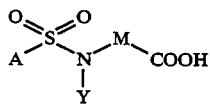

with an amidinating agent, and c) if desired, functionally modifying a reactive group present in group M or Q of a compound of formula I, and d) if desired, converting a compound of formula I into a physiologically compatible salt or converting a salt of a compound of formula I into the corresponding free acid or base.

Conveniently, the acid It is reacted in a solvent, such as, dimethylformamide (DMF) or methylene chloride in the presence of a base, such as, 4-ethylmorpholine, triethylamine, ethyldiisopropylamine or 1,8-diazabicyclo(5.4.0)undec-7-ene (DBU) with a salt of a compound of formula III, for example, a trifluoroacetate, bisulfite, nitrate, hydrochloride or hydroiodide, and with benzotriazol-1-yloxy -tris(dimethylamino)phosphonium hexafluorophosphate (BOP) at room temperature. Functional groups present in the compounds II and III which are to be subjected to intermediary protection, such as, COOH, NH$_2$ and OH, can be protected in the form of lower-alkylOCO benzylOCO or azide groups or benzyloxy groups. The cleavage of a protected carboxy group, such as, COOCH$_3$ or COOCH$_2$H$_5$ to COOH can be effected using sodium hydroxide in ethanol. The conversion of the benzylOCONH— or N$_3$ group into the free amino group can be carried out by catalytic (Pd/C) hydrogenation in ethanol.

In process variant b) a compound of formula IV in a solvent, such as, DMF or methanol can be reacted in the presence of a base, such as, triethylamine with formamidinesulfonic acid or 3,5-dimethyl-1-pyrazolylformamidinium nitrate, conveniently at a temperature up to 50° C.

The following can be mentioned as functional modifications in variant c):

1. The saponification of an ester group, such as, ethoxycarbonyl, for example, in ethanol or methanol, using a base, such as, aqueous NaOH, or the saponification of an ester group, such as, acetoxy, for example, in tetrahydrofuran (THF), using a base, such as, aqueous LiOH;

2. the hydrogenation of the double bond in an alkylene group, for example, in ethanol and water in the presence of palladium on carbon (Pd/C);

3. the hydrogenation of an aryl group to the corresponding cycloalkyl groups, for example, in ethanol in the presence of acetic acid and Pd/C;

4. the cleavage of an ether, such as, a benzyl ether to the corresponding alcohol, for example, using a solution of boron tribromide in methylene chloride;

5. the etherification of an alcohol, for example, using a lower alkyl halide, such as, methyl iodide in the presence of a solution of DBU in THF;

6. the conversion of a carboxylic acid into the carboxamide by reaction with an amine, such as, morpholine, for example, in DMF in the presence of BOP and 4-ethylmorpholine;

7.a) the conversion of an amine into a quadrate acid derivative thereof, for example, by reaction with 3,4-bis(2-propenyloxy)-3-cyclobutene-1,2-dione in THF at 0° C. and, if desired, 7.b) the catatalytic cleavage of the 2-propenyl group from the quadrate acid derivative obtained under a), for example, using palladium(II) acetate in acetonitrile and water in the presence of triethyl phosphite and then sodium 2-ethylcaproate.

The N-sulfonated amino acids of formula II can be prepared by reacting a corresponding reactive sulfonic acid derivative, such as, the sulfochloride A—SO$_2$Cl with the corresponding intermediary protected amino acid derivative HN(Y)—M—COO—t—butyl, for example, as described in EP-A-468231. The cleavage of the t-butyl ester to the desired acid can be carried out using trifluoroacetic acid in CH$_2$Cl$_2$ or using hydrochloric acid in ethyl acetate.

Further, the amino acids II in which M is the group M$^1$ can be prepared according to the following Reaction Schemes (1), (2), (3):

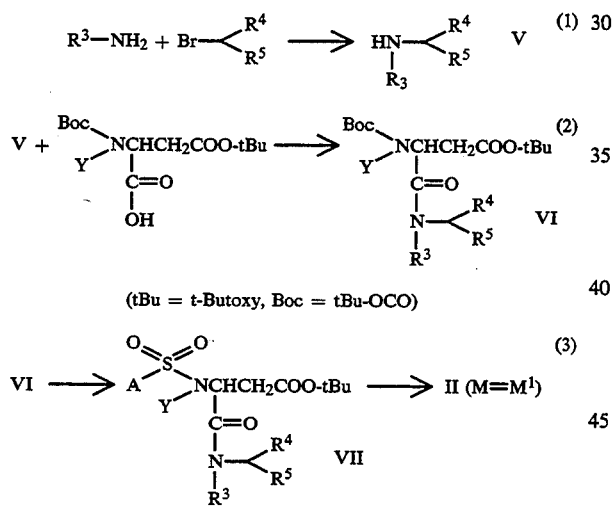

(tBu = t-Butoxy, Boc = tBu-OCO)

Reaction (1) can be carried out in a solvent ,such as, toluene at an elevated temperature. Reaction (2) is conveniently carried out in the same manner as the reaction of a compound of formula II with a compound of formula III described above. Reaction (3) is undertaken by firstly cleaving the Boc group from the N atom present in VI, for example, in acetonitrile or dioxane with p-toluenesulfonic acid, and reacting the compound obtained with a sulfochloride A—SO$_2$Cl in dioxane. The hydrolysis of an ester of formula VII to the corresponding acid of formula II can be effected using trifluoroacetic acid in methylene chloride.

The preparation of an ester of formula VII in which R$^5$ is tetrazolyl proceeds via the corresponding ester in which R$^5$ is cyano. The conversion of the cyano group into the tetrazolyl group can be carried out in DMF using ammonium chloride and sodium azide.

The guanidine starting materials of formula III in which X is the group X$^1$ and R$^1$, R$^2$ and Q are hydrogen can be prepared as described in EP-A-468231, for example, starting from 3-picolylamine or from 2-aminomethyl-4-benzylmorpholine depending on whether a guanidine of formula III with T=CH$_2$ or T=O is desired. The procedure described in Example 36B can be adopted for the preparation of an optically active guanidine of formula III. N-(3-Pyridylmethyl)benzamide is hydrogenated catalytically (Pd/C) in ethanol and hydrochloric acid to (RS)-N-piperidin-3ylmethylbenzamide. By salt formation with D-mandelic acid in methylene chloride, there can be crystallized, after addition of diethyl ether, (R)-N-piperidin-3-ylmethyl-benzamide mandelate. The resulting compound can then be amidinated in DMF using triethylamine and formamidinesulfonic acid. By heating a solution of the resulting mandelate in concentrated hydrochloric acid there can be obtained the (S)-guanidine of formula III in which X is the group X$^1$ and Q, R$^1$ and R$^2$, are hydrogen.

A guanidine of formula III wherein X is X$^2$ and Q, R$^{11}$ and R$^{21}$ are hydrogen can be prepared in analogy to those wherein X is X$^1$, T is CH$_2$ and Q, R$^1$ and R$^2$ are hydrogen, for example, according to Reaction Scheme (4) hereinafter and as described in Example 67a)b) hereinafter:

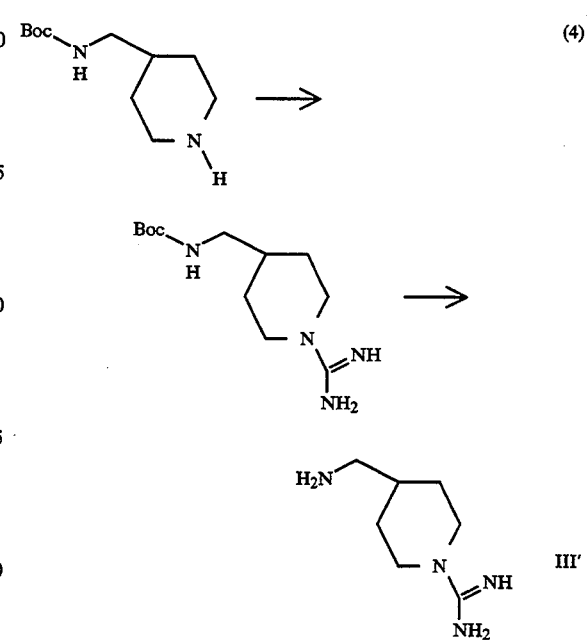

A guanidine of formula III wherein one of R$^1$ and R$^2$ or one of R$^{11}$ and R$^{21}$ is hydrogen can be prepared, for example, via compounds of type VIII, IX, X in Reaction Scheme (5) hereinafter and as described in Example 48a)b)c) hereinafter:

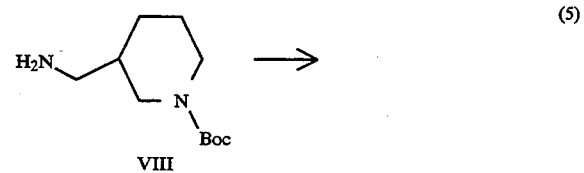

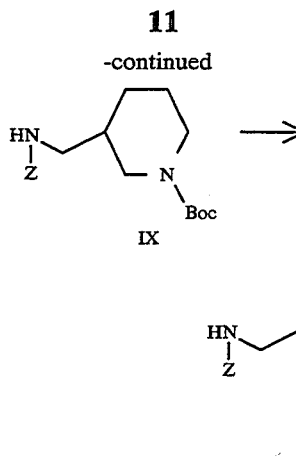

IX

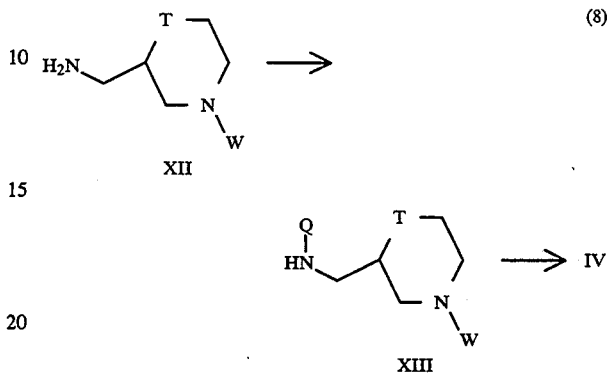

XII

XIII

Thus, an amine of formula VIII is reacted in hexane and water with tetrabutylammonium hydrogen sulfate and 1N sodium hydroxide solution and then with benzyl chloroformate. The Boc group is cleaved from the resulting compound of formula IX using a solution of hydrochloric acid in ethyl acetate. The product is converted into the compound of formula X in DMF using triethylamine and formamidinesulfonic acid. In order to protect the amidino group in compound X, the latter is reacted for example, with ethyl chloroformate in methylene chloride. By hydrocatalytic cleavage of the Z group, there is obtained a piperidine derivative of formula III in which X is the group $X^1$ and one of $R^1$ and $R^2$ is ethoxycarbonyl. The corresponding morpholine derivative of formula III (T=O) can be prepared in an analogous manner.

In order to protect the amidino group present in a guanidine of formula III with a Boc group, a guanidine of type X can be reacted with di-t-butyl dicarbonate (in place of ethyl chloroformate) in dioxane.

A guanidine of formula III wherein Q is not hydrogen can be prepared, for example, according to the Reactions (6) and (7), which follow, as described in Example 9a) to d) hereinafter:

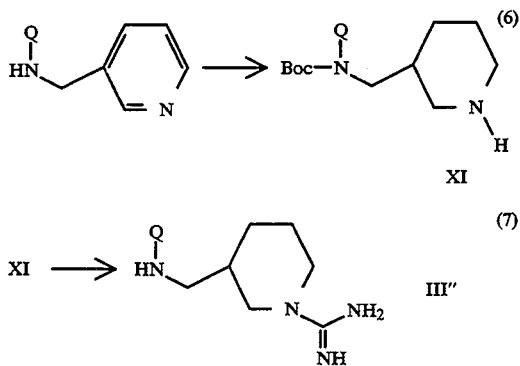

Guanidines of formula III wherein Q is not hydrogen and T is O are obtained by a) reacting 2-aminomethyl-4-benzylmorpholine (J. Med. Chem. 33, 1990, 1406–1413) with di-t-butyl dicarbonate in dioxane, b) reacting the resulting amine protected with Boc with NaH and a bromide Q—Br in DMF, c) cleaving the benzyl group from the resulting product by hydrogenation in ethanol in the presence of Pd/C, and d) amidinating the resulting morpholine derivative as described above for compound IV and cleaving off the Boc group.

A amine starting material of formula IV is prepared, for example, according to the following reaction (8) in which W is a protecting group, such as, Boc or Z.

For the preparation of a compound IV in which Q is not hydrogen, a primary amine of formula XII [preparable from 3-hydroxy-methylpiperidine as described in EP-A-468231 and in Examples 12 a) to g) hereinafter] is reacted with a base, such as, Hünig base and a bromide of the formula Q-Br to give the corresponding secondary amine of formula XIII. An acid of formula II is then coupled with the resulting amine of formula XIII (as described in the above coupling, of II+III). The Boc protecting group is then cleaved using trifluoroacetic acid in methylene chloride, p-toluenesulfonic acid in acetonitrile or a solution of hydrogen chloride in ethyl acetate. The cleavage of the Z protecting group is carried out by hydrogenation in ethanol in the presence of Pd/C. To prepare a compound of formula IV in which Q is hydrogen, the acid of formula II is coupled with the amine of formula XII (in place of XIII).

The preparation of an amine starting material of formula IV, in which M is the group $M^1$ and $R^5$ is —NHCOCOO-lower alkyl, proceeds via a compound of formula IV in which $R^5$ is for an azido group. The conversion of azido into —NHCOCOO-lower alkyl can be effected by catalytic hydrogenation (Pd/C in methanol) followed by transformation of the resulting amino group into —NHCOCOO-lower alkyl by reaction with a mono-lower alkyl oxalyl chloride in the presence of pyridine in methylene chloride. When pyrazinecarboxylic acid, in the presence of Hünig base in methylene chloride, is used in place of a mono-lower alkyl oxalyl chloride, then there is obtained a compound of formula IV in which M is $M^1$ and $R^5$ is —NHCO-pyrazinyl.

Moreover, many of the Examples hereinafter contain detailed information concerning the preparation of certain compounds of formulas II, III and IV. The compounds of formula III in which X is the group $X^1$ and at least one of $R^1$, $R^2$ and Q is other than hydrogen or in which X is the group $X^2$, as well as the compounds of formula IV in which M is the group $M^1$ or, wherein $X^3$ is the group $X^{32}$ or wherein X is the group $X^{31}$ and simultaneously Q is not hydrogen and/or where A is alkyl or cycloalkyl, then M can also be one of the groups $M^2$ to $M^8$ are also part of the present invention.

The compounds of formula I, their solvates and their salts inhibit not only thrombin-induced platelet aggregation, but also thrombin-induced clotting of fibrinogen in blood plasma. The compounds of formula I influence not only platelet-induced, but also plasmatic blood clotting. They, therefore, prevent especially the formation of hyaline thrombin and of platelet-rich thrombin and can be used in the control or prevention of illnesses, such as, thrombosis, stroke, cardiac infarct, inflammation and arteriosclerosis. Further, the compounds of formula I have an effect on tumor cells and prevent the formation of metastases. Accordingly, they can also be used as antitumor agents.

A differential inhibition of thrombin and other serine proteases by the above compounds is desirable in order to obtain compounds having as high a specificity as possible and at the same time to avoid possible side-effects. Alongside other tested serine proteases, the ratio of the inhibition of trypsin to the inhibition of thrombin was taken as the general measurement for the specificity of a compound (q in the Table hereinafter), because trypsin as the most unspecific serine protease can be readily inhibited by the widest variety of inhibitors. In order for the inhibition of thrombin and trypsin to be directly comparable, notwithstanding the use of different substrates, the inhibition constant $K_i$ independent of substrate and enzyme concentration was determined as the measurement of the inhibition.

Specific chromogenic peptide substrates can be used to determine the inhibition of the catalytic activity of the above proteases. The inhibition of the amidolytic activity of thrombin and trypsin by the above compounds was determined as described here in after.

The measurements were carried out on microtitre plates at room temperature. For this, in each well of the plate 150 μl of buffer (50 mM Tris, 100 mM NaCl, 0.1% polyethylene glycol; pH 7.8) were mixed with 50 μl of the inhibitor dissolved in dimethylsulfoxide (DMSO) and diluted in the buffer, and 25 gl of human thrombin (0.5 nM final conc.) were added. After incubation for 10 minutes, the reaction was started by the addition of chromogenic substrate S-2238 (hydrogen-D-Phe-Pip-Arg-paranitroaniline from Kabivitrum; 10 or 50 μl final conc.) and the hydrolysis of the substrate was followed spectrophotometrically on a kinetic microtiter plate reader for 5 minutes. After graphical presentation of the inhibition curves, the Ki values were determined according to the method described in Biochem. J. 55, 1955, 170–171. The inhibi-tion of trypsin was effected analogously, but using the substrate S-2251 (hydrogen-D-Val-Leu-Lys-paranitroaniline) in 200 and 750 μM final concentration.

The results will be evident from the following Table:

| Compound of Example | $K_i$ (nM) thrombin | $K_i$ (nM) trypsin | q |
| --- | --- | --- | --- |
| 2k | 0.40 | 7700 | 19250 |
| 4a | 0.27 | 1900 | 7143 |
| 4i | 0.82 | 5000 | 6098 |
| 4k | 0.30 | 8100 | 27000 |
| 4l | 0.56 | 5000 | 8929 |
| 5 | 0.22 | 4300 | 19545 |
| 15a | 0.85 | 6100 | 7176 |
| 15b | 0.99 | 2100 | 2121 |
| 16 | 0.81 | 2100 | 2593 |
| 26b | 0.25 | 130 | 524 |
| 29 | 0.44 | 1800 | 4.91 |
| 30 | 0.75 | 2400 | 3200 |
| 31c | 2.20 | 7700 | 3500 |

The compounds of formula I have a low toxicity. Thus, the compounds produced in the Examples enumerated in the Table have an LD50 of 125–500 mg/kg in mice upon intravenous administration.

As mentioned earlier, medicaments containing a compound of formula I, a solvate or salt thereof are likewise objects of the present invention, as is a process for the preparation of such medicaments which comprises by bringing one or more of said compounds, solvates or salts and, if desired, other therapeutically valuable substances into a galenical dosage form. The medicaments can be administered orally as dragées, hard and soft gelatine capsules, solutions, emulsions or suspensions, or rectally, for example, in the form of suppositories, or as a spray. The administration can, however, also be effected parenterally, for example, in the form of injection solutions.

For the preparation of tablets, coated tablets, dragées and hard gelatin capsules, the active substance can be mixed with pharmaceutically inert, inorganic or organic excipients. Lactose, maize starch or derivatives thereof, talc, stearic acid or its salts can be used, for example, as such excipients for tablets, coated tablets, dragées and hard gelatin capsules. Suitable excipients for soft gelatine capsules are, for example, vegetable oils, waxes, fats, semi-solid and liquid polyols; depending on the nature of the active substance no excipients are, however, usually required in the case of soft gelatin capsules. Suitable excipients for the preparation of solutions and syrups are, for example, water, polyols, saccharose, invert sugar and glucose, suitable excipients for injection solutions are, for example, water, alcohols, polyols, glycerol and vegetable oils and suitable excipients for suppositories are natural or hardened oils, waxes, fats, semi-liquid or liquid polyols. The pharmaceutical preparations can also contain preservatives, solubilizers, stabili-zers, wetting agents, emulsifiers, sweeteners, colorants, flavor-ants, salts for varying the osmotic pressure, buffers, coating agents or antioxidants.

For the control or prevention of the illnesses mentioned above, the dosage of the active substance, that is, a compound of formula I, can vary within wide limits and will, of course, be fitted to the individual requirements in each particular case. In general, in the case of oral or parenteral, for example, intravenous or subcutaneous, administration a dosage of about 0.1 to 20 mg/kg, preferably of about 0.5 to 4 mg/kg, per day should be appropriate for adults, although the upper limit just given can also be increased or lowered, when this is shown to be indicated.

EXAMPLE 1

A solution of 0.85 g of t-butyl-(S)-N-cyclohexyl-N-[(ethoxycarbonyl)methyl]-3-(2-naphthylsulfonamido)-succinamate in 21 ml of methylene chloride is treated at 0° C. with 2.4 ml of trifluoroacetic acid and stirred at room temperature. The foam obtained after evaporation of the solution is dissolved in 13 ml of DMF, then treated with 0.98 ml of 4-ethylmorpholine, 0.68 g of benzotriazol-1-yloxy-tris(dimethylamino)phosphonium hexafluorophosphate and 0.43 g of (S)-1-amidino-3-(aminomethyl)piperidine dihydrochloride and stirred at room temperature. The reaction mixture is evaporated and the residue is chromatographed on silica gel with ethyl acetate, then with ethyl acetate-acetone-acetic acid-water 16:2:1:1. There is isolated 0.85 g of N-[N4-[[(S)-1-amidino-3-piperidinyl]methyl]-N2-(2-naphthyl-sulfonyl)-L-asparaginyl]-N-cyclohexylglycine ethyl ester diacetate, Fab-MS: 629.3 (M+H)+.

Preparation of the starting material:

a) 3.78 ml of 4-ethylmorpholine, 4.42 g of benzotriazol-1-yloxytris(dimethylamino)phosphonium hexafluorophosphate (BOP) and a solution of 2.25 g of N-cyclohexylglycine ethyl ester (J. Heterocycl. Chem. 23, 1986, 929–933) in 8 ml of DMF are added to a solution of 2.89 g of N-Boc-L-aspartic acid β-t-butyl ester in 50 ml of DMF. The reaction mixture is stirred at room temperature, then evaporated and the residue is partitioned between ethyl acetate and water. The organic phase is dried, evaporated and the residue is chromatographed on silica gel with ethyl acetate/hexane 1:1. There are thus isolated 4.5 g of t-butyl-(S)-3-(1-t-butoxyformamido)-N-cyclohexyl-N-[(ethoxycarbonyl)methyl]succinamate, Fab-MS: 457 (M+H)+.

b) A solution of 2.1 g of the product from a) in 22 ml of acetonitrile is treated with 2.2 g of p-toluenesulfonic acid monohydrate while stirring. The resulting solution is evaporated and dried. Then 2.4 g of the residue are dissolved in 45 ml of dioxane and treated with a solution of 1.56 g of β-naphthyl sulfochloride in 15 ml of dioxane. 1.9 g of sodium bicarbonate in 19 ml of water are added thereto. After stirring, the reaction mixture is poured on to ice and extracted with ethyl acetate. The organic phase is washed with water, then dried and evaporated. The residue is chromatographed on silica gel with hexane-ethyl acetate 4:1. There is obtained 0.85 g of t-butyl-(S)-N-cyclohexyl-N-[(ethoxycarbonyl) methyl]-3-(2-naphthylsulfonamido)succinamate, Fab-MS: 547 (M+H)+.

EXAMPLE 2

2.A) The following compounds are prepared analogously to Example 1:

a) N-[N4-[[(S)-1-Amidino-3-piperidinyl]methyl]-N2-(2-naphthylsulfonyl)-L-asparaginyl]-N-cyclopropylglycine ethyl ester acetate, MS (ion spray): 587.3 (M+H)+, b) ethyl [[(S)-3-[(S)-1-(amino-imino-methyl)piperidin-3-ylmethylcarbamoyl]-2-(naphthalene-2-sulfonylamino)propionyl]benzylaminolacetate acetate, MS (ion spray): 637.3 (M+H)+, c) N-[N4-[[(S)-1-amidino-3-piperidinyl]methyl]-N2-(2-naphthylsulfonyl)-L-asparaginyl]-N-cyclohexylglycine methyl ester acetate, MS (ion spray): 629.4 (M+H)+, d) N-[N4-[[(S)-1-amidino-3-piperidinyl]methyl]-N2-(2-naphthylsulfonyl)-L-asparaginyl]-N-methylglycine ethyl ester hydrochloride, MS (ion spray): 561.5 (M+H)+, e) N-[N4-[[(S)-1-amidino-3-piperidinyl]methyl]-N2-(2-naphthylsulfonyl)-L-asparaginyl]-N-isopropylglycine ethyl ester hydrochloride, MS (ion-spray): 589.0 (M+H)+, f) ethyl (S)-[N-allyl-[3-[(S)-1-amino-imino-methyl)-piperidin-3-ylmethylcarbamoyl]-2-(naphthalene-2-sulfonylamino)propionyl]amino]acetate hydrochloride, MS (ion-spray): 587.0 (M+H)+, g) ethyl N-[(S)-3-[(S)-1-(amino-imino-methyl)piperidin-3-ylmethylcarbamoyl]-2-(naphthalene-2-sulfonylamino)propionyl]butylamino]acetate hydrochloride, MS (ion-spray): 603.2 (M+H)+, h) N-[N4-[[(S)-1-amidino-3-piperidinyl]methyl]-N2-(2-naphthylsulfonyl)-L-asparaginyl]-N-(cyclopropylmethyl)glycine ethyl ester hydrochloride, MS (ion-spray): 601.2 (M+H)+, i) (S)-N4-[(S)-1-(amino-imino-methyl)piperidin-3-ylmethyl]-N1-ethoxycarbonylmethyl-N1-cyclopentyl-2-(naphthalene-2-sulfonylamino)succinamide hydrochloride, MS (ion-spray): 615.2 (M+H)+, j) N-[N4-[[(S)-1-amidino-3-piperidinyl]methyl]-N2-(2-naphthylsulfonyl)-L-asparaginyl]-L-leucine ethyl ester hydrochloride, MS (ion-spray): 603.0 (M+H)+, k) N-[N4-[[(S)-1-amidino-3-piperidinyl]methyl]-N2-(2-naphthylsulfonyl)-L-asparaginyl]-N-cyclopropyl-[β-alanine ethyl ester hydrochloride, MS (ion-spray): 601.3 (M+H)+, l) ethyl (S)-3-[allyl-[3-[(S)-1-(amino-imino-methyl)-piperidin-3-ylmethylcarbamoyl]-2-(naphthalene-2-sulfonylamino)propionyl]amino]propionate hydrochloride, MS (ion-spray): 601.2 (M+H)+, m) (S)-N4-[(S)-1-(amino-imino-methyl)piperidin-3-ylmethyl]-N1-butyl-N1-(2-ethoxycarbonylethyl)-2-(naphthalen-2-ylsulfonylamino)-succinamide hydrochloride, MS (ion-spray): 617.5 (M+H)+, n) ethyl (S)-3-[(S)-1-(amino-imino-methyl)piperidin-3-ylmethylcarbamoyl]-2-(naphthalen-2-ylsulfonylamino)-N-pentyl-propionylaminoacetate hydrochloride (1:1), MS (ion-spray): 617.1 (M+H)+.

2.B) Preparation of the starting materials:

2.B)a) 14.0ml of ethyl 3-bromopropionate are added to a solution of 15.4 ml of cyclopropylamine in 100 ml of toluene and the reaction mixture is heated to 90° for 3 hours. Subsequently, the precipitated salt is filtered and the filtrate is distilled. There are obtained 9.5 g of N-cyclopropyl-β-alanine ethyl ester, Fab-MS: 157 (M+H)+.

2.B)b) The following compounds are prepared analogously to the process of 2.B)a) using allylamine and, respectively, butylamine in place of cyclopropylamine:

1) N-Allyl-β-alanine ethyl ester, Fab-MS: 157 (M+),
2) ethyl 3-butylaminopropionate, Fab-MS: 173 (M+).

2.B)c) The following triesters are obtained analogously to Example 1 a) but using an N-substituted glycine ester in place of N-cyclohexylglycine ethyl ester:

2.B)c)1) t-Butyl (S)-2-(2-t-butoxyformamido)-N-cyclopropyl-N-[(ethoxycarbonyl)methyl]succinamate, Fab-MS: 415 (M+H)+, 2.B)c)2) t-butyl (S)-N-benzyl-3-butoxycarbonylamino-N-ethoxycarbonylmethyl-succinamate, MS (ion spray): 465.2 (M+H)+, 2.B)c)3) t-butyl (S)-3-t-butoxycarbonylamino-N-cyclohexyl-methyl-N-methoxycarbonylmethyl-succinamate, MS (ion spray): 457.3 (M+H)+.

2B)d) The following compounds are obtained analogously to Example 1 b):

2.B)d)1) t-butyl (S)-N-Cyclopropyl-N-ethoxycarbonylmethyl-3-(naphthalene-2-sulfonylamino)succinamate, Fab-MS: 505 (M+H)+, 2.B)d)2) t-butyl (S)-N-benzyl-N-ethoxycarbonylmethyl-3-(naphthalen-2-ylsulfonylamino)-succinamate, MS (ion spray): 555.2 (M+H)+, 2.B)d)3) t-butyl (S)-N-cyclohexylmethyl-N-methoxycarbonylmethyl-3-(naphthalen-2-ylsulfonylamino)-succinamate, MS (ion spray): 547.2 (M+H)+.

2.B)e) 10.6ml of 4-ethylmorpholine, 4.6g of N-(dimethyl-aminopropyl)-N'-ethylcarbodiimide hydrochloride, 244 mg of 4-dimethylaminopyridine and 3.1 g of sarcosine ethyl ester hydrochloride added in succession to a solution of 5.78 g of N-Boc-L-aspartic acid-β-t-butyl ester in 100 ml of methylene chloride. After stirring the reaction mixture is poured into ice-cold 5% potassium hydrogen sulfate-10% potassium sulfate solution and extracted with ethyl acetate. The organic phase is washed with water, then dried, evaporated and the residue is chromatographed on silica gel with hexane-ethyl acetate (3:1). There are obtained 6.8 g of t-butyl (S)-3-t-butoxycarbonylamino-N-ethoxycarbonylmethyl-N-methylsuccinamate, MS (ion spray): 389.4 (M+H)+.

2.B)f) The following triesters are obtained analogously to 2.B)e), but using N-substituted glycine esters in place of sarcosine ethyl ester:

2.B)f)1) t-butyl (S)-3-t-butoxycarbonylamino-N-ethoxy- carbonylmethyl-N-isopropyl-succinamate, MS (ion spray): 417.1 (M+H)+, 2.B)f)2) t-butyl-(S)-N-allyl-N-[(ethoxycarbonyl)methyl]-3-(1-t-butoxyformamido)succinamate, MS (ion spray): 415.2 (M+H)+, 2.B)f)3) N-[N,3-bis-t-butoxycarbonyl)-L-alanyl]-N-butylglycine ethyl ester, MS (ion spray): 431.2 (M+H)+, 2.B)f)4) N-[N,3-bis(t-butoxycarbonyl)-L-alanyl]-N-(cyclopropylmethyl)glycine ethylester, MS (ion spray): 428.2 M+, 2.B)f)5) t-butyl (S)-3-t-butoxycarbonylamino-N-cyclopentyl-N- ethoxycarbonylmethyl-succinamate, MS (ion spray): 443.3 (M+H)+, 2.B)f)6) t-butyl (S)-3-t-butoxycarbonylamino-N4-cyclobutyl-N4-ethoxycarbonylmethyl-succinamate, MS (ion spray): 429.2 (M+H)+, 2.B)f)7) t-butyl (S)-3-t-butoxycarbonylamino-N-t-butyl-N- ethoxycarbonylmethyl-succinamate, MS (ion spray): 431.2 (M+H)+, 2.B)f)8) t-butyl (S)-3-t-butoxycarbonylamino-N-ethoxycarbonyl- methyl-N-pentyl-succinamate, MS (ion spray): 445.3 (M+H)+.

2.B)g) Analogously to 2.B)e), but using L-leucine ethyl ester in place of sarcosine ethyl ester, there is obtained N-[N,3-bis(t-butoxy carbonyl)-L-alanyl]-L-leucine ethyl ester, Fab-MS: 431.2 (M+H)+.

2.B)h) The following triesters are obtained analogously to 2.B)e), but using the esters prepared according to Example 2.B)a) and b):

2.B)h)1) t-butyl (S)-3-t-butoxycarbonylamino-N-cyclopropyl-N-(2-ethoxycarbonyl-ethyl)-succinamate, MS: 429 (M+H)+, 2.B)h)2) t-butyl (S)-3-t-butoxycarbonylamino-N-allyl-N-(2-ethoxycarbonyl-ethyl)succinamate, MS: 429 (M+H)+, 2.B)h)3) t-butyl (S)-3-t-butoxycarbonylamino-N-butyl-N-(2-ethoxycarbonylethyl)succinamate, MS (ion spray): 445.6 (M+H)+.

2.B)i) A solution of 6.7 g of t-butyl (S)-3-t-butoxy-carbonyl- amino-N-ethoxycarbonylmethyl-N-methylsuccinamate in 80 ml of dioxane is treated with 8.2 g of p-toluenesulfonic acid monohydrate. After stirring, 43.1 ml of 1N sodium hydroxide solution, 4.34 g of sodium bicarbonate and a solution of 7.8 g of 2-naphthyl sulfochloride in 37 ml of dioxane are added. After stirring the reaction mixture is poured into ice-cold 5% potassium hydrogen sulfate-10% potassium sulfate solution and extracted with ethyl acetate. The organic phase is washed with dilute sodium chloride solution, then dried and evaporated. After chromatography on silica gel with hexaneoethyl acetate (3:1), there are isolated 2.0g of t-butyl (S)-N-[(ethoxycarbonyl)-methyl]-N-methyl-3-(2-naphthylsulfonamido)succinamate, MS (ion spray): 479.9 (M+H)+.

2.B)j) The following diesters are obtained analogously to 2.B)i), but using the triesters of Examples 2.B)f), g) and h) in place of the triester of Example 2.B)e):

2.B)j)1) N-[3-(t-butoxycarbonyl)-N-(2-naphthylsulfonyl)-L-alanyl]-N-isopropylglycine ethyl ester, Fab-MS: 433 (M-t-butoxy), 2.B)j)2) N-allyl-N-[3-(t-butoxycarbonyl)-N2-(2-naphthyl- sulfonyl)-L-alanyl]glycine ethyl ester, MS (ion spray): 505.0 (M+H)+, 2.B)j)3) t-butyl (S)-N-butyl-N-ethoxycarbonylmethyl-3-(naphthalene-2-sulfonylamino)-succinamate, MS (ion spray): 54.3 (M+H)+, 2.B)j)4) N-(cyclopropylmethyl)-N-[4-t-butoxycarbonyl)-N-(2-naphthylsulfonyl)-L-alanyl]glycine ethyl ester, Fab-MS: 445 (M-t-butoxy), 2.B)j)5) t-butyl (S)-N-cyclopentyl-N-ethoxycarbonylmethyl-3-(naphthalene-2-sulfonylamino)-succinamate, MS (ion spray): 533.0 (M+H)+, 2.B)j)6) t-butyl (S)-N-cyclobutyl-N-ethoxycarbonylmethyl-3-(naphthalene-2-sulfonylamino)-succinamate, MS (ion spray): 519.1 (M+H)+, 2.B)j)7) t-butyl (S)-N-t-butyl-N-ethoxycarbonylmethyl-3-(naphthalene-2-sulfonylamino)-succinamate, MS (ion spray): 521.1 (M+H)+, 2.B)j)8) ethyl (S)-2-[(S)-3-t-butoxycarbonyl-2-(naphthalene-2-sulfonylamino)-propionylamino]-4-methylpentanoate, MS (ion spray): 521.0 (M+H)+, 2.B)j)9) ethyl N-[3-(t-butoxycarbonyl)-N-(2-naphthylsulfonyl)-L-alanyl]-N-cyclopropyl-β-alanine ethyl ester, MS (ion spray): 517.1 (M−H)−, 2.B)j)10) ethyl N-allyl-N-[O-t-butyl-N-(naphthalene-2-yl- sulfonyl)-L-aspartyl]-β-alanine ethyl ester, MS (ion spray): 519.4 (M+H)+, 2.B)j)11) t-butyl (S)-N-butyl-N-(2-ethoxycarbonylethyl)-3-(naphthalen-2-ylsulfonylamino)-succinamate, Fab-MS: 479 (M-isobutyl ester), 2.B)j) 12) t-butyl (S)-N-ethoxycarbonylmethyl-3-(naphthalen-2-ylsulfonylamino)-N-pentylsuccinamate, Fab-MS: 479 (M-isobutyl ester).

EXAMPLE 3

A solution of 0.85 g of N-[N4-[[(S)-2-amidino-3-piperidinyl]methyl]-N2-(2-naphthylsulfonyl)-L-asparaginyl]-N-cyclohexylglycine ethyl ester diacetate (Example 1) in 6 ml of ethanol is treated with 6.0ml of 1N sodium hydroxide solution. After stirring, 6.0 ml of 1N hydrochloric acid are added. The resulting solution is evaporated and the residue is chromatographed on a RP-18 column with acetonitrile-water. There is obtained 0.25 g of N-[N4-[[(S)-1-amidino-3-piperidinyl]methyl]-N2-(2-naphthylsulfonyl)-L-asparaginyl]-N-cyclohexylglycine, MS (ion spray): 601.3 (M+H)+.

EXAMPLE 4

The following acids are obtained analogously to Example 3, but starting from the esters of Example 2.A):
a) N-[N4-[[(S)-1-Amidino-3-piperidinyl]methyl]-N2-(2-naphthylsulfonyl)-L-asparaginyl]-N-cyclopropylglycine, MS (ion spray): 559.0 (M+H)+,
b) [[(S)-3-[(S)-1-(amino-imino-methyl)piperidin-3-ylmethylcarbamoyl]-2-(naphthalene-2-sulfonylamino)-propionyl]-benzylamino]-acetic acid, MS (ion spray): 609.1 (M+H)+,
c) N-[N4-[[(S)-1-amidino-3-piperidinyl]methyl]-N2-(2-naphthylsulfonyl)-L-asparaginyl]-N-cyclohexylglycine, MS (ion spray): 615.4 (M+H)+, d) N-[N4-[[(S)-1-amidino-3-piperidinyl]methyl]-N2-(2-naphthylsulfonyl)-L-asparaginyl]-N-methylglycine, MS (ion spray): 532.9 (M+H)+, e) N-[N4-[[(S)-1-amidino-3-piperidinyl]methyl]-N2-(2-naphthylsulfonyl)-L-asparaginyl]-N-isopropylglycine, MS (ion spray): 561.2 (M+H)+, f) [[(S)-3-[(S)-1-(amino-imino-methyl)piperidin-3-ylmethylcarbamoyl]-2-(naphthalene-2-sulfonylamino)propionyl]allylamino]acetic acid, MS (ion spray): 557.2 (M−H)−, g) [[(S)-3-[(S)-1-(amino-imino-methyl)piperidin-3-ylmethylcarbamoyl]-2-(naphthalene-2-sulfonylamino)propionyl]butylamino]acetic acid, MS (ion spray): 575.3 (M+H)+, h) N-[N4-[[(S)-1-amidino-3-piperidinyl]methyl]-N2-(2-naphthyl-sulfonyl)-L-asparaginyl]-N-(cyclopropylmethyl)glycine, MS (ion spray): 573.3 (M+H)+, i) (S)-N4-[(S)-1-(amino-imino-methyl)piperidin-3-ylmethyl]-N1-carboxymethyl-N1-cyclopentyl-2-(naphthalene-2-sulfonylamino)succinamide, MS (ion spray): 587.2 (M+H)+, j) N-[N4-[[(S)-1-amidino-3-piperidinyl]methyl]-N2-(2-naphthylsulfonyl)-L-asparaginyl]-L-leucine, MS (ion spray): 575.1 (M+H)+, k) (S)-[[3-[(S)-1-(amino-imino-methyl)piperidin-3-ylmethylcarbamoyl]-2-(naphthalene-2-sulfonylamino)propionyl]cyclopropylamino]propionic acid, MS (ion spray): 573.2 (M+H)+, l) (S)-3-[allyl-[3-[(S)-1-(amino-imino-methyl)piperidin-3-ylmethylcarbamoyl]-2-(naphthalene-2-sulfonylamino)propionyl]amino]propionic acid, MS (ion spray): 573.3 (M+H)+, m) 3-[(S)-3-[(S)-1-(amino-imino-methyl)piperidin-3-ylmethylcarbamoyl]-N-butyl-2-(naphthalen-2-ylsulfonylamino)propionylamino]propionic acid, MS (ion spray): 589.4 (M+H)+, n) [(S)-[3-[(S)-1-(amino-imino-methyl)piperidin-3-ylmethylcarbamoyl]-2-(naphthalen-2-ylsulfonylamino)-propionyl]-pentylaminoacetic acid, MS (ion spray): 589.5 (M+H)+.

EXAMPLE 5

A solution of 50mg of [[(S)-3-[(S)-1-(amino-imino-methyl)- piperidin-3-ylmethylcarbamoyl]-2-(naphthalene-2-sulfonylamino)propionyl]allylamino]acetic acid (Example 4.f) in 4 ml of ethanol and 1 ml of water is treated with 10 mg of Pd/C and hydrogenated under normal conditions. After 4 hours, the catalyst is filtered and the filtrate is evaporated. There are obtained 50 mg of [(S)-3-[(S)-2-(amino-imino-methyl)piperidin-3-ylmethylcarbamoyl]-2 -(naphthalene-2-sulfonylamino)propionyl]-propyl-aminoacetic acid, MS (ion spray): 561.3 (M+H)+.

EXAMPLE 6

Analogously to Example 5, from (S)-3-[allyl-[3-[(S)-1-(amino-imino-methyl)piperidin-3-ylmethyl-carbamoyl]-2-(naphthalene-2-sulfonylamino)propionyl]amino]propionic acid (Example 4.l), there is obtained 3-[(S)-3-[(S)-1-(amino-imino-methyl)piperidin-3-ylmethylcarbamoyl]-2-(naphthalene-2-sulfonylamino)propionyl]propylamino]propionic acid, MS (ion spray): 575.2 (M+H)+.

EXAMPLE 7

A) The following esters are obtained analogously to Example 1 from the diesters of Examples 2.B) i) and j) on the one hand and from rac-2-aminomethyl-4-morpholinecarboxamidine trifluoroacetate in place of (S)-1-amindino-3-(aminomethyl)piperidine dihydrochloride on the other hand:

a) ethyl 3-[N-[(S)-3-[(R,S)-4-(amino-imino-methyl)-morpholin-2-ylmethylacarbamoyl]-2-(naphthalene-2-sulfonylamino)-propionyl]cyclopropylamino]-propionate trifluoroacetate (1:1), MS (ion spray): 603.4 (M+H)+, b) ethyl 3-[N-allyl-[(S)-3-(R,S)-4-(amino-imino-methyl)- morpholin-2-ylmethylcarbamoyl]-2-(naphthalene-2-sulfonylamino)propionyl]-amino]-propionate trifluoroacetate (1:1), MS (ion spray): 603.5 (M+H)+.

B) The trifluoroacetate starting material is prepared as follows:

a) A solution of 23.3 g of rac-2-(aminomethyl)-4-benzylmorpholine in 250ml of dioxane is treated with 27.1 g of di-t-butyl dicarbonate in 250 ml of dioxane. After stirring, the solvent is evaporated and the residue is chromatographed on silica gel with methylene chloride-ethyl acetate 3:1. The product is recrystallized from methylene chloride-hexane. There are obtained 25.6 g of t-butyl rac-[(4-benzyl-2-morpholinyl)methyl]-carbamate.

b) A solution of the product from a) in 500 ml of ethyl acetate and 50 ml of acetic acid is treated with 2.6 g of Pd/C and hydrogenated under normal conditions for 5 hours. After filtration and evaporation, the residue is dissolved in 230 ml of DMF, treated with 46 ml of triethylamine and 10.8 g of formamidinesulfonic acid. After stirring, the reaction mixture is evaporated and the residue is partitioned between ethyl acetate and water. After drying the organic phase and evaporation, there is obtained t-butyl rac-[(4-amidino-2-morpholinyl)methyl]carbamate hemisulfite.

c) 6.5 g of the material obtained under b) are suspended in 50 ml of methylene chloride and treated at 0° with 20 ml of TFA. Then, the reaction mixture is evaporated and azeotroped with ethylene chloride and toluene. Rac-2-(aminomethyl)-4-morpholinecarboxamidine trifluoroacetate is isolated.

EXAMPLE 8

The following acids are obtained analogously to Example 3 from the esters of Example 7:

a) 3-[(S)-3-[(R,S)-4-Amino-imino-methylmorpholin-2-ylmethylcarbamoyl]-2-(naphthalene-2-sulfonylamino)-N-cyclopropylpropionylamino]-propionic acid, MS (ion spray): 575.5 (M+H)+, b ) 3-[N-allyl-[(S)-3-[(R,S)-4-(amino-imino-methyl)-morpholin-2-ylmethylcarbamoyl]-2-(naphthalene-2-sulfonylamino)-propionyl]-amino-propionic acid, MS (ion spray): 575.4 (M+H)+.

EXAMPLE 9

A solution of 1.4 g of N-[3-(t-butoxycarbonyl)-N-(2-naphthylsulfonyl)-L-alanyl]-N-cyclopropyl-β-alanine ethyl ester (Example 2B)j)9) in 23 ml of methylene chloride is treated at 2° with 4.1 ml of trifluoroacetic acid. After stirring at room temperature for 5 hours, the solution is evaporated. The residue is dissolved in 23 ml of DMF, treated with 1.7 ml of 4-ethylmorpholine, 1.2 g of BOP and 0.8 g of rac-3-[[(2-hdyroxyethyl)amino]-methyl]1-piperidinecarboxamidine dihydrochloride. After stirring, the reaction solution is evaporated and the residue is chromatographed on a RP-18 column with water-acetonitrile. There is obtained 0.7 g of ethyl 3-[(S)-3-[(R,S)-N-(1-amino-imino-methyl-piperidin-3-ylmethyl)-2-hydroxy-ethylcarbamoyl]-2-(naphthalene-2-sulfonylamino)-N-cyclopropyl-propionylamino]-propionate hydrochloride (1:1) MS (ion spray): 645.5 (M+H)+.

Preparation of the piperidinecarboxamidine starting material:

a) 31.6 g of di-t-butyl dicarbonate in 100 ml of dioxane are added to a solution of 20 g of N-(2-hydroxyethyl)-3-picolylamine in 250 ml of dioxane. After stirring the reaction mixture is evaporated and the residue is chromatographed on silica gel with ethyl acetate. There are obtained 29.8 g of t-butyl (2-hydroxyethyl)(3-pyridylmethyl)carbamate, EI-MS: 253 (M+H)+.

b) The material obtained under a) is dissolved in 150 ml of ethanol, treated with 3 g of ruthenium on aluminum oxide and hydrogenated for 24 hours at 60° and under 100 bar. After filtration, there is obtained quantitatively t-butyl rac-(2-hydroxyethyl)-(3-piperidinylmethyl)-carbamate, EI-MS: 259 (M+H)+.

c) A solution of the product from b) in 500 ml of DMF is treated with 51 ml of triethylamine and 12.1 g of formamidinesulfonic acid. After stirring, the precipitated material is filtered, dissolved in ethanol-water 1:1, filtered and the filtrate is evaporated and azeotroped with ethanol. The residue is suspended with ether and filtered under suction. There are obtained 24.1 g of t-butyl rac-[(1-amidino-3-piperidinyl)methyl](2-hydroxyethyl)-carbamate hemisulfite, Fab-MS: 301 (M+H).

d) 10.0 g of the product obtained under c) are dissolved in 90 ml of methylene chloride and 10 ml of methanol, treated at 0° with 100 ml of a 4 molar hydrochloric acid solution in ethyl acetate. After stirring, the reaction mixture is evaporated, There is obtained quantitatively rac-3-[[(2-hydroxyethyl)amino]methyl]-1-piperidinecarboxamidine dihydrochloride, Fab-MS: 201 (M+H)+.

EXAMPLE 10

(S)-N4-[R,S)-1-Amino-imino-methyl-piperidin-3-ylmethyl]-N1-(2-carboxyethyl)-N1-cyclopropyl-N4-(2-hydroxyethyl)-2-(naphthalen-2-ylsulfonylamino)-succinamide, MS (ion spray): 617.5 (M+H)+, is obtained analogously to Example 3 from the ester of Example 9.

EXAMPLE 11

A solution of 0.45 g of t-butyl (S)-hexahydro-β-(2-naphthylsulfonamido)-γ-oxo-1H-azepine-1-butyrate in 3 ml of methylene chloride is treated at 0° with 1.5 ml of trifluoroacetic acid. After stirring, the solution is evaporated, azeotroped with toluene and dried. The residue is dissolved in 8 ml of DMF, treated with 0.38 ml of 4-ethylmorpholine, 0.49 g of BOP and 0.3 g of rac-3-[[(2-hydroxyethyl)amino]methyl]-1-piperidinecarboxamidine dihydrochloride (Ex. 9d). After stirring, the reaction mixture is evaporated and chromatographed on silica gel with ethyl acetate-acetone-acetic acid-water (6:2:1:1). The product-containing fractions are evaporated and the residue is filtered over Dowex (acetate form) with methanol-water (9:1). There is obtained 0.4 g of (S)-N-[[(RS)-1-amidino-3-piperidinyl]methyl]-N-(2-hydroxyethyl)hexahydro-β-2 -naphthylsulfonamido-1H-1-azepinebutyramide diacetate, MS (ion spray): 587.2 (M+H)+.

Preparation of the starting material:

a) 1.37 ml of hexamethyleneimine, 2.3 g of N-(dimethylaminopropyl)-N′-ethylcarbodiimide hydrochloride and 122mg of dimethylaminopyridine are added to a solution of 2.89 g of N-Boc-L-aspartic acid β-t-butyl ester in 50 ml of methylene chloride. After stirring, the reaction mixture is poured into ice-cold 5% potassium hydrogen sulfate-10% potassium sulfate solution and extracted with methylene chloride. The organic phase is washed with water, then dried and evaporated. The residue is chromatographed on silica gel with hexane-ethyl acetate. There are obtained 2.9 g of t-butyl (S)-[β-(1-t-butoxyformamido)hexahydro-γ-oxo-1H-azepine-1-butyrate, Fab-MS: 371.2 (M+H)+.

b) A solution of 1.02 g of the product from a) in 10 ml of dioxane is treated with 1.31 g of p-toluenesulfonic acid monohydrate. After stirring, there are added in succession while cooling with ice, 6.9 ml of 1N sodium hydroxide solution, a solution of 0.93 g of 2-naphthyl sulfochloride in 5 ml of dioxane and 0.7 g of sodium bicarbonate. After stirring the reaction mixture is poured into ice-cold 5% potassium hydrogen sulfate-10% potassium sulfate solution and extracted with ethyl acetate. The organic phase is washed with water, then dried and evaporated. After chromatography on silica gel with hexane-ethyl acetate (2:1), there is isolated 0.55 g of t-butyl (S)-hexahydro-β-(2-naphthylsulfonamido)-γ-oxo-1H-azepine-1-butyrate, MS (ion spray): 483.1 (M+H)+.

EXAMPLE 12

1.3 g of p-toluenesulfonic acid monohydrate are added to a solution of 1.9 g of t-butyl (S)-3-[N-[(S)-4-(azepan-1-yl)-3-(naphthalene-2-sulfonylamino)-4-oxobutyryl]-N-ethoxycarbonylmethylaminomethyl]-piperidine- 1-carboxylate. After stirring, the solution is evaporated. The residue is dried, dissolved in 25 ml of DMF and treated with 1.9 ml of triethylamine and 450 mg of formamidinesulfonic acid. After stirring, the reaction mixture is evaporated and the residue is chromatographed on a RP-18 column with a water-acetonitrile mixture. There is obtained 0.7 g of ethyl [[(R)-1-(amino-imino-methyl)-piperidin-3-ylmethyl]-[(S)-4-(azepan-1-yl)-3-(naphthyl-2-sulfonylamino)-4-oxobutyryl]amino]acetate hemisulfite, MS (ion spray): 629.2 (M+H)+.

Preparation of the ester Starting material:

a) A solution of 211.2 g of di-t-butyl dicarbonate in 500 ml of dioxane is added to a solution of 92.9 g of rac-3-hydroxymethylpiperidine in 1500 ml of dioxane in such a manner that the temperature does not exceed 25° C. The reaction mixture is stirred and then evaporated. The residue is suspended in 800 ml of hexane and filtered. There are obtained 120.7 g of rac-n-t-butyloxycarbonyl-3-hydroxymethylpiperidine, m.p. 78° C.

b) A solution of 100 g of the product from a) in 4000 ml of methylene chloride is treated with 56.2 ml of pyridine and cooled to 0° C. 58.3 ml of butyryl chloride are added dropwise thereto in such a manner that the temperature does not exceed 10° C. After stirring, the suspension is filtered. The filtrate is evaporated and the residue is taken up in ethyl acetate. The organic phase is washed with aqueous 10% $CuSO_4$ solution, dried and evaporated. The residue is filtered through silica gel and eluted with hexane-ethyl acetate (8:2). There are obtained 119.7 g of t-butyl rac-3-(butyroxymethyl)-1-piperidinecarboxylate.

c) 116.6 g of the product from b) are emulsified in 2 l of 0.1M sodium chloride solution and 80 ml of 0.1M sodium phosphate buffer pH 7.0. The pH is adjusted to 7.0 with 1.0N sodium hydroxide solution and the reaction is started by the addition of 1.00 g of lipoprotein lipase (Lipase P-30. Amano) obtained from *Pseudomonas fluorescens* in 10 ml of 0.1M sodium chloride solution. The pH is held at 7.0 by the addition of 2.0N sodium hydroxide solution while stirring. After 14 hours, the reaction is terminated by the addition of 500 ml of methylene chloride. The reaction mixture is then extracted with methylene chloride and the organic phase is dried and evaporated. Chromatography of the residue over silica gel with hexane-ethyl acetate gives 36.6 g of t-butyl (S)-3-hydroxymethyl-1-piperidinecarboxylate, m.p. 89°–90° C. $[\alpha]_{365}^{25} = +53.5°$ (c=1.0, EtOH).

d) The 65.7 g ester fraction from c) is emulsified in 1.15 l of 0.1M sodium chloride solution and 45 ml of 0.1M sodium phosphate buffer (pH 7.0) and treated with 0.50 g of Lipase P-30 in 5 ml of 0.1M sodium chloride solution. The pH is held at 7.0 by the addition of 2.0N sodium hydroxide solution while stirring. After 40 hours, the reaction is terminated by the addition of 400 ml of methylene chloride. The reaction mixture is extracted with methylene chloride and the organic phase is dried and evaporated. Chromatography of the residue over silica gel with hexane-ethyl acetate gives 49.5 g of t-butyl (R)-3-(butyryloxymethyl)-1-piperidinecarboxylate. This is dissolved in 250 ml of ethanol, treated with 88 ml of 2N sodium hydroxide solution, stirred overnight and then evaporated. The residue is taken up in 200 ml of methylene chloride and washed with water. The aqueous phase is extracted with methylene chloride and the organic phase is dried and concentrated. Chromatography of the residue over silica gel with hexane-ethyl acetate gives 33.7 g of t-butyl (R)-3-hydroxymethyl-1-piperidinecarboxylate, $[\alpha]_{365}^{25} = -60.7°$ (c=1.0, EtOH).

e) A solution of 5.0 g of the product from d) in 100 ml of pyridine is treated with 5.4 g of p-chlorosulfonyl chloride. The reaction mixture is stirred, then evaporated, taken up 200 ml of ethyl acetate and washed with water and aqueous 10% CuSO4 solution. The organic phase is dried and evaporated. The residue is filtered over silica gel and eluted with hexane-ethyl acetate (8:2). There are obtained 6.5 g of t-butyl (R)-3-(p-chlorophenylsulfonyloxymethyl)-1-piperidinecarboxylate.

f) A solution of the product from e) in 50 ml of DMF is treated with 3.25 g of sodium azide. The reaction mixture is stirred at 50° C. for 15 hours and evaporated. The residue is taken up in water and ether and washed with water. The ether phase is dried and evaporated. 4.0g of t-butyl (R)-3-azidomethyl-1-piperidinecarboxylate are obtained.

g)1) A solution of the product from f) in 100 ml of ethanol is hydrogenated under 1 bar of hydrogen in the presence of 0.6 g of platinum oxide. Then, the reaction mixture is filtered over silica gel and eluted with methanol. There are obtained 3.4 g of t-butyl (S)-3aminomethyl-1-piperidinecarboxylate, $[\alpha]_D^{25} = 17.7°$ (c=0.6 EtOH).

g)2) Analogously to e), f) and g)1), from t-butyl (S)-3-hydroxymethyl-1-piperidinecarboxylate there is obtained t-butyl (R)-3-aminomethyl-1-piperidinecarboxylate, $[\alpha]_D^{25} = +23.0°$ (c=0.4, EtOH).

h) A solution of 4.0 g of the product from g) in 300 ml of methylene chloride is treated under argon with 9.6 ml of Hünig base and 2.08 ml of ethyl bromoacetate. After stirring, the solution is evaporated. The residue is suspended in ethyl acetate, filtered and the filtrate is extracted with water. The organic phase is dried, evaporated and the residue is chromatographed on silica gel with hexane-ethyl acetate (1:1). There are obtained 2.3 g of N-[[(S)-1-t-butoxycarbonyl)-3-piperidinyl]methyl]glycine ethyl ester, EI-MS: 243 (M-t-butyl).

i) A solution of 1.65 g of t-butyl (S)-hexahydro-β-(2-naphthylsulfonamido)-γ-oxo-1H-azepine-1-butyrate (Example 11b) in 50ml of methylene chloride is treated at 0° C. with 5.5 ml of trifluoroacetic acid. After stirring the mixture is evaporated. The residue is dissolved in 31 ml of DMF, treated with 2.3 ml of 4-ethylmorpholine, 1.60 g of BOP and a solution of 1.3 g of the product from h) in 2 ml of DMF. After stirring, the reaction mixture is evaporated. The residue is taken up in ethyl acetate and extracted with water. After drying the organic phase, evaporation and chromatography of the residue on silica gel with hexane-ethyl acetate, there are obtained 2.0 g of t-butyl (S)-3-[N-[(S)-4-(azepan-1-yl)-3-(naphthalene-2-sulfonylamino)-4-oxobutyryl]-N-ethoxycarbonylmethylaminomethyl]-piperidine-1-carboxylate, MS (ion spray): 687.3 (M+H)+.

EXAMPLE 13

A solution of 1.0 g of the ester product from Example 12 in 10 ml of methanol is treated with 9.0ml of 1N sodium hydroxide solution. After stirring, 9.0 ml of 1N hydrochloric acid are added. The solution is evaporated, the residue is chromatographed on a RP-18 column with water-acetonitrile and there is thus obtained 0.5 g of [[(R)-1-(amino-imino-methyl)piperidin-3-ylmethyl]-[(S)-4-(azepan-1-yl)-3-(naphthyl-2-sulfonylamino)-4-oxo-butyryl]aminolacetic acid, MS (ion spray): 601.2 (M+H)+.

EXAMPLE 14

A) Analogously to Example 1 there are obtained:
a) from t-butyl (S)-N-cyclopropyl-N-ethoxycarbonylmethyl-3-(4-trifluoromethyl-phenylsulfonylamino)-succinamate,
ethyl [(S)-3-[(S)-1-(amino-imino-methyl)piperidin-3-ylmethylcarbamoyl]-2-(4-trifluoromethyl-phenylsulfonyl- amino)propionyl-cyclopropylamino]-acetate (1:1), MS (ion-spray): 605.4 (M+H)+,
b) from t-butyl (S)-3-(4-t-butyl-phenylsulfonylamino)-N- cyclopropyl-N-ethoxycarbonylmethyl-succinamate,
ethyl [(S)-3-[(S)-1-(amino-imino-methyl)piperidin-3-ylmethylcarbamoyl]-2-(4-t-butylphenylsulfonylamino)-propionylcyclopropyl-amino]acetate (1:1), MS (ion spray): 593.5 (M+H)+, c) from t-butyl (S)-3-(biphenyl-4-ylsulfonylamino)-N-cyclo- propyl-N-ethoxycarbonylmethyl-succinamate, ethyl (S)-3-[(S)-1-(amino-imino-methyl)piperidin-3-ylmethylcarbamoyl]-2-(biphenyl-4-ylsulfonylamino)-N-cyclopropylpropionylaminoacetate hydrochloride (1:2), MS (ion spray): 613.4 (M+H)+, d) from t-butyl (S)-N-cyclopropyl-N-ethoxycarbonylmethyl-3-(3-methylquinolin-8-yl-sulfonylamino)-succinamate, ethyl (S)-3-[(S)-1-(amino-imino-methyl)piperidin-3-ylmethylcarbamoyl]-N-cyclopropyl-2-(3-methylquinolin-8-ylsulfonylamino)- propionylamino-acetate (1:1), MS (ion spray): 602.2 (M+H)+.

B) The diester starting material is obtained from t-butyl-(S)-2-(1-t-butoxyformamido)-N-cyclopropyl-N-[(ethoxycarbonyl)methyl]succinamate (Example 2B)c)1), analogously to Example 1b), but using the corresponding arylsulfochlorides in place of β-naphthylsulfochloride:

a) t-butyl (S)-N-Cyclopropyl-N-ethoxycarbonylmethyl-3-(4-trifluoromethyl-phenylsulfonylamino)-succinamate, MS (ion spray): 523.0 (M+H)+, b) t-butyl (S)-3-(4-t-butyl-phenylsulfonylamino)-N-cyclopropyl-N-ethoxycarbonylmethyl-succinamate, MS (ion spray): 511.1 (M+H)+, c) t-butyl (S)-3-(biphenyl-4-ylsulfonylamino)-N-cyclopropyl-N-ethoxycarbonylmethyl-succinamate, MS (ion spray): 531.4 (M+H)+, d) t-butyl (S)-N-cyclopropyl-N-ethoxycarbonylmethyl-3-(3-methylquinolin-8-yl-sulfonylamino)-succinamate, MS (ion spray): 520.2 (M+H)+.

EXAMPLE 15

The following acids are obtained analogously to Example 3 from the esters of Example 14A):

a) [(S)-3-[(S)-1-(Amino-imino-methyl)piperidin-3-ylmethylcarbamoyl]-2-(4-trifluormethyl-phenylsulfonylamino)-propionylcyclopropyl-amino]acetic acid, MS (ion spray): 577.4 (M+H)+, b) [(S)-3-[(S)-1-(amino-imino-methyl)piperidin-3-ylmethylcarbamoyl]-2-(4-t-butylphenylsulfonylamino)-propionylcyclopropyl-amino]-acetic acid, MS (ion spray): 565.2 (M+H)+, c) (S)-3-[(S)-1-(amino-imino-methyl)piperidin-3-ylmethylcarbamoyl]-2-(biphenyl-4-ylsulfonylamino)-N-cyclopropylpropionylamino-acetic acid, MS (ion spray): 585.4 (M+H)+, d) (S)-3-[(S)-1-(amino-imino-methyl)piperidin-3-ylmethylcarbamoyl]-N-cyclopropyl-2-(3-methylquinolin-8-ylsulfonylamino)propionylamino-acetic acid, MS (ion spray): 574.4 (M+H)+.

EXAMPLE 16

A solution of 0.34 g of the product from Example 15A)d) in 25 ml of ethanol is treated with 1 ml of acetic acid and 0.1 g of Pd/C and hydrogenated under normal conditions. After filtration and evaporation of the filtrate, there is obtained 0.12 g of N-[(S)-3-[(S)-1-(amino-imino-methyl)piperidin-3-ylmethylcarbamoyl]-2-(3-methyl-1,2,3,4-tetrahydroquinolin-8-ylsulfonylamino)-propionyl]-N-cyclopropyl-aminoacetic acid acetate (1:1), MS (ion spray): 578.4 (M+H)+.

EXAMPLE 17

Analogously to Example 1, from t-butyl (S)-N-cyclopropyl-3-(naphthalen-2-ylsulfonylamino)-N-(3-oxobutyl)-succinamate there is obtained, (S)-N4-[(S)-1-(amino-imino-methyl)piperidin-3-ylmethyl]-N1-cyclopropyl-2-(naphthalen-2-ylsulfonylamino)-N1-(3-oxobutyl)-succinamide hydrochloride (1:1), MS (ion spray): 571.2 (M+H)+.

Preparation of the starting material:

a) A solution of 13.9 g of di-t-butyl dicarbonate in 140 ml of dioxane is added dropwise while cooling to a solution of 10 g of N-cyclopropyl-β-alanine ethyl ester in 100 ml of dioxane. After stirring, the reaction mixture is evaporated. After drying the residue, there are obtained 16 g of ethyl 3-(t-butoxycarbonyl- cyclopropyl-amino)propionate, Fab-MS: 201 (M-isobutylene).

b) 42 ml of a 1.6 molar methyllithium solution in ether are added dropwise at 0°–3° to a solution of 15.7 g of the product from a) in 160 ml of THF. After stirring at room temperature, the mixture is cooled to 0° and an additional 34.5 ml of a 1.6 molar methyllithium solution in ether are added dropwise. After stirring, the reaction solution is poured into ice-cold 5% potassium hydrogen sulfate-10% potassium sulfate solution and extracted with ethyl acetate. The organic phase is washed with sodium chloride solution, then dried and evaporated and the residue is chromatographed on silica gel with hexane-ethyl acetate 4:1. In a first fraction there are obtained 8.3 g of t-butyl cyclopropyl-(3-hydroxy-3-methylbutyl) carbamidate, Fab-MS: 187 (M-isobutylene).

c) From the chromatogram of b), there are isolated in a second fraction 1.7 g of t-butyl cyclopropyl-3-oxobutyl-carbamidate, Fab-MS: 171 (M-isobutylene).

d) A solution of 18.2 g of the product from b) in 80 ml of ethyl acetate is treated with 40 ml of a 4 molar hydrochloric acid solution in ethyl acetate. After stirring, the precipitated material is filtered and washed with ethyl acetate. After drying there are obtained 3.6 g of 4-cyclopropylamino-2-methylbutan-2-ol hydrochloride, Fab-MS: 143 M+.

e) A solution of 3.1 g of the product from c) in 30 ml of ethyl acetate is treated with 30 ml of a 4 molar hydrochloric acid solution in ethyl acetate. After stirring, the mixture is evaporated and dried. There are obtained 2.3 g of 4-cyclopropylamino-butan-2-one.

f) A solution of 3.9 g of N-Boc-L-aspartic acid β-t-butyl ester in 40 ml of methylene chloride is treated with 5.5 ml of 4-ethylmorpholine, 3.1 g of N-(dimethylaminopropyl)-N′-ethylcarbodiimide hydrochloride and 0.17 g of 4-dimethylaminopyridine. The material obtained under e), dissolved in 20 ml of methylene chloride, is added to this solution. After stirring, the reaction solution is poured into ice-cold 5% potassium hydrogen sulfate-10% potassium sulfate and extracted with methylene chloride. The organic phase is washed with sodium chloride solution, then dried and evaporated, and the residue is chromatographed on silica gel with hexane-methyl acetate 2:1. There are obtained 3.7 g of t-butyl (S)-N-(2-acetylethyl)-3-t-butoxycarbonylamino-N-cyclopropyl-succinamate, MS (ion spray): 399.3 (M+H)+.

g) From the product of f), there is obtained in analogy to Example 2.B)i) t-butyl (S)-N-cyclopropyl-3-(naphthalen-2-ylsulfonylamino)-N-(3-oxo-butyl)-succinamate, Fab-MS: 433 (M-isobutylene).

EXAMPLE 18

Analogously to Example 17, from 4-cyclopropylamino-2-methylbutan-2-ol hydrochloride (Example 17d) via
a) t-butyl (S)-3-t-butoxycarbonylamino-N-cyclopropyl-N-(3-hydroxy-3-methylbutyl)-succinamate, MS (ion spray): 415.4 (M+H)+, and
b) t-butyl (S)-N-cyclopropyl-N-(3-hydroxy-3-methyl-butyl)-2-naphthalene-2-sulfonylamino)-succinamate, MS (ion spray): 505.3 (M+H)+, there is obtained
(S)-N4-[(S)-1-(amino-imino-methyl)-piperidin-3-ylmethyl-N1-cyclopropyl-N1-(3-hydroxy-3-methyl-butyl)-2-(naphthalen-2-ylsulfonylamino)-succinamide hydrochloride (1:1), MS (ion spray): 587.4 (M+H)+.

EXAMPLE 19

The following esters are obtained analogously to Example 7A), but starting from the diesters of Example 14B)a), b) and, respectively, c):
a) Ethyl [(S)-3-[(R,S)-4-(amino-imino-methyl)morpholin-2-ylmethylcarbamoyl]-2-(4-trifluoromethyl-phenylsulfonylamino)propionyl-cyclopropyl-amino]-acetate (1:1), MS (ion spray): 607.2 (M+H)+,
b) ethyl [(S)-3-[(R,S)-4-amino-imino-methyl)morpholin-2-ylmethylcarbamoyl]-2-(4-t-butyl-phenylsulfonylamino)-propionylcyclopropyl-amino]-acetate trifluoroacetate (1:1), MS (ion spray): 595.3 (M+H)+, and, respectively.
c) ethyl [(S)-3-[(R,S)-4-(amino-imino-methyl)morpholin-2-ylmethylcarbamoyl]-2-(biphenyl-4-ylsulfonylamino)-N-cyclopropylpropionylamino]acetate trifluoroacetate (1:1), MS (ion spray): 615.3 (M+H)+.

EXAMPLE 20

The following acids are obtained analogously to Example 3 starting from the esters of Example 19:
a) [(S)-3-[(R,S)-4-(Amino-imino-methyl)morpholin-2-ylmethylcarbamoyl]-2-(4-trifluoromethyl-phenylsulfonylamino)-propionylcyclopropyl-amino]-acetic acid, MS (ion spray): 579.1 (M+H)+,
b) [(S)-3-[(R,S)-4-(amino-imino-methyl)morpholin-2-ylmethylcarbamoyl]-2-(t-butyl-phenylsulfonylamino)-N-cyclopropyl-propionylamino]acetic acid, MS (ion spray): 567.4 (M+H)+,
c) [(S)-3-[(R,S)-4-(amino-imino-methyl)-morpholin-2-ylmethylcarbamoyl]-2-(biphenyl-4-ylsulfonylamino)-N-cyclopropylpropionylaminolacetic acid, MS (ion spray): 587.3 (M+H)+.

EXAMPLE 21

Analogously to Example 9, but starting from N-methyl-3-picolylamine in place of N-(2-hydroxyethyl)-3-picolylamine, there is obtained via
t-butylmethyl (3-pyridinylmethyl)carbamate,
t-butyl-rac-methyl (3-piperidinylmethyl)carbamate,
t-butyl-rac-[(1-amidino-3-piperidinyl)methyl]methyl-carbamate bisulfite and
rac-3-[(methylamino)methyl]-1-piperidincarboxamidine dihydrochloride, Fab-MS: 171 (M+H)+, a) using
t-butyl (S)-N-butyl-N-(2-ethoxycarbonylethyl-3-(naphthalen-2-ylsulfonylaminesuccinamate (Example 2.B )jj)11),
ethyl 3-[(S)-3-[(R,S)-[1-(amino-imino-methyl)piperidin-3-ylmethyl]-N-methylcarbamoyl]-N-butyl-2-(naphthalen-2-ylsulfonylamino)propionylamino]-propionate hydrochloride (1:1), MS (ion spray): 631.5 (M+H)+,
b) using
N-[3-(t-butoxycarbonyl)-N-(2-naphthylsulfonyl)-L-alanyl]-N-cyclopropyl-β-alanine (Example 2.B)jj)9),
ethyl 3-[[(S)-3-[[(R,S)-1-(amino-imino-methyl)-piperidin-3-ylmethyl)]-methylcarbamoyl]-2-(naphthalene-2-sulfonylamino)propionyl]-cyclopropylamino]-propionate hydrochloride (1:1), MS (ion spray): 615.4 (M+H)+.

EXAMPLE 22

The following acids are obtained analogously to Example 3 from the esters of Example 21:
a) 3-[(S)-3-[(R,S)-[1-(Amino-imino-methyl)piperidin-3-ylmethyl]-N-methyl-carbamoyl]-N-butyl-2-(naphthalen-2-ylsulfonylamino)propionylamino]-propionic acid, MS (ion spray): 603.5 (M+H)+,
b) 3-[[(S)-3-[[(R,S)-2-(amino-imino-methyl)piperidin-3-ylmethyl]-methyl-carbamoyl]-2-(naphthalene-2-sulfonylamino)propionyl]-cyclopropyl-amino]-propionic acid, MS (ion spray): 587.4 (M+H)+.

EXAMPLE 23

A solution of t-butyl (S)-3-[(S)-3-[(4-chlorobenzyl)-methoxycarbonylmethylcarbamoyl]-3-(naphthalene-2-sulfonylamino)propionylaminomethylpiperidine-1-carboxylate in 20 ml of methylene chloride is treated with 4 ml of trifluoroacetic acid. After stirring, the mixture is evaporated, the residue is dissolved in 2.7 ml of methanol and treated with 0.93 ml of triethylamine and 330 mg of formamidesulfonic acid. Then, an additional 165 mg of formamidinesulfonic acid and 0.19 ml of triethylamine are added. After stirring, the reaction mixture is concentrated and the residue is chromatographed on silica gel with ethyl acetate-acetone-acetic acid-water 6:2:1:1. There are obtained 516 mg of N-[N4-[[(S)-1-amidino-3-piperidinyl]methyl]-N2-(2-naphthylsulfonyl)-L-asparaginyl]-N-(p-chlorobenzyl)glycine methyl ester acetate (1:1), MS (ion spray): 657 (M+H)+.

Preparation of the starting material:
a) 52.85 ml of 2N sodium hydroxide solution are added dropwise to a suspension of 10 g of L-aspartic acid β-t-butyl ester and 11.98 g of naphthalene-2-sulfochloride in 100 ml of dioxane. After stirring, 53 ml of 1N hydrochloric acid are added dropwise. The reaction mixture is taken up in 800 ml of ether and the ether/dioxane phase is washed with water. After drying and evaporation of the organic phase the residue is crystallized in ether. After filtering the crystals, there are obtained 13.7 g of N-(2-naphthylsulfonyl)-L-aspartic acid 4-t-butyl ester, m.p. 141°.
b) 22.2 ml of triethylamine are added dropwise to 20 g of glycine methyl ester hydrochloride and 34.8 g of di-t-butyl dicarbonate in 300 ml of methylene chloride and 10 ml of water. After stirring, the reaction mixture is concentrated. The residue is taken up in ether and the ether phase is washed neutral with water after the addition of 5 ml of 1N hydrochloric acid. After drying and evaporating the ether phase, there are obtained 30.2 g of N-BOC-glycine methyl ester. Rf=0.33 (ether/hexane 1:1).

c) 242 mg of sodium hydride (55% in oil) are added to 1.0 g of the crude product from b) and 937 mg of 4-chloro-benzyl chloride in 10 ml of DMF while cooling with ice. After stirring, the reaction mixture is taken up in 100 ml of ether and washed with water. After drying and evaporating the ether phase, the residue is chromatographed over silica gel with ether/hexane 1:2. There are obtained 1.27 g of N-BOC-N-(4-chlorobenzyl)-glycine methyl ester Rf=0.33 (ether/hexane 1:2).

d) 1.275 g of the product from c) are treated with 5 ml of 10N hydrochloric acid in methanol. The methanol is evaporated and the residue is suspended in 20 ml of ether and filtered. After washing the residue with ether, there is obtained 0.93 g of N-(4-chlorobenzyl)-glycine methyl ester hydrochloride, Rf=0.59 (ethyl acetate/acetone/water/glacial acetic acid 6:2:1: 1).

e) 567 mg of the product from a), 394 mg of the product from d), 636 mg of BOP and 0.5 ml of Hünig base are dissolved in 8 ml of methylene chloride. After stirring, the reaction mixture is taken up 100 ml of ether and the ether phase is washed with hydrochloric acid and water. After drying and evaporating the ether phase, the residue is chromatographed over silica gel with ether/hexane 2:1. There are obtained 926 mg of t-butyl (S)-N-(4-chlorobenzyl)-N-methoxycarbonylmethyl-3-(naphthalene-2-sulfonylamino)succinamate, MS (ion spray): 575 (M+).

f) 926 mg of the product frown e) are treated with 6 ml of 5 molar hydrochloric acid in dioxane. After stirring, the reaction mixture is taken up in 100 ml of ether and the ether phase is washed with water. After drying and evaporation, there are obtained 877 mg of (S)-N-(4-chlorobenzyl)-N-methoxycarbonylmethyl-3-(naphthalene-2-sulfonylamino)-succinamic acid, Rf=0.7 (ethyl acetate/glacial acid 99:1).

g) 877 mg of the product from f), 435 mg of t-butyl [S]-3-aminomethyl-1-piperidinecarboxylate, 785 mg of BOP and 0.58 ml of Hünig base are stirred in 12 ml of methylene chloride. The reaction mixture is taken up in 100 ml of ether and the ether phase is washed with 1N hydrochloric acid and water. After drying and evaporating the ether phase, the residue is chromatographed over silica gel with ethyl acetate-hexane 4:1. There are obtained 951 mg of t-butyl (S)-3-[(S)-3[(4-chlorobenzyl)omethoxycarbonylmethylcarbamoyl]-3-(naphthalene-2-sulfonylamino)-propionylaminomethyl]piperidine-1-carboxylate, MS (ion spray): 715 (M+H)+.

EXAMPLE 24

A solution of 300 mg of the ester product from Example 23 in 3 ml of THF is treated with 1.25 ml of 1N LiOH. After stirring and adding 2 ml of acetic acid, the mixture is evaporated and the residue is chromatographed on silica gel with ethyl acetate-acetone-acetic acid-water 6:2:1:1. There are obtained 154.5 mg of N-[N4-[[(S)-1-amidino-3-piperidinyl]methyl]-N2-(2-naphthylsulfonyl)-L-asparaginyl]-N-(p-chlorobenzyl)glycine, MS (ion spray): 641 (M−H)−.

EXAMPLE 25

The following esters are prepared analogously to Example 23:
a) N-N4-[[(S)-1-amidino-3-piperidinyl]methyl]-N2-(2-naphthylsulfonyl)-L-asparaginyl]-N-(m-chlorobenzyl)glycine methyl ester acetate (1:1), MS (ion spray): 657 (M+H)+,
b) N-N4-[[(S)-1-amidino-3-piperidinyl]methyl]-N2-(2-naphthylsulfonyl)-L-asparaginyl]-N-(o-chlorobenzyl)glycine methyl ester acetate (1:1), MS (ion spray): 657 (M+H)+,
c) methyl [N-[(S)-3-[(S)-1-amidino-piperidin-3-yl-methylcarbamoyl]-2-(naphthalene-2-sulfonylamino)-propionyl]-N-(4-methoxybenzyl)-amino]-acetate acetate (1:1), MS (ion spray): 653 (M+H)+,
d) methyl [N-[(S)-3-[(S)-1-amidino-piperidin-3-yl-methylcarbamoyl]-2-(naphthalene-2-sulfonylamino)-propionyl]-N-(pyridin-2ylmethyl)-amino]-acetate acetate (1:2), MS (ion spray): 624 (M+H)+,
e) methyl [[(S)-3-[(S)-1-(amino-imino-methyl)-piperidin-3-ylmethylcarbamoyl]-2-(naphthalene-2-sulfonylamino)-propionyl]-(3-methoxy-benzyl)-amino]-acetate acetate (1:1), MS (ion spray): 653 (M+H)+.

EXAMPLE 26

The following acids are obtained analogously to Example 24 from the esters of Example 25:
a) N-[N4-[[(S)-1-Amidino-3-piperidinyl]methyl]-N2-(2-naphthylsulfonyl)-L-asparaginyl]-N-(m-chlorobenzyl)glycine, MS (ion spray): 641 (M−H)−,
b) N-[N4-[[(S)-1-Amidino-3-piperidinyl]methyl]-N2-(2-naphthylsulfonyl)-L-asparaginyl]-N-(o-chlorobenzyl)glycine, MS (ion spray): 641 (M−H)−,
c) [N-[(S)-3-[(S)-1-amidino-piperidin-3-yl-methylcarbamoyl]-2-(naphthalene-2-sulfonylamino)-propionyl]-N-(4-methoxybenzyl)amino]acetic acid, MS (ion spray): 639 (M+H)+,
d) [N-[(S)-3-[(S)-1-amidino-piperidin-3-yl-methylcarbamoyl]-2-(naphthalene-2-sulfonylamino)-propionyl]-N-(pyridin-2-ylmethyl)amino]acetic acid acetate, MS (ion spray): 610 (M+H)+,
e) [[(S)-3-[(S)-1-(amino-imino-methyl)piperidin-3-ylmethylcarbamoyl]-2-(naphthalene-2-sulfonylamino)-propionyl]-(3-methoxybenzyl)-amino]acetic acid, MS (ion spray): 639 (M+H)+.

EXAMPLE 27

The following esters are obtained analogously to Example 23, but using the corresponding aminocarboxylic acid ester in place of N-(4-chlorobenzyl)glycine methyl ester hydrochloride (Example 23 d):
a) L-N-[N4-[[(S)-1-Amidino-3-piperidinyl]methyl]-N2-(2-naphthylsulfonyl)-L-asparaginyl]-1-phenylglycine methyl ester acetate, (1:1), MS (ion spray): 609 (M+H)+,
b) N-[N4-[[(S)-1-amidino-3-piperidinyl]methyl]-N2-(2-naphthyl- sulfonyl)-L-asparaginyl]-L-isoleucine methyl ester acetate (1:1), MS (ion spray): 589 (M+H)+,
c) N-[N4-[[(S)-1-amidino-3-piperidinyl]methyl]-N2-(2-naphthyl- sulfonyl)-L-asparaginyl]-L-valine methyl ester acetate (1:1), MS (ion spray): 575 (M+H)+, d) N-[N4-[[(S)-1-amidino-3-piperidinyl]methyl]-N2-(2-naphthyl- sulfonyl)-L-asparaginyl]-D-leucine methyl ester acetate (1:1), MS (ion spray): 589 (M+H)+, e) N-[N4-[[(S)-1-amidino-3-piperidinyl]methyl]-N2-(2-naphthyl- sulfonyl)-L-asparaginyl]-N-methyl-L-valine methyl ester acetate (1:1), MS (ion spray): 589 (M+H)+, f) N-[N4-[[(S)-1-amidino-3-piperidinyl]methyl]-N2-(2-naphthyl- sulfonyl)-L-asparaginyl]-N-methyl-L-isoleucine methyl ester acetate (1:1), MS (ion spray): 603 (M+H)+, g) methyl (R)-2-[(S)-3-[(S)-1-(amino-imino-methyl)-piperidin-3-ylmethylcarbamoyl]-2-(naphthalene-2-sulfonylamino)-propionylamino]-3-phenylpropionate acetate (1:1), MS (ion spray): 623 (M+H)+.

EXAMPLE 28

The following acids are prepared analogously to Example 24 starting from the ester of Example 27:

a) L-N-[N4-[[(S)-1-Amidino-3-piperidinyl]methyl]-N2-(2-naphthylsulfonyl)-L-asparaginyl]-2-phenylglycine acetate (1:1), MS (ion spray): 595 (M+H)+, b) N-[N4-[[(S)-1-amidino-3-piperidinyl]methyl]-N2-(2-naphthyl- sulfonyl)-L-asparaginyl]-L-isoleucine, MS (ion spray): 575 (M+H)+, c) N-[N4-[[(S)-1-amidino-3-piperidinyl]methyl]-N2-(2-naphthyl- sulfonyl)-L-asparaginyl]-L-valine, MS (ion spray): 561 (M+H)+, d) N-[N4-[[(S)-1-amidino-3-piperidinyl]methyl]-N2-(2-naphthyl- sulfonyl)-L-asparaginyl]-D-leucine, MS (ion spray): 575 (M+H)+, e) N-[N4-[[(S)-1-amidino-3-piperidinyl]methyl]-N2-(2-naphthyl- sulfonyl)-L-asparaginyl]-N-methyl-L-isoleucine, MS (ion spray): 589 (M+H)+, f) N-[N4-[[(S)-1-amidino-3-piperidinyl]methyl]-N2-(2-naphthyl- sulfonyl)-L-asparaginyl]-N-methyl-L-valine, MS (ion spray): 575 (M+H)+, g) (R)-2-[(S)-3-[(S)-1-(amino-imino-methyl)piperidin-3-ylmethylcarbamoyl]-2-(naphthalene-2-sulfonylamino)-propionylamino]-3-phenylpropionic acid, MS (ion spray): 609 (M+H)+.

EXAMPLE 29

A solution of 1.09 g of t-butyl (S)-3-[(S)-3-[butyl-[2-(ethoxalylamino-ethyl)]carbamoyl]-3-(naphthalene-2-sulfonyl- amino)-propionylaminoethyl]piperidine-1-carboxylate in 20 ml of methylene chloride is treated with 4 ml of trifluroacetic acid. After stirring, the mixture is concentrated. The residue is suspended with ether and the ether is then decanted. 3 ml of methanol, 1.06 ml of triethylamine and 377 mg of formamidinesulfonic acid are added to the residue. After stirring, an additional 1 equivalent each of formamidinesulfonic acid and triethylamine are added. The mixture is concentrated and chromatographed on silica gel with ethyl acetate-acetone-acetic acid-water 6:2:1:1. There are obtained 962 mg of methyl [2-[[(S)-3-[(S)-1-(amino-imino-methyl)-piperidin-3-ylmethylcarbamoyl]-2-(naphthalene-2-sulfonylamino)-propionyl]-butylamino]ethyl]oxamate acetate (1:1), MS (ion spray): 646 (M+H)+.

Preparation of the starting material:

a) 7.0 g of 2-butylamino-ethyl chloride hydrochloride (Org. Synth. IV 1963, 333) are stirred together with 7.9 g of sodium azide in 50 ml of DMF at 50°. After cooling, 82 ml of 1N sodium hydroxide solution are added dropwise. The mixture is taken up in 00 ml of ether, washed with water and, after drying the ether phase, treated with 25 ml of hydrochloric acid (5 molar in dioxane). After evaporating the ether phase, the residue is suspended in ether. The crystals are filtered and washed with ether. There are obtained g of 2-butylamino-ethyl azide hydrochloride, Rf=0.14.

b) 5.0 g of 2-butylamino-ethyl azide hydrochloride, 10.8 g of BOP and 11.98 ml of Hünig base are added to 8.85 g of N-(2-naphthyl- sulfonyl)-L-aspartic acid 4-t-butyl ester (Example 23e) in 120 ml of methylene chloride. After stirring, the mixture is taken up in 600 ml of ether and the ether phase is washed with 1N hydrochloric acid and with water. After drying and evaporating the ether phase, the residue is chromatographed over silica gel with methylene chloride/ether 19:1 and there are obtained 6.18 g of t-butyl (S)-[3-[(2-azidoethyl)-butyl-carbamoyl]-3-(naphthalene-2-sulfonylamino)propionate, Rf=0.42 (methylene chloride/ether 9:1).

c) 6.18 g of the product from b) are treated with 60 ml of 5N hydrochloric acid in dioxane. After stirring, the mixture is taken up in 400 ml of ether and the ether phase is washed with water. After drying and evaporation, there are obtained 5.58 g of (S)-[3-[(2-azidoethyl)-butyl-carbamoyl]-3-(naphthalene-2-sulfonylamino)propionic acid, Rf=0.21 (ethyl acetate).

d) 5.57 g of the product from c), 3.3 g of t-butyl (S)-3-aminomethyl-1-piperidinecarboxylate, 5.97 g of BOP and 4.4 ml of Hünig base are stirred in 80 ml of methylene chloride. Then, the mixture is taken up in ether and the ether phase is washed with 1N hydrochloric acid and with water. After drying and evaporation, the product is chromatographed on silica gel with ethyl acetate/hexane 4:1 and there are obtained 6.43 g of t-butyl (S)-3-[(S)-3-[(2-azidoethyl)-butyl-carbamoyl]-3-(naphthalene-2-sulfonylamino)propionylaminomethyl]piperidine-1-carboxylate (ethyl aceate/hexane 4:1).

e) 6.43 g of the product from d) in 60 ml of methanol are treated with 650mg of 5% Pd/C and hydrogenated under normal conditions. The catalyst is filtered and the filtrate is evaporated. There are obtained 5.86 g of t-butyl (S)-3[(S)-3-[(2-aminoethyl)-butylcarbamoyl]-3-(naphthalene-2-sulfonylamino)-propionylaminomethyl]piperidine-1-carboxylate, Rf=0.33 (ethyl acetate/acetone/water/acetic acid 6:2:1:1).

f) A solution of 0.23 ml of monoethyl oxalyl chloride in 6 ml of methylene chloride is added dropwise at 0°–5° to 1.2 g of the product from e) and 0.32 ml of pyridine. After stirring the mixture is taken up in 100 ml of ether and the ether phase is washed with 1N hydrochloric acid and with water. After drying and evaporation, the product is purified on silica gel with ethyl acetate. There are obtained 1.09g of t-butyl (S)-3-[(S)-3-[butyl-[2-(ethoxalylaminoethyl)carbamoyl]-3-(naphthalene-2-sulfonylamino)-propionylaminoethyl]-piperidine-1-carboxylate, MS (ion spray). 718 (M+H)+.

EXAMPLE 30

672 mg of the ester product from Example 29 in 6.7 ml of THF are stirred with a solution of 2.8 ml of 1N lithium hydroxide. Then, the mixture is treated with 4 ml of acetic acid and concentrated. The residue is purified on silica gel with ethyl acetate-acetone-acetic acid-water 6:2:1:1 to give 461 mg of [2-[[(S)-3-[(S)-1-(amino-imino-methyl)piperidin-3-ylmethylcarbamoyl]-2-(naphthalene-2-sulfonylamino)-propionyl]-butyl-amino]ethyloxamic acid, MS (ion spray): 632 (M+H)+.

EXAMPLE 31

The following products are obtained analogously to Example 29, but using a) acetic anhydride, b) methanesulfonyl chloride, c) SO₃—N(CH₃)₂ complex and, respectively, methyl chloroformate in place of monoethyl oxalyl chloride used in Example 29f):

a) (S)-N1-(2-Acetylaminoethyl)-N4-[(S)-1-(amino-imino-methyl)piperidin-3-ylmethyl]-N1-butyl-1-(naphthalene-2-sulfonylamino)-succinamide acetate (1:1), MS (ion spray): 602 (M+H)+, b) (S)-N4-[(S)-1-(amino-imino-methyl)piperidin-3yl-methyl]-N1-butyl-N1-(2-methanesulfonylamino-ethyl)-2-(naphthalene-2-sulfonylamino)-succinamide acetate (1:1), MS (ion spray): 638 (M+H)+, c) (S)-N4-[(S)-1-(amino-imino-methyl)piperidin-3-ylmethyl]-N1-butyl-2-(naphthalene-2-sulfonylamino)-N 1-(2-sulfonylaminoethyl)-succinamide, MS (ion spray): 640 (M+H)+, d) methyl 2-[[(S)-3-[(S)-1-(amino-imino-methyl)-piperidin-3-ylmethylcarbamoyl-2-(naphthalene-2-sulfonylamino)-pripionyl]-butyl-amino]-ethyl]-carbamate acetate (1:1), MS (ion spray): 618 (M+H)+.

EXAMPLE 32

The following products are manufactured analogously to Example 29 and, respectively, 30:

a) Acetic acid 3-[(S)-3-[(S)-1-amino-imino-methyl)-piperidin-3ylmethylcarbamoyl]-2-(naphthalene-2-sulfonylamino)-propionylcyclopropylamino]-propyl ester acetate (1:1), MS (ion spray): 601.3 (M+H)+, and, respectively, b) (S)-N4-[(S)-(1-amino-imino-methyl)piperidin-3-ylmethyl]-N1-cyclopropyl-N1-(3-hydroxypropyl)-2-(naphthalene-2-sulfonylamino)-succinamide acetate (1:1), MS (ion spray): 559 (M+H)+.

B) Preparation of the amine starting material used in place of 2-butylamino-ethyl azide hydrochloride (Example 29a):

a) 2.0 g of sodium hydride (55% in oil) are added at 0°-5° to a solution of 6.86 g of N-Boc-cyclopropylamine and 13.27 g of 3-(t-butyl-dimethyl-silyloxy)propyl bromide in 70 ml of DMF. After stirring the mixture is taken up in ether and the ether phase is washed with water. After drying and evaporating the ether phase and chromatography on silica gel with ether/hexane 1:9 there are obtained 11.73 g of t-butyl [3-(t-butyl-dimethyl-silanyloxy)propyl]-cyclopropyl-carbamidate, Rf=0.38 (ether/hexane 1:4).

b) 11.7 g of the product from a) are dissolved in 42.7 ml of a 1M solution of tetrabutylammonium fluoride in THF. After stirring the mixture is taken up in ether and the ether phase is washed with water. After drying and evaporation there are obtained 7.02 g of N-Boc-3-cyclopropylamino-propanol, Rf=0.47 (methylene chloride/ether 1:1).

c) A solution of 1.92 g of the product from b) in 19 ml of methylene chloride is treated with 1.44 ml of pyridine and 0.89 ml of acetic anhydride. After stirring the mixture is taken up in ether and the ether phase is washed with 1N hydrochloric acid and with water. After drying and evaporating the ether phase and chromatography on silica gel with ether/hexane 1:2 there are obtained 2.3 g of N-Boc-3-cyclopropylamino-propyl acetate, Rf=0.18 (ether/hexane 1:2).

d) 2.3 g of the product from c) are treated with 23 ml of 4.3M hydrochloric acid in dioxane. After evaporation of the solvent the residue is suspended with ether and the ether is subsequently decanted off. After drying there are obtained 1.61 g of methyl 3-cyclopropylamino-propionate hydrochloride (1:1), Rf=0.17 (ethyl acetate, acetone, acetic acid, water 6:2:1:1).

EXAMPLE 33

Analogously to Example 12, from t-butyl (R)-3-[[(S)-3-benzyl-methylcarbamoyl)-3-(naphthalene-2-sulfonylamino)-propionyl]-ethoxycarbonylmethyl-aminomethyl]-piperidine-1-carboxylate there is obtained ethyl [[(R)-1-(amino-imino-methyl)piperidin-3-ylmethyl]-[(S)-3-(benzyl-methyl-carbamoyl)-3-(naphthalene-2-sulfonylamino)propionyl]-amino]-3-acetate sulfite (2:1), MS (ion spray): 651.3 (M+H)+.

Preparation of the starting material:

a) 8.1 ml of 4-ethylmorpholine, 4.6 g of N-(dimethylaminopropyl)-N'-ethylcarbodiimide hydrochloride, 0.24 g of 4-dimethylaminopyridine and 2.6 ml of N-benzylmethylamine are added to a solution of 7.6 g of N-(2-naphthylsulfonyl)-L-aspartic acid 4-t-butyl ester (Example 23a) in 80 ml of methylene chloride. After stirring the mixture is poured into ice-cold 5% potassium hydrogen sulfate-10% potassium sulfate solution and extracted with methylene chloride. The organic phase is washed with sodium chloride solution, dried and evaporated. The residue is chromatographed on silica gel with hexane-ethyl acetate (3:1). There are isolated 3.4 g of 1-t-butyl (S)-N-benzyl-N-methyl-3-(naphthalen-2-ylsulfonylamido) succinamidate, MS (ion spray): 483.4 (M+H)+.

b) From the product of a) there is obtained analogously to Example 12i) t-butyl (R)-3-[[(S)-3-benzyl-methyl-carbamoyl)-3-(naphthalene-2-sulfonylamino)-propionyl]ethoxycarbonylmethylaminomethyl]-piperidine-1-carboxylate, MS (ion spray): 709.5 (M+H)+.

EXAMPLE 34

A solution of 0.2 g of the ester from Example 33 in 10 ml of methanol is treated with 1.4 1N sodium hydroxide solution. After stirring the reaction solution is treated with 6 ml of 1N hydrochloric acid and evaporated. The residue is chromatographed on RP-18 with a water-acetonitrile gradient. There is isolated 0.1 g of [[(R)-1-(amino-imino-methyl)piperidin-3-ylmethyl]-[(S)-3-(benzylmethylcarbamoyl)-3-(naphthalene-2-sulfonylamino)-propionyl]-amino]-3acetic acid hydrochloride (1:1), MS (ion spray): 623.3 (M+H)+.

EXAMPLE 35

Analogously to Example 9, but starting from 1-t-butyl (S)-N-benzyl-N-methyl-3-(naphthalen-2-ylsulfonylamino)succinamidate (Example 33a), there is obtained (S)-N4-[(R,S)-1-amino-imino-methyl)piperidin-3-ylmethyl) ]-N 1-benzyl-N4-(2-hydroxyethyl)-N1-methyl-2-(naphthalene-2-sulfoaylamino)-succinamide hydrochloride (1:1), MS (ion spray): 609.3 (M+H)+.

EXAMPLE 36

Analogously to Example 1, from tert-butyl (S)-N-cyclopropyl-N-(2-tetrazol-5-yl-ethyl)-3-(naphthalen-2-ylsulfonylamino)succinamate and from (S)-1-amidino-3-(aminomethyl)piperidine dihydrochloride there is manufactured (S)-N4-[(S)-1-(amino-iminomethyl)-piperidin-3-ylmethyl]-N1-cyclopropyl-N1-(2-tetrazol-5-ylethyl)-2-(2-(naphthylsulfonylamino)-succinamide, MS (ISP): 597.4 (M+H)+.

Preparation of the starting materials:

Aa) Analogously to Example 2B)e), but using 3-cyclopropylaminopropionitrile in place of sarcosine ethyl ester, there is obtained tert-butyl (S)-3-tert-butoxycarbonylamino-N-cyclopropyl-N-(2-cyanoethyl)-succinamate, MS (ISP): 382.2 (M+H)+.

Ab) Analogously to Example 2B)i), but using the ester from a) in place of t-butyl (S)-3-t-butoxycarbonylamino-N-ethoxycarbonylmethyl-N-methylsuccinamate, there is obtained tert-butyl (S)-N-cyclopropyl-N-(2-cyano-ethyl)-3-(naphthalene-2-sulfonylamino)succinamate, MS (FAB): 414 (M-isobutylene).

Ac) 0.7 g of ammonium chloride and 0.86 g of sodium azide are added in succession to a solution of 2.3 g of the material obtained under b) in 25 ml of DMF. The reaction mixture is stirred at 80° for 24 hours, cooled, filtered and the filtrate is evaporated. After chromatography of the residue on silica gel with ethyl acetate+0.5% ethyl acetate there is obtained 0.3 g of tert-butyl (S)-N-cyclopropyl-N-(2-tetrazol-5-yl-ethyl)-3-(naphthalen-2-ylsulfonylamino) succinamate, MS (ISP): 515.4 (M+H)+.

Ba) A solution of 42.5 g of N-(3-pyridinylmethyl)-benzamide in 220 ml of ethanol and 220 ml of 1N hydrochloric acid is treated with 4.2 g of palladium on charcoal and hydrogenated at room temperature for 24 hours over 100 bar of hydrogen. Then, the catalyst is filtered off and the filtrate is evaporated. The residue is taken up in methylene chloride and shaken with 1N sodium hydroxide solution. The organic phase is washed with water, dried and evaporated. There are obtained 36.1 g of (RS)-N-piperidin-3-ylmethyl-benzamide, MS (FAB): 218 M+.

Bb) 36.1 g of the material obtained under Ba) are dissolved in 800 ml of methylene chloride and treated with 25.2 g of D-mandelic acid. 380ml of ether are added dropwise to the resulting solution while stirring. After seeding, 32.5 g of salt crystallize out. Repeated recrystallization from 420 ml of methylene chloride, 10 ml of methanol and 140 ml of ether gives 19.5 g of (R)-N-piperidin-3-ylmethyl-benzamide (R)-hydroxy-phenyl-acetate (1:1), m.p: from 75°, decomposition.

Bc) 19.3 g of the mandelic acid salt obtained under Bb) are suspended in 193 ml of DMF, treated with 21.7 ml of triethylamine and 7.75 g of formamidine-sulfonic acid and stirred at room temperature. The reaction mixture is evaporated and the residue is chromatographed on RP-18 silica gel with a water-acetonitrile gradient. There are isolated 13.4 g of (S)-N-[1-(amino-imino- methyl)-piperidin-3-ylmethyl]-benzamide (R)-hydroxy-phenylacetate (1:1), MS (FAB): 218 M-(H₂N—CN).

Bd) 13.4 g of the mandelic acid salt obtained under Bc) are dissolved in 267 ml of concentrated hydrochloric acid and boiled under reflux. After cooling, the solution is extracted with ether. The aqueous phase is then evaporated and azeotroped with ethanol. The residue is suspended in 50 ml of ethanol, cooled in an ice bath and suction filtered. There are obtained 4.6 g of (S)-1-amidino-3-(aminomethyl)-piperidine dihydrochloride, $[\alpha]_D - 16.3°$ (c=1.0, water).

EXAMPLE 37

Analogously to Example 1, but using the nitrile from Example 36Ab) in place of t-butyl (S)-N-cyclohexyl-N-[(ethoxycarbonyl)methyl]-3-(2-naphthylsulfonamido)-succinamate, there is obtained (S)-N4-[(S)-1-(amino-imino-methyl)-piperidin-3-ylmethyl]-N1-(2-carbamoyl-ethyl)-N1-cyclopropyl-2-(naphthyl-2-sulfonylamino)-succinamide hydrochloride. MS (ISP): 572.3 (M+H)+.

EXAMPLE 38

38A) The following compounds are prepared analogously to Example 1:

38Aa) from tert-butyl (S)-3-(4-cyclopentyl-benzenesulfonylamino)-N-cyclopropyl-N-(2-ethoxycarbonyl-ethyl)-succinamate,
ethyl 3-[cyclopropyl-[(S)-3-[(S)-1-(amino-iminomethyl)piperidin-3-ylmethyl]-2-(4-cyclopentyl-phenylsulfonylamino)propionyl]-amino]-propionate hydrochloride, MS (FAB): 619.2 (M+H)+;

38Ab) from methyl (S)-2-[2-tert-butoxycarbonyl-1-[cyclopropyl-(2-ethoxycarbonyl-ethyl)-carbamoyl]-ethylsulfamoyl]-benzoate,
methyl 2-[(S)-2-[(S)-1-(amino-imino-methyl)-piperidin-3ylmethylcarbamoyl]-1-[cyclopropyl-(2-ethoxycarbonyl-ethyl)carbamoyl]-ethylsulfamoyl]-benzoate hydrochloride, MS (ISP): 609.4 (M+H)+;

38Ac) from tert-butyl (S)-N-cyclopropyl-N-ethoxycarbonylmethyl-3-(naphthalen-1-ylsulfonylamino)-succinamate,
ethyl [[(S)-3-[(S)-(1-amino-imino-methyl)-piperidin-3-ylmethylcarbamoyl]-2-(naphthalen-1-ylsulfonylamino)-propionyl]-cyclopropyl-amino]-acetate hydrochloride, MS (FAB): 587.4 (M+H)+;

38Ad) from tert-butyl (S)-N-cyclopropyl-N-(2-ethoxycarbonylethyl)-3-(4-trifluoromethoxy-benzenesulfonylamino)-succinamate,
ethyl 3-[[(S)-3-[(S)-1-(amino-imino-methyl)-piperidin-3-ylmethylcarbamoyl-2-(4-trifluoromethoxy-benzenesulfonylamino)propionyl]-cyclopropyl-amino]-propionate hydrochloride, MS (ISP): 635.5 (M+H)+;

38Ae) from tert-butyl (S)-3-(4-cyano-benzenesulfonylamino)-N-cyclopropyl-N-(2-ethoxycarbonylethyl)-succinamate,
ethyl 3-[[(S)-3-[(S)-1-(amino-imino-methyl)-piperidin-3-ylmethylcarbamoyl]-2-(4-cyano-phenylsulfonylamino)-propionyl] -cyclopropyl-amino]-propionate hydrochloride, MS (ISP): 576.7 (M+H)+;

38Af) from tert-butyl (S)-N-cyclopropyl-N-(2-ethoxycarbonylethyl)-3-methanesulfonylamino-succinamate,
ethyl 3-[[(S)-3-[(S)-1-(amino-imino-methyl)-piperidin-3-ylmethylcarbamoyl]-2-methylsulfonylamino-propionyl]-cyclopropylamino]-propionate hydrochloride, MS (ISP): 489.4 (M+H)+;

38Ag) from tert-butyl (S)-N-cyclopropyl-N-(2-ethoxycarbonylethyl)-3-(pyridin-3-ylsulfonylamino)-succinamate,
ethyl 3-[[(S)-3-[(S)-1-(amino-imino-methyl)-piperidin-3-ylmethylcarbamoyl]-2-pyridin-3-ylsulfonylamino-propionyl]-cyclopropyl-amino]-propionate trifluoroacetate, MS (ISP): 552.6 (M+H)+.

38B) Preparation of the starting materials:

The diester starting materials are obtained analogously to the procedure in Example 2B)i) from t-butyl (S)-3-t-butoxycarbonyl- amino-N-cyclopropyl-N-(2-ethoxycarbonyl-ethyl)-succinamate (Example 2B)h)1) using the corresponding aryl sulfochlorides in place of 2-naphthyl sulfochloride:

38Ba) tert-Butyl (S)-3-(4-cyclopentyl-benzenesulfonylamino)-N- cyclopropyl-N-(2-ethoxycarbonyl-ethyl)-succinamate, MS (FAB): 481 (M-isobutylene);

38Bb) methyl (S)-2-[2-tert-butoxycarbonyl-1-[cyclopropyl-(2-ethoxycarbonyl-ethyl)-carbamoyl]-ethylsulfamoyl]-benzoate, MS (FAB): 471 (M-isobutylene);

38Bc) tert-butyl (S)-N-cyclopropyl-N-ethoxycarbonylmethyl-3-(naphthalen-1-ylsulfonylamino)-succinamate, MS (ISP): 505.3 (M+H)+;

38Bd) tert-butyl (S)-N-cyclopropyl-N-(2-ethoxycarbonyl-ethyl)-3-(4-trifluoromethoxy-benzenesulfonylamino)-succinamate, MS (FAB): 497 (M-isobutylene);

38Be) tert-butyl (S)-3-(4-cyano-benzenesulfonylamino)-N- cyclopropyl-N-(2-ethoxycarbonyl-ethyl)-succinamate, MS (ISP): 494.2 (M+H)+;

38Bf) tert-butyl (S)-N-cyclopropyl-N-(2-ethoxycarbonyl-ethyl)-3-methanesulfonylamino-succinamate, MS (FAB): 361 (M+—OEt);

38Bg) tert-butyl (S)-N-cyclopropyl-N-(2-ethoxycarbonyl-ethyl)-3-(pyridin-3-ylsulfonylamino)-succinamate, MS (ISP): 470.2 (M+H)+.

EXAMPLE 39

The following acids are obtained analogously to Example 3, but starting from the esters of Example 38A:

a) 3-[Cyclopropyl-[(S)-3-[(S)-1-(amino-imino-methyl)-piperidin-3-ylmethyl]-2-(4-cyclopentyl-phenylsulfonylamino)-propionyl]amino]-propionic acid, MS (FAB): 591.3 (M+H)+;

b) 2-[(S)-2-[(S)-1 -(amino-imino-methyl)-piperidin-3-ylmethylcarbamoyl]-1-[cyclopropyl-(2-carbonethyl)-carbamoyl]-ethylsulfamoyl]-benzoic acid, MS (ISP): 567.2 (M+H)+;

c) [[(S)-3-[(S)-1-(amino-imino-methyl)-piperidin-3-ylmethylcarbamoyl]-2-(naphthalen-1-ylsulfonylamino)-propionyl]cyclopropyl-amino]-acetic acid, MS (FAB): 559.4 (M+H)+;

d) 3-[N-cyclopropyl-N-[(S)-3-[(S)-1-(amino-imino-methyl)piperidin-3-ylmethylcarbamoyl]-2-(4-trifluoromethoxy- phenylsulfonylamino)-propionyl]-amino]-propionic acid, MS (FAB): 607.2 (M+H)+;

e)1) 3-[[(S)-3-[(S)-1-(amino-imino-methyl)-piperidin-3-ylmethylcarbamoyl]-2-(4-cyano-phenylsulfonylamino)-propionyl]-cyclopropyl-amino]-propionic acid, MS (ISP): 548.5 (M+H)+;

e)2) 3-[[(S)-3-[(S)-1-(amino-imino-methyl)-piperidin-3-ylcarbamoyl]-2-(4-carbamoyl-phenylsulfonylamino)-propionyl]-cyclopropyl-amino]-propionic acid. MS (ISP): 566.6 (M+H)+;

f) 3-[[(S)-3-[(S)-1-(amino-imino-methyl)-piperidin-3-ylmethylcarbamoyl]-2-methylsulfonylamino-propionyl]-cyclopropyl-amino]propionic acid, MS (ISP): 461.3 (M+H)+;

g) 3-[[(S)-3-[(S)-1-(amino-imino-methyl)-piperidin-3-ylmethylcarbamoyl]-2-(pyridin-3-ylsulfonylamino)-propionyl]-cyclopropylamino]-propionic acid, MS (ISP): 524.3 (M+H)+.

EXAMPLE 40

Ethyl 3-[(S)-3-[(S)-1-(amino-imino-methyl)-piperidin-3-ylmethylcarbamoyl]-N-cyclopropyl-2-(4-tetrazol-5-yl-phenylsulfonylamino)-propionylamino]-propionate acetate, MS (ISP): 619.4 (M+H)+, is manufactured analogously to Example 1.

Preparation of the starting material:

1.4 g of the diester prepared in Example 38B)e) are dissolved in 14 ml of DMF, treated with 410 mg of ammonium chloride and 500 mg of sodium azide and stirred at 80° for 24 hours. After cooling to room temperature, the reaction mixture is filtered and the filtrate is evaporated. There are isolated 1.8 g of tert-butyl (S)-N- cyclopropyl-N-(2-ethoxycarbonyl-ethyl)-3-(4-tetrazol-5-yl-phenyl- sulfonylamino)-succinamate, MS (ISP): 537.4 (M+H)+.

EXAMPLE 41

Analogously to Example 3, from the ester of Example 40 there is obtained 3-[(S)-3-[(S)-1-(amino-imino-methyl)-piperidin-3-ylmethylcarbamoyl]-N-cyclopropyl-2-[4-(tetrazol-5-yl)-phenylsulfonylamino]-propionylamino]-propionic acid, MS (ISP): 591.4 (M+H)+.

EXAMPLE 42

The following compounds are prepared analogously to Example 1, but using the following enantiomers:

a) from N-Boc-D-aspartic acid β-t-butyl ester in place of N-Boc-L-aspartic acid β-t-butyl ester:
ethyl [[(R)-3-[(S)-1-(amino-imino-methyl)-piperidin-3-ylmethylcarbamoyl]-2-(naphthalen-2-ylsulfonylamino)-propionyl]cyclopropyl-amino]-acetate hydrochloride, MS (ISN): 585.4 (M−H)−;

b) from (R)-1-amidino-3-(aminomethyl)-piperidine dihydrochloride in place of (S)-1-amidino-3-(aminomethyl)-piperidindihydrochloride:
ethyl [[(S)-3-[(R)-1-(amino-imino-methyl)-piperidin-3-ylmethylcarbamoyl]-2-(naphthalen-2-ylsulfonylamino)-propionyl]cyclopropyl-amino]-acetate hydrochloride, MS (ISN): 585.7 (M−H)−;

c) from N-Boc-D-aspartic acid β-t-butyl ester in place of N-Boc-L-aspartic acid β-t-butyl ester and (R)-1-amidino-3-(aminomethyl)piperidine dihydrochloride in place of (S)-1-amidino-3-(aminomethyl)piperidine dihydrochloride:
ethyl [[(R)-3-[(R)-1-(amino-imino-methyl)-piperidin-3-ylmethylcarbamoyl]-2-(naphthalen-2-ylsulfonylamino)-propionyl]cyclopropyl-amino]-acetate hydrochloride, MS (ISP): 587.6 (M+H)+.

Preparation of the guanidine starting material of Example 42b):

In a procedure analogous to Example 36B), but using L-mandelic acid in place of D-mandelic acid there is obtained, via a) (S)-N-piperidin-3-ylmethyl-benzamide (S)-hydroxy-phenylacetate (1:1), MS (FAB): 218 M+, and b) (R)-N-[1-(amino-imino-methyl)-piperidin-(3)-ylmethyl]benzamide (S)-hydroxy-phenyl-acetate (1:1), MS (ISP): 261.4 (M+H)+, (R)-1-amidino-3-(aminomethyl)-piperidine dihydrochloride, $[\alpha]_D^{20} = +17.6°$ (c=1.0, water).

EXAMPLE 43

The following acids are prepared analogously to Example 3 from the esters of Example 42:

a) [[(R)-3-[(S)-1-(Amidino-imino-methyl)-piperidin-3-ylmethylcarbamoyl]-2-(naphthalen-2-ylsulfonylamino)-propionyl]-cyclopropyl-amino]-acetic acid, MS (ISP): 559.5 (M+H)+;

b) [[(S)-3-[(R)-1-(amidino-imino-methyl)-piperidin-3-ylmethylcarbamoyl]-2-(naphthalen-2-ylsulfonylamino)-propionyl]-cyclopropyl-amino]-acetic acid, MS (ISP): 559.5 (M+H)+;

c) [[(R)-3-[(R)-1-(amidino-imino-methyl)-piperidin-3-ylmethylcarbamoyl]-2-(naphthalen-2-ylsulfonylamino)-propionyl]-cyclopropyl-amino]-acetic acid, MS: (ISP): 559.5 (M+H)+.

EXAMPLE 44

The following products are prepared analogously to Example 1 from the corresponding t-butyl esters and using rac-2-(aminomethyl)-4-morpholinecarboxamidine trifluoroacetate (Example 7Bc)) in place of (S)-amidino-3-(aminomethyl)-piperidine dihydrochloride:

a) from tert-butyl (S)-N-cyclopropyl-N-(2-tetrazol-5-yl-ethyl)-3-(naphthalen-2-ylsulfonylamino)-succinamate (Example 36Ac)):

(S)-N4-[4-(amino-imino-methyl)-morpholin-2-ylmethyl]-N1-cyclopropyl-N1-[2-(tetrazol-5-yl)-ethyl]-2-(naphthalen-2-ylsulfonyl)-succinamide ((1:1) epimer mixture, MS (ISP): 599.5 (M+H)+;

b) from tert-butyl (S)-N-cyclopropyl-N-[2-(5-methyl-1,2,4-oxadiazol-3-yl)-ethyl]-3-(naphthalen-2-ylsulfonylamino)succinamate (Example 47e)):

(S)-N4-[4-(amino-imino-methyl)-morpholin-2-ylmethyl]-N1-cyclopropyl-N1-[2-(5-methyl-1,2,4-oxadiazol-3-yl)-ethyl]-2-(naphthalen-2-ylsulfonylamino)-succinamide hydrochloride (1:1), (1:1) epimer mixture, MS (ISP): 613.7 (M+H)+.

EXAMPLE 45

The following products are obtained analogously to Example 1 from the corresponding esters using rac-2-(aminomethyl)-4-morpholinecarboxamidine trifluoroacetate in place of (S)-1-amidino-3-(aminomethyl)-piperidine dihydrochloride:

a) from t-butyl (S)-N-cyclopropyl-N-ethoxycarbonylmethyl-3-(naphthalene-2-sulfonylamino)-succinamate (Example 2B)d)1)):

ethyl [[(S)-3-[4-(amino-imino-methyl)-morpholin-2-ylmethylcarbamoyl]-2-(naphthalen-2-ylsulfonyl)-propionyl] cyclopropyl-amino]-acetate hydrochloride (1:1), (1:1) epimer mixture, MS (ISP): 589.5 (M+H)+.

b) from the ester of Example 38 Bb):

methyl 2-[(S)-2-[4-(amino-imino-methyl)-morpholin-2-ylmethylcarbamoyl]-1-[(2-ethoxycarbonyl-ethyl)-cyclopropylcarbamoyl]-ethylsulfamoyl]-benzoate trifluoroacetate (1:1), (1:1)-epimer mixture, MS (ISP): 611.6 (M+H)+.

EXAMPLE 46

The following acids are obtained analogously to Example 3, but starting from the esters of Example 45:

a) [[(S)-3-[4-(Amino-imino-methyl)-morpholin-2-ylmethylcarbamoyl]-2-(naphthalen-2-ylsulfonyl)-propionyl]-cyclopropylamino]-acetic acid, (1:1) epimer mixture, MS (ISP): 561.4 (M+H)+;

b)1) 2-[(S)-2-[4-(amino-imino-methyl)-morpholin-2-ylmethylcarbamoyl]-1-[cyclopropyl-(2-ethoxy-carbonyl-ethyl)-carbamoyl]ethylaminosulfonyl]-benzoic acid, (1:1)-epimer mixture, MS (ISP): 597.5 (M+H)+;

b)2) 2-[(S)-2-[4-(amino-imino-methyl)-morpholin-2-ylmethylcarbamoyl]-1-[(2-carboxy-ethyl)-cyclopropyl-carbamoyl]ethylaminosulfonyl]-benzoic acid, (1:1) epimer mixture, MS (ISP): 569.4(M+H)+.

EXAMPLE 47

(S)-N4-[(S)-1-(Amino-imino-methyl)-piperidin-3-ylmethyl]-N1-cyclopropyl-N1-[2-(5-methyl-1,2,4-oxadiazol-3-yl)-ethyl]-2-(2-naphthylsulfonylamino)-succinamide hydrochloride, MS (ISP): 597.4 (M+H)+, is prepared analogously to Example 1.

Preparation of the starting material:

a) A solution of 57.8 g of di-tert-butyl dicarbonate in 300 ml of dioxane is added dropwise at room temperature to a solution of 29.2 g of 3-cyclopropylamino-propionitrile in 300 ml of dioxane. The solution is stirred at room temperature overnight and then evaporated. There are obtained 58.1 g of crude tert-butyl (2-cyanoethyl)-cyclopropyl-carbamate, MS (FAB): 154 (M-isobutylene).

b) 6.6 g of hydroxylamine hydrochloride and 13.6 g of sodium carbonate decahydrate are added to a solution of 20.0 g of the nitrile obtained under a) in 57 ml of ethanol and 23 ml of water. The reaction mixture is boiled under reflux and evaporated. The residue is suspended in hot ethanol and filtered. The filtrate is evaporated and the residue is recrystallized from isopropanol-hexane. The crystals obtained are dissolved in 10 ml of acetic anhydride and stirred at 80°. Subsequently, the reaction mixture is evaporated. The residue is treated with saturated sodium carbonate solution and extracted with ethyl acetate. The organic phases are evaporated and the residue is chromatographed on silica gel with hexane-ethyl acetate (3:1). There are obtained 5.4 g of tert-butyl cyclopropyl-2-(5-methyl-1,2,4-oxadiazol-3-yl)-ethyl-carbamate, MS (FAB): 211 (M-isobutylene).

c) 5.2 g of the material obtained under b) are dissolved in 30 ml of ethyl acetate, treated with 4 molar hydrochloric acid solution in ethyl acetate and stirred at room temperature. The solution is evaporated. The residue is suspended in ethyl acetate and filtered. There are isolated 3.7 g of cyclopropyl-2-(5-methyl-1,2,4-oxadiazol-3-yl)-ethylamine hydrochloride, MS (FAB): 167 (M+).

d) Analogously to the procedure of Example 2.B)e), but using the amine hydrochloride obtained under c) in place of sarcosine ethyl ester hydrochloride, there is obtained tert-butyl (S)-3-tert-butoxy- carbonylamino-N-cyclopropyl-N-[2-(5-methyl-1,2,4- oxadiazol-3-yl)-ethyl]-succinamate, MS (ISP): 439.6 (M+H)+.

e) Analogously to the procedure of Example 2.B)i), but using the diester obtained under d) in place of t-butyl (S)-3-t-butoxy- carbonylamino-N-ethoxy-carbonylmethyl-N-methylsuccinamate, there is prepared tert-butyl (S)-N-cyclopropyl-N-[2-(5-methyl-1,2,4-oxadiazol-3-yl)-ethyl]-3-(naphthalen-2-ylsulfonylamino)succinamate, MS (FAB): 473 (M-isobutylene).

EXAMPLE 48

Analogously to Example 1, from t-butyl (S)-N-cyclopropyl-N-ethoxycarbonylmethyl-3-(naphthalene-2-sulfonylamino)succinamate (Example 2.B)d)1)) using ethyl (S)-(3-aminomethylpiperidin-1-yl)-imino-methylcarbamate hydrochloride in place of (S)-1-amidino-3-(aminomethyl)piperidine dihydrochloride, there is obtained ethyl [cyclopropyl-[(S)-3-[(S)-1-(ethoxycarbonyl-aminoimino-methyl)-piperidin-3-ylmethylcarbamoyl]-2-(naphthalen-2-ylsulfonylamino)-propionyl]-amino]-acetate, MS (ISP): 659.6 (M+H)+.

Preparation of the starting material:

a) 3.7 g of tetrabutylammonium hydrogen sulfate and 100ml of 1N sodium hydroxide solution are added to a solution of 10.0 g of t-butyl (S)-3-aminomethyl-1-piperidinecarboxylate in 400ml of hexane and 100 ml of water. 9.3 ml of benzyl chloroformate are added dropwise to this mixture and the mixture obtained is stirred at room temperature for 3 hours. Subsequently, the organic phase is separated, washed with water, 10% citric acid, water and saturated sodium bicarbonate solution, dried and evaporated. t-Butyl (S)-3-[(1-benzyloxy)formamido]methyl]-1-piperidinecarboxylate is obtained.

b) 11.3 g of the material obtained under a) are dissolved in 120 ml of ethyl acetate, treated at 4° with 120 ml of a 4 molar solution of hydrochloric acid in ethyl acetate and stirred at room temperature for 5 hours. Subsequently, the reaction solution is concentrated. The residue is dissolved in 265 ml of DMF, treated with 18 ml of triethylamine and 4.3 g of formamidinesulfonic acid, and stirred at room temperature for 17 hours. The solvent is evaporated, the residue is treated with 1N hydrochloric acid, again concentrated and chromatographed on a RP-18 column with water-acetonitrile. There are thus isolated 5.4 g of benzyl [[(S)-1-amidino-3-piperidinyl]methyl]carbamate hydrochloride.

c) 0.55 ml of ethyl chloroformate is added dropwise to a solution of 2.0g of benzyl [[(S)-1-amidino-3-piperidinyl]methyl]carbamate hydrochloride in 200 ml of methylene chloride. The reaction mixture is cooled to 0°. 113 ml of 0.1N sodium hydroxide solution are added dropwise while stirring. Subsequently, the mixture is stirred in an ice bath. The phases are separated. The organic phase is washed with water, dried and evaporated. There are obtained 1.5 g of benzyl (S)-1-(ethoxycarbonylamino-imino-methyl)-piperidin-3-ylmethyl-carbamate, MS (FAB): 363.2 (M+H)+.

d) 1.5 g of the material obtained under c) are dissolved in 30 ml of ethanol and 30 ml of 1N hydrochloric acid, treated with 0.2 g of palladium on charcoal and hydrogenated. There are obtained 1.4 g of ethyl (S)-(3-aminomethyl-piperidin-1-yl)-imino-methylcarbamate hydrochloride, MS (ISP): 229.4 (M+H)+.

EXAMPLE 49

Analogously to Example 48, but using isobutyl chloroformate in place of ethyl chloroformate (in Example 48c), there is obtained, via isobutyl (S)-(3-benzyloxycarbonylaminomethyl-piperidin-1-yl)-imino-methylcarbamate, MS (FAB): 390 M+, and via isobutyl [(S)-3-aminomethyl-piperidin-1-yl]-imino-methylcarbamate hydrochloride (1:1), MS (thermospray): 257 (M+H)+, ethyl [cyclopropyl-[(S)-3-[(S)-1-(isobutoxycarbonylamino-imino-methyl)-piperidin-3-ylmethylcarbamoyl]-2-(naphthalen-2-ylsulfonylamino)-propionyl]-amino]acetate or the amidino group tautomer, MS (ISP) 687.7 (M+H)+.

EXAMPLE 50

Analogously to Example 48, but using ethyl (RS)-(2-amino-methyl-morpholin-4-yl)-imino-methylcarbamate hydrochloride in place of ethyl (S)-(3-aminomethyl-piperidin-1-yl)-iminomethylcarbamate hydrochloride, there is obtained ethyl [cyclopropyl-[(S)-3-[4-(ethoxycarbonylamino-imino-methyl)-morpholin-2-ylmethylcarbamoyl]-2-(naphthalen-2-ylsulfonylamino)-propionyl]-amino]acetate. (1:1) epimer mixture, MS (ISP): 661.5 (M+H)+.

Preparation of the starting material:

a) 23.15 ml of ethyl chloroformate are added to a suspension of 10.3 g of tert-butyl rac-[(4-amindino-2-morpholinyl)methyl]carbamate hemisulfite (Example 7Bb) in 1030 ml of methylene chloride. The reaction mixture is cooled to 4° and 637.2 ml of 0.1N sodium hydroxide solution are added dropwise thereto. Subsequently, the mixture is stirred at 5°. The organic phase is then separated, washed with water, dried and evaporated. There are isolated 10.5 g of ethyl (RS)-[2-(tert-butoxycarbonylaminomethyl)- morpholin-4-yl]-imino-methylcarbamate, MS (ISP): 331.4 (M+H)+.

b) 8.9 g of the material obtained under a) are dissolved in 50 ml of ethyl acetate, treated with 50 ml of 4 molar hydrochloric acid in ethyl acetate and stirred at room temperature. After evaporation of the resulting suspension, there are obtained 7.3 g of ethyl (RS)-(2-aminomethyl-morpholin-4-yl)-imino-methylcarbamate hydrochloride, MS (ISP): 231.4 (M+H)+.

EXAMPLE 51

The following compounds are prepared analogously to Example 50 from the corresponding esters:

a) from tert-butyl (S)-N-cyclopropyl-N-(2-tetrazol-5-yl-ethyl)-3-(naphthalen-2-ylsulfonylamino)-succinamate (Example 36Ac),
ethyl 12-[(S)-3-[cyclopropyl-2-(tetrazol-5-yl)-ethyl-carbamoyl]-3-(naphthalen-2-ylsulfonylamino)-propionylaminomethyl]-morpholin-4-yl]-imino-methylcarbamate, (1:1)-epimer mixture, MS (ISP): 671.6 (M+H)+;

b) from N-[3-(t-butoxycarbonyl)-N-(2-naphthylsulfonyl)-L-alanyl]-N-cyclopropyl-β-alanine ethyl ester (Example 2.B)j)9)),
ethyl 3-[[(S)-3-[4-(ethoxycarbonylamino-imino-methyl)morpholin-2-ylmethylcarbamoyl]-2-(naphthalen-2-ylsulfonyl- amino)-propionyl]-cyclopropyl-amino]-propionate or the amidino group tautomer, (1:1) epimer mixture, MS (ISN): 673.5 (M−H)−.

EXAMPLE 52

The corresponding products are obtained analogously to Example 48 from tert-butyl (S)-N-cyclopropyl-N-(2-tetrazol-5-ylethyl)-3-(naphthalen-2-ylsulfonylamino)-succinamate (Example 36Ac) and the following aminomethyl-piperidine derivatives:
  a) from ethyl (S)-(3-aminomethyl-piperidin-1-yl)-iminomethylcarbamate hydrochloride (Example 48d),
    ethyl [(S)-3-[(S)-3-[cyclopropyl-2-(tetrazol-5-yl)-ethylcarbamoyl]-3-(naphthalen-2-ylsulfonamino)-propionylaminomethyl]-piperidin-1-yl]-imino-methylcarbamate, MS (ISP): 669.6 (M+H)+
  b) from isobutyl [(S)-3-aminomethyl-piperidin-1-yl]-iminomethylcarbamate hydrochloride (1:1 ) (Example 49)
    ethyl (S)-N1-cyclopropyl-N4-[(S)-1-isobutoxycarbonylamino-imino-methyl)-piperidin-3-ylmethyl]-2-(naphthalen-2-ylsulfonyl- amino)-N1-[2-(tetrazol-5-yl)-ethyl]-succinamide, MS (ISP): 697.5 (M+H)+.

EXAMPLE 53

The following products are obtained analogously to Example 48 using the corresponding arylsulfonyl esters in place of t-butyl (S)-N- cyclopropyl-N-ethoxycarbonylmethyl-3-(naphthalen-2-sulfonyl- amino)-succinamate:
  a) from N-[3-(t-butoxycarbonyl)-N-(2-naphthylsulfonyl)-L-alanyl]-N-cyclopropyl-β-alanine ethyl ester (Example 2.B)j)9),
    ethyl 3-[[(S)-3-[(S)-1-(ethoxycarbonylamino-imino-methyl)- piperidin-3-ylmethylcarbamoyl]-2-(naphthalen-2-ylsulfonylamino)propionyl]-cyclopropyl-amino]-propionate or the amidino group tautomer, MS (ISP): 673.5 (M+H)+;
  b) from methyl (S)-2-[2-tert-butoxycarbonyl-1-[cyclopropyl-(2-ethoxycarbonyl-ethyl)-carbamoyl]-ethylsulfamoyl]-benzoate (Example 38Bb),
    ethyl 3-[[(S)-3-[(S)-1-(ethoxycarbonylamino-imino-methyl)- piperidin-3-ylmethyl carbamoyl]-2-(2-methoxycarbonyl-phenyl- sulfonylamino)-propionyl]-cyclopropyl-amino]-propionate or the amidino group tautomer, MS (ISP): 681.5 (M+H)+.

EXAMPLE 54

Analogously to Example 3, but using the corresponding esters, there are obtained:
  54a) from the ester of Example 51b)
    3-[[(S)-3-[4-(ethoxycarbonylamino-imino-methyl)-morpholin-2-ylmethylcarbamoyl]-2-(naphthalen-2-ylsulfonylamino)propionyl]-cyclopropyl-amino]-propionic acid or the amidino group tautomer, (1:1) epimer mixture, MS (ISN): 645.2 (M−H)−;
  54b) from the ester of Example 53b)
    54b)1. 2-[(S)-1-[(2-carboxy-ethyl)-cyclopropyl-carbamoyl]-2-[(S)-1-(ethoxycarbonylamino-imino-methyl)-piperidin-3-ylmethylcarbamoyl]-ethylsulfamoyl]-benzoic acid or the amidino group tautomer, MS (ISP) 639.5 (M+H)+, and
    54b)2. 2-[(S)-1-[(2-ethoxycarbonyl-ethyl)-cyclopropyl-carbamoyl]-2-[(S)-1-(ethoxycarbonylamino-imino-methyl)-piperidin-3-ylmethylcarbamoyl]-ethylsulfamoyl]-benzoic acid or the amidino group tautomer, MS (ISP) 667.6 (M+H)+.

EXAMPLE 55

Analogously to Example 29, via
  a) benzyloxycarbonylamino-acetic acid cyclopropylamide, MS (EI): 248 (M),
  b) benzyl 2-cyclopropylamino-ethylcarbamate hydrochloride (1:1), MS (EI): 234 (M),
  c) tert-butyl (S)-3-[(S)-3-[(2-amino-ethyl)-cyclopropyl-carbamoyl]-3-(naphthalen-2-ylsulfonylamino)-propionylaminomethyl]-piperidine-1-carboxylate hydrochloride (1:1), and
  d) tert-butyl (S)-3-[(S)-3-[cyclopropyl-(2-pyrazin-2-ylcarbonylamino-ethyl)-carbamoyl]-3-(naphthalen-2-ylsulfonylamino)propionylaminomethyl]-piperidine-1-carboxylate, MS (ISP): 708.8 (M+H), there is obtained (S)-N4-[(S)- 1-(amino-imino-methyl)-piperidin-3-ylmethyl]-N1-cyclopropyl-2-(naphthalen-2-ylsulfonylamino)-N1-[2-(pyrazin-2-ylcarbonylamino)-ethyl]-succinamide acetate (1:3), MS (ISP): 650.7 (M+H).

Preparation of the starting material:
  a) 23.1 g of N-(3-dimethylaminopropyl)-N'-ethylcarbodiimide hydrochloride (EDC) are added while stirring to 24 g of N-benzyloxycarbonyl-glycine and 8 ml of cyclopropylamine in 240ml of methylene chloride and the mixture is stirred at room temperature for 4 hours. The mixture is taken up in ether and washed with 1N hydrochloric acid, with bicarbonate solution and with water. After drying and evaporating the ether phase there are obtained 23 g of benzyloxycarbonylamino-acetic acid cyclopropylamide.
  b) 17.6 ml of borane-dimethyl sulfide are added dropwise at 10°–23° to 23 g of the product from a) in 250 ml of THF. The mixture is heated under reflux, then cooled to −10°. 75 ml of 2N hydrochloric acid are added dropwise thereto while cooling with ice and the mixture is taken up in ether at room temperature. The ether phase is washed with water. The aqueous phases are again made basic with 90 ml of 2N sodium hydroxide solution and extracted with ether. The ether phases are washed with water, then acidified (pH 2) with 2N hydrochloric acid (in dioxane) and concentrated. The residue is suspended in ether and filtered. There are obtained 11 g of benzyl 2-cyclopropylamino-ethylcarbamate hydrochloride.
  c) Analogously to Example 29b)c)d)e) there is obtained tert-butyl (S)-3-[(S)-3-[(2-amino-ethyl)-cyclopropyl-carbamoyl]-3-(naphthalen-2-ylsulfonylamino)-propionylaminomethyl]-piperidine-1-carboxylate hydrochloride.
  d) 94 mg of pyrazinecarboxylic acid and 127 mg of EDC are added to 400 mg of the amine hydrochloride from c) and 0.11 ml of Hünig base in 4 ml of methylene chloride. The mixture is stirred at room temperature for 20 hours and then taken up in ethyl acetate. The ethyl acetate phase is washed with water. After drying and evaporation, the crude product is chromatographed over silica gel with ethyl acetate/methanol (9:1). There are obtained 288 mg of tert-butyl (S)-3-[(S)-3-[cyclopropyl-(2-pyrazin-2-ylcarbonylamino- ethyl)-carbamoyl]-3-(naphthalen-2-ylsulfonylamino)-propionylaminomethyl]-piperidine-1-carboxylate.

EXAMPLE 56

The following compounds are obtained analogously to Example 55, but using the corresponding acids or acid derivatives in place of the pyrazinecarboxylic acid used in Example 55d), namely using a) monomethyl oxalyl chloride, b) SO$_3$—N(CH$_3$)$_3$ complex, c) benzyl chloroformate, d) chloroacetic acid, e) phenoxyacetyl chloride, f) phenylglyoxylic acid, g) pyruvic acid, h) nicotinic acid, i) nicotinic acid N-oxide and, respectively, j) 3,4-dihydroxyphenylacetic acid:

a) Methyl N-[2-[[(S)-3-[(S)-1-(amino-imino-methyl)-piperidin-3-ylmethylcarbamoyl]-2-(naphthalen-2-ylsulfonylamino)-propionyl]cyclopropyl-amino]-ethyl]-oxamate acetate (1:1), MS (ISP): 630.5 (M+H);

b) 2-[[(S)-3-[(S)-1-(amino-imino-methyl)-piperidin-3-ylmethylcarbamoyl]-2-(naphthalen-2-ylsulfonylamino)-propionyl]cyclopropyl-amino]-ethylsulfamic acid, MS (ISP): 624.5 (M+H);

c) benzyl 2-[[(S)-3-[(S)-1-(amino-imino-methyl)-piperidin-3-ylmethylcarbamoyl]-2-(naphthalen-2-ylsulfonylamino)-propionyl]cyclopropyl-amino]-ethylcarbamate acetate (1:1), MS (ISP): 678.5 (M+H);

d) (S)-N4-[(S)-1-(amino-imino-methyl)-piperidin-3-ylmethyl]-N1-(2-chloroacetylamino-ethyl)-N1-cyclopropyl-2-(naphthalen-2-ylsulfonylamino)-succinamide acetate (1:1), MS (ISP): 620.4 (M+H);

e) (S)-N4-[(S)-1-(amino-imino-methyl)-piperidin-3-ylmethyl]-N1-cyclopropyl-2-(naphthalen-2-ylsulfonylamino)-N1-(2-phenoxyacetylamino-ethyl)-succinamide acetate (1:1), MS (ISP): 678.6 (M+H);

f) (S)-N4-[(S)-1-(amino-imino-methyl)-piperidin-3-ylmethyl]-N1-cyclopropyl-2-(naphthalen-2-ylsulfonylamino)-N1-[2-(2-oxo-2-phenyl-acetylamino)-ethyl]-succinamide acetate (1:2), MS (ISP): 676.6 (M+H);

g) (S)-N4-[(S)-1-(amino-imino-methyl)-piperidin-3-ylmethyl]-N1 -cyclopropyl-2-(naphthalen-2-ylsulfonylamino)-N1-[2-(2-oxopropionylamino)-ethyl]-succinamide acetate (1:1), MS (ISP): 614.6 (M+H);

h) (S)-N4-[(S)-1-(amino-imino-methyl)-piperidin-3-ylmethyl]-N1-cyclopropyl-2-(naphthalen-2-ylsulfonylamino)-N1-[2-(pyridin-3-ylcarbonylamino)-ethyl]-succinamide acetate (1:2), MS (ISP): 649.1 (M+H);

i) (S)-N4-[(S)-1-(amino-imino-methyl)-piperidin-3-ylmethyl]-N1-cyclopropyl-2-(naphthalen-2-ylsulfonylamino )-N1-[2-(1-oxynicotinoylamino)-ethyl]-succinamide acetate (1:1), MS (ISP): 666.5 (M+H);

j) (S)-N4-[(S)-1-(amino-imino-methyl)-piperidin-3-ylmethyl]-N1-cyclopropyl-N1-[2-(3,4-dihydroxyphenylacetylamino)-ethyl]-2-(naphthalen-2-ylsulfonylamino)-succinamide acetate (1:1), MS (ISP): 694.6 (M+H).

EXAMPLE 57

The following acid is obtained analogously to Example from the ester of Example 56a):

N-[2-[[(S)-3-[(S)-1-(Amino-imino-methyl)-piperidin-3-ylmethylcarbamoyl]-2-(naphthalen-2-ylsulfonylamino)-propionyl]cyclopropyl-amino]-ethyl]-oxamic acid, MS (ISP): 616.5 (M+H).

EXAMPLE 58

Analogously to Examples 29 and 55, but using methyl [(S)-3-aminomethyl-piperidin-1-yl]-imino-methylcarbamate hydrochloride (1:2) in place of t-butyl (S)-3-aminomethyl-1-piperidinecarboxylate (Example 29d), there is obtained methyl [(S)-3-[(S)-3-[(2-chloroacetylamino-ethyl)-cyclopropyl-carbamoyl]-2-(naphthalen-2-ylsulfonylamino)-propionylaminomethyl]-piperidin-1-yl]-iminomethylcarbamate, MS (ISP): 648.4 (M+H).

Preparation of the starting material:

Analogously to Example 48, but using methyl chloroformate in place of ethyl chloroformate (Example 48c), there is obtained methyl [(S)-3-aminomethyl-piperidin-1-yl]-imino-methylcarbamate hydrochloride (1:2), MS (thermospray): 215 (M+H).

EXAMPLE 59

The following compounds are prepared analogously to Example 58:

a) Methyl N-[2-[cyclopropyl-[(S)-3-[(S)-1-(iminomethoxy- carbonylamino-methyl)-piperidin-3-ylmethylcarbamoyl]-2-(naphthalen-2-ylsulfonylamino)-propionyl]-amino]-ethyl]-oxamate, MS (ISP): 702.6 (M+H);

b) benzyl 2-[cyclopropyl-[[(S)-3-[(S)-1-(methoxycarbonylamino- imino-methyl)-piperidin-3-ylmethylcarbamoyl]-2-(naphthalen-2-ylsulfonylamino)-propionyl]-amino]-ethylcarbamate, MS (ISP): 736.7 (M+H);

c) methyl [(S)-3-[(S)-3-[cyclopropyl-(2-methylsulfonylamino- ethyl)-carbamoyl]-3-(naphthalen-2-ylsulfonylamino)-propionylaminomethyl]-piperidin-1-yl]-imino-methylcarbamate, MS (ISP):680.5 (M+H).

EXAMPLE 60

Analogously to Example 29, but using N-cyclopropylglycine ethyl ester in place of 2-butyl-aminoethyl azide hydrochloride (in Example 29b), there is obtained via

[[(S)-3-[(S)-1-tert-butoxycarbonyl-piperidin-3 -ylmethylcarbamoyl]-2-(naphthalene-2-sulfonylamino)-propionyl]-cyclopropyl-amino]-acetic acid and tert-butyl (S)-3-[(S)-3-(cyclopropyl-methoxycarbamoylmethylcarbamoyl)-3-(naphthalen-2-ylsulfonylamino)-propionylaminomethyl]-piperidine-1-carboxylate, (S)-N4-[(S)-1-(amino-imino-methyl)-piperidin-3-ylmethyl]-N 1-cyclopropyl-N1-methoxycarbamoylmethyl-2-(naphthalen-2-ylsulfonylamino)-succinamide acetate (1:1), MS (ISP): 588.6 (M+H).

Preparation of the starting material:

500 mg of [[(S)-3-[(S)-1-tert-butoxycarbonyl-piperidin-3-ylmethylcarbamoyl]-2-(naphthalen-2-sulfonylamino)-propionyl]-cyclopropyl-amino]-acetic acid are stirred at room temperature for 20 hours in 10 ml of methylene chloride together with 71 mg of O-methylhydroxylamine hydrochloride, 0.28 ml of N-methylmorpholine and 376 mg of BOP. The mixture is taken up in ethyl acetate and washed with 1N hydrochloric acid and then with water. After drying and evaporation the product is purified over silica gel with ethyl acetate/methanol (9:1). There are obtained 282 mg of tert-butyl (S)-3-[(S)-3-([cyclopropyl-methoxycarbamoylmethylcarbamoyl)]-3-(naphthalen-2-ylsulfonylamino)-propionylaminomethyl]-piperidine-1-carboxylate, MS (ISP): 646.6 (M+H).

EXAMPLE 61

The following compounds are obtained analogously to Examples 29 and 60:
a) (S)-N4-[(S)-1-(Amino-imino-methyl)-piperidin-3-ylmethyl]-N1-benzyloxycarbamoylmethyl-N1-cyclopropyl-2-(naphthalen-2-ylsulfonylamino)-succinamide acetate (1:1), MS (ISP): 664.5 (M+H);
b) (S)-N4-[(S)-1-(amino-imino-methyl)-piperidin-3-ylmethyl]-N1-cyclopropyl-N1-methylsulfonylcarbamoylmethyl-2-(naphthalen-2-ylsulfonylamino)-succinamide acetate (1:1), MS (ISP): 636.5 (M+H);
c) (S)-N4-[(S)-1-(amino-imino-methyl)-piperidin-3-ylmethyl]-N1-cyclopropyl-N1-cyclopropylcarbamoylmethyl-2-(naphthalen-2-ylsulfonylamino)-succinamide acetate (1:1), MS (ISP): 598.6 (M+H);
d) (S)-N4-[(S)-1-(amino-imino-methyl)-piperidin-3-ylmethyl]-N1-cyclopropyl-2-(naphthalen-2-ylsulfonylamino)-N1-(pyridin-3-ylmethylcarbamoylmethyl)-succinamide acetate (1:2), MS (ISP): 649.5 (M+H);
e) (S)-N4-[(S)-1-(amino-imino-methyl)-piperidin-3-ylmethyl]N-1 -cyclopropyl-N1-[2-(3,4-dihydroxyphenyl)-ethylcarbamoylmethyl]-2-(naphthalen-2-ylsulfonylamino)-succinamide acetate (1:2), MS (ISP): 694.5 (M+H);
f) (S)-N4-[(S)-1-(amino-imino-methyl)-piperidin-3-yl]-N1-cyclopropyl-N1-(2-hydroxy-ethylcarbamoylmethyl)-2-(naphthalen-2-ylsulfonylamino)-succinamide acetate (1:1), MS (ISP): 602.2 (M+H).

EXAMPLE 62

2.0 g of (S)-N-(3-benzyloxy-propyl)-N-cyclopropyl-3-(naphthalen-2-ylsulfonylamino)-succinamic acid and 1.35 g of methyl [(S)-3-aminomethyl-piperidin-1-yl]-imino-methylcarbamate hydrochloride (1:2) (Example 58) are stirred at room temperature together with 1.91 g of BOP and 2.34 ml of 1,8-diazabicyclo (5.4.0) undec-7-ene (DBU) in 20 ml of methylene chloride. After evaporation and chromatography over silica gel with ethyl acetate/methanol (19:1), there are obtained 2.35 g of methyl (S)-3-[(S)-3-[(3-benzyloxy-propyl)-cyclopropyl-carbamoyl]-3-(naphthalen-2-ylsulfonylamino)-propionylaminomethyl]-piperidin- 1-yl]-iminomethylcarbamate.

Preparation of the starting material:
a) 8.58 g of N-BOC-cyclopropylamine and 15 g of O-benzyl-3-bromo-1-propanol in 90 ml of DMF are treated at 0°-5° with 2.5 g of sodium hydride (55% in oil). The mixture is stirred at 0°-5° for 1 hour and at room temperature for 3 hours and then treated at 0°-5° with aqueous ammonium chloride solution. The mixture is partitioned in ether/water and the ether phases are washed with water, then dried and concentrated. After chromatography over silica gel with ether/hexane (1:4), the 11.5 g of product are stirred with 120 ml of 4.8 molar hydrochloric acid in dioxane. After concentration, the residue is crystallized in ether. The crystals are filtered and washed with ether. There are obtained 9.0 g of (3-benzyloxy-propyl)-cyclopropyl-amine hydrochloride, MS (EI): 206 (M+H).

b) 9.0 g of product from a) and 11.77 g of N-(2-naphthyl-sulfonyl)-L-asparatic acid 4-t-butyl ester (Example 23a) are stirred in 200 ml of methylene chloride together with 14.4 g of BOP and 15.9 ml of Hünig base. The mixture is taken up in ether and the ether phase is washed with 1N hydrochloric acid and then with water. After drying and evaporation of the ether phase, the residue is chromatographed over silica gel with ethyl acetate/hexane (1:2). There are obtained 14.85 g of tert-butyl (S)-N-(3-benzyloxy-propyl)-N-cyclopropyl-3-(naphthalen-2-ylsulfonylamino)succinamate, MS (ISN): 565.8 (M−H).

c) 14.85 g of the product from b) are dissolved in 60 ml of dioxane and this solution is treated with 120 ml of 4.8 molar hydrochloric acid in dioxane. The mixture is stirred at room temperature, taken up in ether and washed with water. After drying and evaporation of the ether phase, there are obtained 12.87 g of (S)-N-(3-benzyloxy-propyl)-N-cyclopropyl-3-(naphthalen-2-ylsulfonylamino)-succinamic acid, MS (ISP): 509.2 (M−H).

EXAMPLE 63

970mg of methyl (S)-3-[(S)-3-[(3-Benzyloxy-propyl)-cyclopropyl-carbamoyl]-3-(naphthalen-2-ylsulfonylamino)propionylaminomethyl]-piperidin-1-yl]-imino-methylcarbamate are dissolved in 5 ml of methylene chloride and the solution is treated with 5 ml of a 0.5 molar boron tribromide solution in methylene chloride. After stirring at room temperature for 1.5 hours, the mixture is treated with 20 ml of saturated sodium bicarbonate solution. The mixture is partitioned between ethyl acetate and water. After drying and evaporation, the crude product is purified over silica gel with ethyl acetate/methanol 9:1. There are obtained 465 mg of pure methyl [(S)-3-[(S)-3-[cyclopropyl-(3-hydroxypropyl)-carbamoyl]-2-(naphthalen-2-ylsulfonylamino)-propionylaminomethyl]-piperidin-1-yl]-imino-methylcarbamate, MS (ISO): 617.7 (M+H).

EXAMPLE 64

274 mg of methyl [(S)-3-[(S)-3-[cyclopropyl-(3-hydroxypropyl)-carbamoyl]-2-(naphthalen-2-ylsulfonylamino)-propionylaminomethyl]-piperidin- 1-yl]-imino-methylcarbamate (Example 63), 1 ml of 1N methyl iodide in THF, 2 ml of 1 molar DBU solution in THF and 2 ml of methylene chloride are stirred together at room temperature. The mixture is concentrated and the residue is chromatographed over silica gel with ethyl acetate-methanol 9:1. There are obtained 120mg of (S)-N1-cyclopropyl-N4-[(S)-1-(iminomethoxycarbonylamino-methyl)-piperidin-3-ylmethyl]-N1-(3 -methoxy-propyl)-2-(naphthalen-2-ylsulfonylamino)-succinamide, MS (ISO): 631.6 (M+H).

EXAMPLE 65

Analogously to Example 29, but using a) phosphoric acid diphenyl ester chloride or b) phosphoric acid diethyl ester chloride in place of monoethyl oxalyl chloride (Example 29f), there are obtained
a) 2-[[(S)-3-[(S)-1-(Amino-imino-methyl)-piperidin-3-ylmethylcarbamoyl]-2-(naphthalen-2-sulfonylamino)-propionyl]-butylamino]-ethylamidophosphoric acid diphenyl ester acetate (1:1), MS (ISP): 792.4 (M+H),
b) (S)-N4-[(S)-1-(amino-imino-methyl)-piperidin-3-yl]-N1-butyl-N1-(2-diethoxyphosphorylaminoethyl)-2-(naphthalen-2-sulfonylamino)-succinamide acetate (1:1), MS (ISP): 696.2 (M+H).

EXAMPLE 66

Analogously to Example 48, but using di-t-butyl dicarbonate in place of ethyl chloroformate (in Example 48c), there is obtained, via
 tert-butyl (S)-(3-benzyloxycarbonylaminomethyl-piperidin-1-yl)-imino-methylcarbamate, MS (thermospray): 391 (M+H)+, and via
 tert-butyl (S)-(3-aminomethyl-piperidin-1-yl)-imino-methyl carbamate, MS (ISP): 257.2 (M+H)+,
 ethyl [[(S)-3-[(S)-1-(tert-butoxycarbonylamino-imino-methyl)piperidin-3-ylmethylcarbamoyl]-2-(naphthalen-2-ylsulfonylamino)propionyl]-cyclopropyl-amino]-acetate, MS (ISP): 687.5 (M+H)+.

EXAMPLE 67

Analogously to Example 1, but using [(4-aminomethyl-piperidin-1-yl)-imino-methyl]amine dihydrochloride in place of (S)-1-amidino-3-(aminomethyl)piperidine dihydrochloride, there is prepared ethyl (S)-3-[[3-[1-(amino-imino-methyl)-piperidin-4-ylmethylcarbamoyl]-2-(naphthalen-2-ylsulfonylamino)-propionyl]-cyclohexyl-amino]-acetate hydrochloride, MS (ISP): 629.6 (M+H)+.

Preparation of the starting material:
a) A solution of 130g of 1,1-dimethylethyl (4-piperidinyl-methyl)-carbamate in 1300 ml of DMF is treated with 138 ml of triethylamine and 61.8 g of formamidinesulfonic acid and the mixture is stirred at room temperature overnight. The precipitated material is filtered, suspended in 500 ml of ethanol, again filtered off and dried. There are obtained 65.6 g of tert-butyl 1-(amino-imino-methyl)-piperidin-4-ylmethylcarbamate hemisulfite, MS (ISP): 257.4 (M+H)+.
b) 65.6 g of the material obtained under a) are dissolved in 656 ml of 1N hydrochloric acid and stirred at 50° for 5 hours. The solvent is evaporated and the residue is suspended in 500 ml of ethanol, filtered off under suction and dried. There are obtained 48.5 g of [(4-aminomethyl-piperidin-1-yl)-imino-methyl]-amine dihydrochloride, MS (ISP): 573.5 (M+H)+.

EXAMPLE 68

The following products are prepared analogously to Example 67 from the corresponding tert-butyl esters:
68a) Ethyl [[(S)-3-[1-amino-imino-methyl)-piperidin-4-ylmethylcarbamoyl]-2-(naphthalen-2-ylsulfonylamino)-propionyl]-cyclopropyl-amino]-acetate trifluoroacetate, MS (ISP): 587.8 (M+H)+;
68b) ethyl [[(S)-3-[1-(amino-imino-methyl)-piperidin-4-ylmethylcarbamoyl]-2-(naphthalen-2-ylsulfonylamino)-propionyl]-benzyl-amino]-acetate hydrochloride (1:1), MS (ISP): 637.4 (M+H)+;
68c) ethyl [[(S)-3-[1-(amino-imino-methyl)-piperidin-4-ylmethylcarbamoyl]-2-(naphthalen-2-ylsulfonylamino)-propionyl]-cyclo-hexylmethyl-amino]-acetate hydrochloride; MS (ISP): 643.6 (M+H)+;
68d) ethyl [[(S)-3-[1-(amino-imino-methyl)-piperidin-4-ylmethylcarbamoyl]-2-(naphthalen-2-ylsulfonylamino)-propionyl]-butylamino]-acetate hydrochloride (1:1), MS (ISP): 603.4 (M+H)+;
68e) ethyl (S)-3-[[3-[1-(amino-imino-methyl)-piperidin-4-ylmethylcarbamoyl]-2-(naphthalen-2-ylsulfonylamino)-propionyl cyclopropyl-amino]propionate hydrochloride, MS (ISP): 601.6 (M+H)+;
68f) ethyl (S)-3-[[3-[1-(amino-imino-methyl)-piperidin-4-ylmethylcarbamoyl]-2-(naphthalen-2-ylsulfonylamino)-propionyl]-benzyl-amino]-propionate hexafluorophosphate (1:1), MS (ISP): 651.6 (M+H)+;
68g) ethyl (S)-3-[[3-[1-(amino-imino-methyl)-piperidin-4-ylmethylcarbamoyl]-2-(naphthalen-2-ylsulfonylamino)-propionyl]cyclohexylmethyl-amino]-propionate hexafluorophosphate (1:1), MS (ISP): 657.5 (M+H)+;
68h) (S)-N4-[1-(amino-imino-methyl)-piperidin-4-ylmethyl]-N1-cyclopropyl-2-(naphthalen-2-ylsulfonylamino)-N1-(3-oxo-butyl) succinamide hydrochloride, MS (ISP): 571.6 (M+H)+.

EXAMPLE 69

The following acids are manufactured analogously to Example 3 from the esters of Examples 67 and 68:
a) (S)-3-[[3-[1-(Amino-imino-methyl)-piperidin-4-ylmethylcarbamoyl]-2-(naphthalen-2-ylsulfonylamino)-propionyl]cyclohexyl-amino]-acetic acid hydrochloride, MS (ISP): 601.6 (M+H)+;
b) (S)-[[3-[1-(amino-imino-methyl)-piperidin-4-ylmethylcarbamoyl]-2-(naphthalen-2-ylsulfonylamino)-propionyl]-cyclopropyl-amino]-acetic acid, MS (ISP): 559.6 (M+H)+;
c) [[(S)-3-[1-(amino-imino-methyl)-piperidin-4-ylmethylcarbamoyl]-2-(naphthalen-2-ylsulfonylamino)-propionyl]-benzylamino]acetic acid, MS (ISP): 609.5 (M+H)+;
d) (S)-[[3-[1-(amino-imino-methyl)-piperidin-4-ylmethylcarbamoyl]-2-(naphthalen-2-ylsulfonylamino)-propionyl]cyclohexylmethyl-amino]-acetic acid, MS (ISP): 615.5 (M+H)+;
e) [[(S)-3-[1-(amino-imino-methyl)-piperidin-4-ylmethylcarbamoyl]-2-(naphthalen-2-ylsulfonylamino)-propionyl]-butyl- amino]-acetic acid, MS (ISP): 575.5 (M+H)+;
f) (S)-3-[[3-[1-(amino-imino-methyl)-piperidin-4-ylmethylcarbamoyl]-2-(naphthalen-2-ylsulfonylamino)-propionyl]cyclopropyl-amino]-propionic acid hydrochloride, MS (ISP): 573.5 (M+H)+;
g) (S)-3-[[3-[1-(amino-imino-methyl)-piperidin-4-ylmethylcarbamoyl]-2-(naphthalen-2-ylsulfonylamino)-propionyl]-benzyl-amino]-propionic acid, MS (ISP): 623.6 (M+H)+;
h) (S)-3-[[3-[1-(amino-imino-methyl)-piperidin-4-ylmethylcarbamoyl]-2-(naphthalen-2-ylsulfonylamino)-propionyl]-cyclohexylmethyl-amino]-propionic acid, MS (ISP): 629.5.

EXAMPLE 70

1.0 g of N-[N4-[[(S)-1-amidino-3-piperidinyl]methyl]-N2-(2-naphthylsulfonyl)-L-asparaginyl]-N-cyclopropylglycine (Example 4a) is dissolved in 10 ml of DMF, treated with 0.2 ml of morpholine, 0.8 g of BOP and 1.1 ml of 4-ethylmorpholine and stirred at room temperature overnight. The reaction mixture is treated with 20 ml of 1N hydrochloric acid, evaporated and the residue is chromatographed on a RP-18 column with a water-acetonitrile gradient. There is obtained 0.5 g of (S)-N4-[(S)-1-(amino-imino-methyl)-piperidin-3-ylmethyl]-N1-cyclopropyl-N1-morpholin-4-ylcarbonylmethyl-2-(naphthalen-2-ylsulfonylamino)-succinamide hydrochloride (1:1), MS (ISP): 628.5 (M+H)+.

EXAMPLE 71

A solution of 0.8 g of benzyl 2-[[(S)-3-[(S)-1-(amino-imino-methyl)-piperidin-3-ylmethylcarbamoyl]-2-(naphthalen-2-ylsulfonylamino)-propionyl]-cyclopropyl-amino]-ethylcarbamate (Example 56c) in 20 ml methanol is hydrogenated at room temperature for 24 hours after the addition of 0.2 g of palladium on charcoal. The catalyst is filtered, the filtrate is evaporated and the residue is dried. 0.57 g of the thus-obtained material in 30 ml of THF is added dropwise at 0° to a solution of 0.57 g of 3,4-bis(2-propenyloxy)-3-cyclobutene-1,2-dione in 20 ml of THF and the reaction mixture is stirred at room temperature for 5 hours. The solvent is evaporated and the residue is chromatographed on silica gel with ethyl acetate-acetone-acetic acid-water (6:2:1:1). The product fractions are evaporated and there is obtained, after drying the residue, 0.6 g of (S)-N1-[2-[2-allyloxy-3,4-dioxo-cyclobut-1-enylamino)-ethyl]-N4-[(S)-1-(amino-imino-methyl)-piperidin-3-ylmethyl]-N1-cyclopropyl-2-(naphthalen-2-ylsulfonylamino)succinamide acetate (1:1), MS (ISP): 680.6 $(M+H)^+$.

EXAMPLE 72

0.1 g of the material obtained under Example 71 is dissolved in 10 ml of acetonitrile with the addition of 1 drop of water. This solution is treated with 0.03 g of palladium(II) acetate and 0.08 ml of triethyl phosphite. Subsequently, 0.13 ml of 2N sodium 2-ethyl-caproate in water is added and the reaction mixture is stirred at room temperature for 1.5 hours. The precipitated material is filtered, washed with ether-hexane and the filter residue is dried. There is isolated 0.090g of (S)-N4-[(S)-1-(amino-imino-methyl)piperidin-3-ylmethyl]-N1-cyclopropyl-N1-[2-(3,4-dioxo-2-hydroxy-cyclobut-1-enylamino)-ethyl]-2-(naphthalen-2-ylsulfonylamino)-succinamide acetate (1:1), MS (ISP): 640.5 $(M+H)^+$.

EXAMPLE 73

The following acids are prepared analogously to Example 3 from the corresponding esters:
a) from the ester of Example 49, cyclopropyl-[(S)-3-[(S)-1-(isobutoxycarbonylamino-imino-methyl)-piperidin-3-ylmethylcarbamoyl]-2-(naphthalen-2-ylsulfonylamino)-propionyl]-amino]acetic acid or the amidino group tautomer, MS (ISP): 659.5 $(M+H)^+$;
b) from the ester of Example 66, [[(S)-3-[(S)-1-(imino-tert-butoxycarbonylamino-methyl)-piperidin-3-ylmethylcarbamoyl]-2-(naphthalen-2-ylsulfonylamino)-propionyl]-cyclopropyl-amino]acetic acid or the amidino group tautomer, MS (ISP): 659.7 $(M+H)^+$.

A compound of formula I, a solvate or salt thereof can be used in a known manner as the active ingredient pharmaceutical preparations, for example, tablets and capsules of the following composition:

EXAMPLE A

|  | Per tablet |
|---|---|
| Active ingredient (1) | 200 mg |
| Microcrystalline cellulose | 155 mg |
| Corn starch | 25 mg |
| Talc | 25 mg |
| Hydroxypropylmethylcellulose | 20 mg |
|  | 425 mg |

(1) (S)-N4-[(S)-1-(amino-imino-methyl)piperidin-3-ylmethyl]-N1-carboxymethyl-N1-cyclopentyl-2-(naphthalene-2-sulfonylamino)succinamide.

EXAMPLE B

|  | Per capsule |
|---|---|
| Active ingredient (1) | 100.0 mg |
| Corn starch | 20.0 mg |
| Lactose | 95.0 mg |
| Talc | 4.5 mg |
| Magnesium stearate | 0.5 mg |
|  | 220.0 mg |

We claim:
1. A compound of the formula

$$\underset{Y}{\overset{A}{\underset{|}{\overset{O}{\underset{\parallel}{S}}}}}{\overset{O}{\underset{\parallel}{\underset{\parallel}{O}}}}-\overset{}{\underset{}{N}}-M-\overset{Q}{\underset{\parallel}{\underset{O}{C}}}-\overset{}{\underset{}{N}}-X \qquad I$$

wherein
X is a group of the formula $(X^1)$ with T, $R^1$—NH, N—$R^2$  or  $(X^2)$ with $R^{11}$—NH, N—$R^{21}$ T is $CH_2$,
$R^1$, $R^2$, $R^{11}$ and $R^{21}$ are each, independently, hydrogen or —COO-lower-alkyl,
Y is hydrogen or, when X is a group $X^2$ or when X is a group $X^1$ in which at least one of $R^1$ and $R^2$ is not hydrogen, then Y can also be —$CH_2COOH$ or —$SO_2$—A',
A and A' are aryl, alkyl or cycloalkyl,
Q is hydrogen, lower-alkyl or lower-alkyl substituted by OH, —COOH or —COO-lower alkyl,
M is a group of the formula $M^1$ or, when X is a group $X^2$ or when X is a group $X^1$ and at least one of $R^1$, $R^2$ and Q is not hydrogen and/or when A is alkyl or cycloalkyl, then M can also be a group of one of the formulae $M^2$ to $M^8$:

$(M^1)$ —CH—CH$_2$—  
        |  
        C=O  
        |  
        N—$R^4$/$R^5$  
        |  
        $R^3$ $(M^2)$ —CH—CH$_2$—  
        |  
        C=O  
        |  
        N($R^6$)

—$CH_2CH(NH(CO)_{1-2}R^7)$—  $(M^3)$,

—$CH_2CH(NHC(O)O$-benzyl)—  $(M^4)$,

=CH(CH$_2$)$_{1-2}R^7$  $(M^5)$,

=CHCH$_2$C(O)$R^8$  $(M^6)$,

=CHCH₂NH(CO)₁₋₂R⁷ (M⁷)

or

CHCH₂NHC(O)O-benzyl (M⁸),

R³ is hydrogen, lower-alkyl or -alkenyl, aryl, cycloalkyl, aryl-lower alkyl, or cycloalkyl-lower alkyl, R⁴ is hydrogen, lower-alkyl, aryl, cycloalkyl, aryl-lower alkyl or cycloalkyl-lower alkyl, R⁵ is hydrogen, lower-alkyl or a group R⁵¹ optionally bonded via lower-alkylene, R⁵¹ is —COOH, —COO-lower-alkyl, lower-alkanoyl, OH, lower-alkanoyloxy, lower-alkoxy, aryl-lower alkoxy, —CONH₂, —CONHCH₂CH₂OH, —CONHOH, —CONHOCH₃, —CONHO-benzyl, —CONHSO₂-lower-alkyl, —CONHCH₂CH₂-aryl, —CONH-cycloalkyl, NH₂, —NHCOO-lower-alkyl, —NHCOO-lower-aralkyl, —NHSO₃H, (—NHSO₂ or —NHSO₃)-lower-alkyl, —NH-lower-alkanoyl, —NHCOCOOH, —NHCOCOO-lower-alkyl, -NH-cycloalkyl, —NH—(3,4-dioxo-2-hydroxy-cyclobut-1-enyl), —NH—, —NHCOCO-(aryl or lower-alkyl), —NHCOCH₂Cl, —NHCOCH₂O-aryl, —NHCOCH₂-aryl, —NHCO-aryl, —NHPO₃(R⁹,R¹⁰), R⁹ and R¹⁰ are hydrogen, lower-alkyl or phenyl, provided that R⁴ can not be phenyl, when Q, R¹, R², R³ and R⁵ are simultaneously hydrogen, N(R⁶) is benzylamino, R⁷ and R⁸ are aryl, or cycloalkyl a hydrate, solvate or physiologically compatible salt thereof.

2. A compound in accordance with claim 1, selected from the group consisting of:

3-[[(S)-3-[(S)-1-(Amino-imino-methyl)-piperidin-3-ylcarbamoyl]-2-(4-carbamoyl-phenylsulfonylamino)-propionyl]-cyclopropyl-amino]propionic acid, and (S)-N4-[(S)-1-(amino-imino-methyl)-piperidin-3-ylmethyl]-N1-cyclopropyl-N1-[2-(3,4-dihydroxy-phenyl)-ethylcarbamoyl-methyl]-2-(naphthalen-2-ylsulfonylamino)-succinamide.

3. A compound in accordance with claim 1, selected from the group consisting of:

2-[(S)-2-[(S)-1-Amino-imino-methyl)-piperidin-3-ylmethylcarbamoyl]-1-[cyclopropyl-(2-ethoxycarbonyl-ethyl)-carbamoyl]ethylsulfamoyl]-benzoic acid, 3-[[(S)-3-[(S)-1-(amino-imino-methyl)-piperidin-3-ylcarbamoyl]-2-(4-cyano-phenylsulfonylamino)-propionyl]-cyclopropyl-amino]-propionic acid, 2-[[(S)-3-[(S)-1-(amino-imino-methyl)-piperidin-3-ylmethylcarbamoyl]-2-(naphthalen-2-ylsulfonylamino)-propionyl]-cyclopropylamino]-ethylsulfamic acid, (S)-N4-[(S)-1-(amino-imino-methyl)-piperidin-3-ylmethyl]-N1-(2-chloroacetylamino-ethyl)-N1-cyclopropyl-2-(naphthalen-2-ylsulfonylamino)-succinamide, (S)-N4-[(S)-1-(amino-imino-methyl)-piperidin-3-ylmethyl]-N1cyclopropyl-2-(naphthalen-2-ylsulfonylamino)-N1-(2-phenoxyacetylamino-ethyl)-succinamide, (S)-N4-[(S)-1-(amino-imino-methyl)-piperidin-3-ylmethyl]-N1-cyclopropyl-2-(naphthalen-2-ylsulfonylamino)-N1-[2-(2-oxo-2-phenylacetylamino)-ethyl]-succinamide, and (S)-N4-[(S)-1-(amino-imino-methyl)-piperidin-3-ylmethyl]-N1-cyclopropyl-2-(naphthalen-2-ylsulfonylamino)-N1-[2-(2-oxopropionylamino)-ethyl]-succinamide.

4. A pharmaceutical composition comprising an effective amount of a compound of the formula

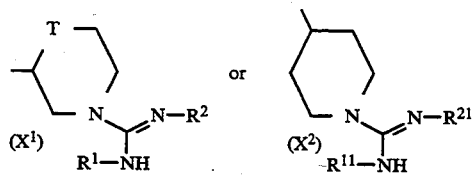 I wherein

X is a group of the formula

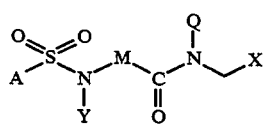

T is CH₂,

R¹, R², R¹¹ and R²¹ are each, independently, hydrogen or —COO-lower-alkyl,

Y is hydrogen or, when X is a group X² or when X is a group X¹ in which at least one of R¹ and R² is not hydrogen, then Y can also be —CH₂COOH or —SO₂—A′, A and A′ are aryl, alkyl or cycloalkyl, Q is hydrogen, lower-alkyl or lower-alkyl substituted by OH, —COOH or —COO-lower alkyl, M is a group of the formula M¹ or, when X is a group X² or when X is a group X¹ and at least one of R¹, R² and Q is not hydrogen and/or when A is alkyl or cycloalkyl, then M can also be a group of one of the formulae M² to M⁸:

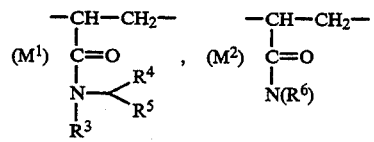

—CH₂CH(NH(CO)₁₋₂R⁷)— (M³),

—CH₂CH(NHC(O)O-benzyl)— (M⁴),

=CH(CH₂)₁₋₂R⁷ (M⁵),

=CHCH₂C(O)R⁸ (M⁶),

=CHCH₂NH(CO)₁₋₂R⁷ (M⁷)

or

=CHCH₂NHC(O)O-benzyl (M⁸),

R³ is hydrogen, lower-alkyl or -alkenyl, aryl, cycloalkyl, aryl-lower alkyl, or cycloalkyl-lower alkyl, R⁴ is hydrogen, lower-alkyl, aryl, cycloalkyl, aryl-lower alkyl or cycloalkyl-lower alkyl, $R^5$ is hydrogen, lower-alkyl or a group $R^{51}$ optionally bonded via lower-alkylene, $R^{51}$ is —COOH, —COO-lower-alkyl, lower-alkanoyl, OH, lower-alkanoyloxy, lower-alkoxy, aryllower alkoxy, —CONH$_2$, —CONHCH$_2$CH$_2$OH, —CONHOH, —CONHCH$_3$, —CONHO-benzyl, —CONHSO$_2$-lower-alkyl, —CONHCH$_2$CH$_2$-aryl, —CONH-cycloalkyl, NH$_2$, —NHCOO-lower-alkyl, —NHCOO-lower-aralkyl, —NHSO$_3$H, (—NHSO$_2$ or —NHSO$_3$)-lower-alkyl, —NH-lower-alkanoyl, —NHCOCOOH, —NHCOCOO-lower-alkyl, —NH-cycloalkyl, —NH—(3,4-dioxo-2-hydroxy-cyclobut-1-enyl), —NH—[2-lower(alkoxy or -alkenyloxy)-3,4-dioxocyclobut-1-enyl], —NHCOCO-(aryl or lower-alkyl), —NHCOCH$_2$CH, —NHCOCH$_2$O-aryl, —NHCOCH$_2$-aryl, —NHCO-aryl, —NHPO$_3$(R$^9$,R$^{10}$), $R^9$ and $R^{10}$ are hydrogen, lower-alkyl or phenyl, provided that $R^4$ can not be phenyl, when Q, $R^1$, $R^2$, $R^3$ and $R^5$ are simultaneously hydrogen, N($R^6$) is benzylamino, $R^7$ and $R^8$ are aryl, or cycloalkyl, a hydrate, solvate or physiologically compatible salt thereof, and an inert carrier.

5. A pharmaceutical composition in accordance with claim 4, wherein the compound of formula I is selected from the group consisting of:

3-[[(S)-3-[(S)-1-(Amino-imino-methyl)-piperidin-3-ylcarbamoyl]-2-(4-carbamoyl-phenylsulfonylamino)-propionyl]-cyclopropyl-amino]propionic acid, and (S)-N 4-[(S)-1-(amino-imino-methyl)-piperidin-3-ylmethyl]-N1-cyclopropyl-N1-[2-(3,4-dihydroxyphenyl)-ethylcarbamoyl-methyl]-2-(naphthalen-2-ylsulfonylamino)-succinamide.

6. A pharmaceutical composition in accordance with claim 4, wherein the compound of formula I is selected from the group consisting of:

2-[(S)-2-[(S)-1-Amino-imino-methyl)-piperidin-3-ylmethylcarbamoyl]-1-[cyclopropyl-(2-ethoxycarbonyl-ethyl)-carbamoyl]ethylsulfamoyl]-benzoic acid, 3-[[(S)-3-[(S)-1-(amino-imino-methyl)-piperidin-3-ylcarbamoyl]-2-(4-cyano-phenylsulfonylamino)-propionyl]-cyclopropyl-amino]-propionic acid, 2-[[(S)-3-[(S)-1-(amino-imino-methyl)-piperidin-3-ylmethylcarbamoyl]-2-(naphthalen-2-ylsulfonylamino)-propionyl]-cyclopropylamino]-ethylsulfamic acid, (S)-N4-[(S)-1-(amino-imino-methyl)-piperidin-3-ylmethyl]-N1-(2-chloroacetylamino-ethyl)-N1-cyclopropyl-2-(naphthalen-2-ylsulfonylamino)-succinamide, (S)-N4-[(S)-1-(amino-imino-methyl)-piperidin-3-ylmethyl]-N1-cyclopropyl-2-(naphthalen-2-ylsulfonylamino)-N1-(2-phenoxyacetylamino-ethyl)-succinamide, (S)-N4-[(S)-1-(amino-imino-methyl)-piperidin-3-ylmethyl]-N1-cyclopropyl-2-(naphthalen-2-ylsulfonylamino)-N1-[2-(2-oxo-2-phenylacetylamino)-ethyl]-succinamide, and (S)-N4-[(S)-1-(amino-imino-methyl)-piperidin-3-ylmethyl]-N1-cyclopropyl-2-(naphthalen-2-ylsulfonylamino)-N1-[2-(2-oxopropionylamino)-ethyl]-succinamide.

7. A method of inhibiting thrombin-induced platelet aggregation and clotting of fibrinogen in a host requiring such treatment which comprises administering an effective amount of a compound of the formula

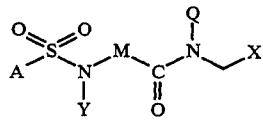

wherein

X is a group of the formula

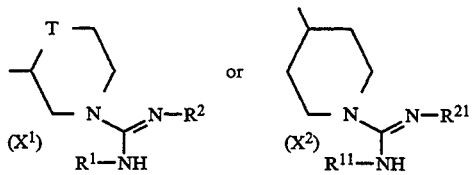

T is CH$_2$, $R^1$, $R^2$, $R^{11}$ and $R^{21}$ are each, independently, hydrogen or —COO-lower-alkyl, Y is hydrogen or, when X is a group $X^2$ or when X is a group $X^1$ in which at least one of $R^1$ and $R^2$ is not hydrogen, then Y can also be —CH$_2$COOH or —SO$_2$—A', A and A' are aryl, alkyl or cycloalkyl, Q is hydrogen, lower-alkyl or lower-alkyl substituted by OH, —COOH or —COO-lower alkyl, M is a group of the formula $M^1$ or, when X is a group $X^2$ or when X is a group $X^1$ and at least one of $R^1$, $R^2$ and Q is not hydrogen and/or when A is alkyl or cycloalkyl, then M can also be a group of one of the formulae $M^2$ to $M^8$:

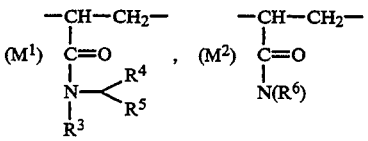

| | |
|---|---|
| —CH$_2$CH(NH(CO)$_{1-2}$R$^7$)— | (M$^3$), |
| —CH$_2$CH(NHC(O)O-benzyl)— | (M$^4$), |
| =CH(CH$_2$)$_{1-2}$R$^7$ | (M$^5$), |
| =CHCH$_2$C(O)R$^8$ | (M$^6$), |
| =CHCH$_2$NH(CO)$_{1-2}$R$^7$ | (M$^7$) | or

| | |
|---|---|
| =CHCH$_2$NHC(O)O-benzyl | (M$^8$), |

$R^3$ is hydrogen, lower-alkyl or -alkenyl, aryl, cycloalkyl, aryl-lower alkyl, or cycloalkyl-lower alkyl, $R^4$ is hydrogen, lower-alkyl, aryl, cycloalkyl, aryllower alkyl or cycloalkyl-lower alkyl, $R^5$ is hydrogen, lower-alkyl or a group $R^{51}$ optionally bonded via lower-alkylene, $R^{51}$ is —COOH, —COO-lower-alkyl, lower-alkanoyl, OH, lower-alkanoyloxy, lower-alkoxy, aryllower alkoxy, —CONH$_2$, —CONHCH$_2$CH$_2$OH, —CONHOH, —CONHOCH$_3$, —CONHO-benzyl, —CONHSO$_2$-lower-alkyl, —CONHCH$_2$CH$_2$-aryl, —CONH-cycloalkyl, NH$_2$, —NHCOO-lower-alkyl, —NHCOO-lower-aralkyl, —NHSO$_3$H, (—NHSO$_2$ or —NHSO$_3$)-lower-alkyl, —NH-lower-alkanoyl, —NHCOCOOH, —NHCOCOO-lower-alkyl, —NH-cycloalkyl, —NH—(3,4-dioxo-2-hydroxy-cyclobut-1-enyl), —NH-[2-lower(alkoxy or -alkenyloxy)-3,4-dioxocyclobut-1-enyl], —NHCOCO-(aryl or lower-alkyl), —NHCOCH$_2$Cl, —NHCOCH$_2$O-aryl, —NHCOCH$_2$-aryl, —NH-CO-aryl, —NHPO$_3$(R$^9$,R$^{10}$), R$^9$ and R$^{10}$ are hydrogen, lower-alkyl or phenyl, provided that R$^4$ can not be phenyl, when Q, R$^1$, R$^2$, R$^3$ and R$^5$ are simultaneously hydrogen, N(R$^6$) is benzylamino, R$^7$ and R$^8$ are aryl, or cycloalkyl, a hydrate, solvate or physiologically compatible salt thereof.

8. A method in accordance with claim 7, wherein the compound of formula I is selected from the group consisting of:
   3-[[(S)-3-[(S)-1 -(Amino-imino-methyl)-piperidin-3-ylcarbamoyl]-2-(4-carbamoyl-phenylsulfonylamino)-propionyl]-cyclopropyl-amino]propionic acid,
   (S)-N4-[(S)-1-(amino-imino-methyl)-piperidin-3-ylmethyl]-N1-cyclopropyl-N1-[2-(3,4-dihydroxy-phenyl)-ethylcarbamoyl-methyl]-2-(naphthalen-2-ylsulfonylamino)-succinamide.

9. A method in accordance with claim 7, wherein the compound of formula I is selected from the group consisting of:
   2-[(S)-2-[(S)-1-Amino-imino-methyl)-piperidin-3-ylmethylcarbamoyl]-1-[cyclopropyl-(2-ethoxycarbonyl-ethyl)-carbamoyl]ethylsulfamoyl]-benzoic acid,
   3-[[(S)-3-[(S)-1-(amino-imino-methyl)-piperidin-3-ylcarbamoyl]-2-(4-cyano-phenylsulfonylamino)-propionyl]-cyclopropyl-amino]-propionic acid,
   2-[[(S)-3-[(S)-1-(amino-imino-methyl)-piperidin-3-ylmethylcarbamoyl]-2-(naphthalen-2-ylsulfonylamino)-propionyl]-cyclopropylamino]-ethylsulfamic acid,
   (S)-N4-[(S)-1-(amino-imino-methyl)-piperidin-3-ylmethyl]-N1-(2-chloroacetylamino-ethyl)-N1-cyclopropyl-2-(naphthalen-2-ylsulfonylamino)-succinamide,
   (S)-N4-[(S)-1-(amino-imino-methyl)-piperidin-3-ylmethyl]-N1-cyclopropyl-2-(naphthalen-2-ylsulfonylamino)-N1-(2-phenoxyacetylamino-ethyl)-succinamide,
   (S)-N4-[(S)-1-(amino-imino-methyl)-piperidin-3-ylmethyl]-N1-cyclopropyl-2-(naphthalen-2-ylsulfonylamino)-N1-[2-(2-oxo-2-phenylacetylamino)-ethyl]-succinamide, and
   (S)-N4-[(S)-1-(amino-imino-methyl)-piperidin-3-ylmeth yl]-N1-cyclopropyl-2-(naphthalen-2-ylsulfonylamino)-N1-[2-(2-oxopropionylamino)-ethyl]-succinamide.

10. A compound in accordance with claim 1, wherein X is a group X$^1$ in which the guanidino group is unprotected,
Y is hydrogen,
A is aryl,
Q has the same significance as in claim 1 and
M is either the group M$^1$ in which R$^3$ and R$^4$ have the same significance as in claim 1, with the proviso that R$^4$ must not be hydrogen or phenyl, when Q, R$^3$ and R$^5$ are simultaneously hydrogen, and R$^5$ is hydrogen, lower-alkyl or a group R$^{52}$ optionally bonded via lower-alkylene,
R$^{52}$ is —COOH, COO-lower-alkyl, lower-alkanoyl, OH, lower-alkanoyloxy, —NH$_2$, —NHCOO-lower-alkyl, —NHSO$_3$H, (—NHSO$_2$ or —NHSO$_3$)-lower-alkyl, —NH-lower-alkanoyl, —NHCOCOOH, —NHCOCOO-lower-alkyl or NHPO$_3$(R$^9$,R$^{10}$).

11. A compound in accordance with claim 1, wherein Y is hydrogen, X is the group X$^1$ and M is the group M$^1$ and, where at least one of R$^1$ and R$^2$, in X$^1$, is not hydrogen and/or where Q is not hydrogen and/or where A is alkyl or cycloalkyl, then M can also be a group M$^2$.

12. A compound in accordance with claim 1, wherein Y is hydrogen, X is the group X$^2$ and M is the group M$^1$ or M$^2$.

13. A compound in accordance with claim 1, wherein Y is hydrogen, X is the X$^1$ and M is the group M$^5$ or M$^6$, with the proviso that at least one of R$^1$ and R$^2$, in group X$^1$, is not hydrogen and/or that Q is not hydrogen and/or that A is alkyl or cycloalkyl.

14. A compound in accordance with claim 1, wherein Y is hydrogen, X is the group X$^1$ and M is the group M$^3$ or M$^7$, with the proviso that at least one of R$^1$ and R$^2$, in X$^1$, is not hydrogen and/or that Q is not hydrogen and/or that A is alkyl or cycloalkyl.

15. A compound in accordance with claim 11, wherein Y and Q are hydrogen, X is the group X$^1$ and M is the group M$^1$ and, wherein at least one of R$^1$ and R$^2$, in X$^1$, is not hydrogen and/or where A is alkyl or cycloalkyl, then M can also be a group M$^2$.

16. A compound in accordance with claim 11, wherein Y is hydrogen, Q is unsubstituted lower-alkyl or substituted by OH, —COOH or —COO-lower alkyl, X is the group X$^1$ and M is the group M$^1$ or M$^2$.

17. A compound in accordance with claim 1, wherein A is naphthyl, or phenyl substituted by t-butyl, CF$_3$, phenyl, cyclopentyl, carboxy, methoxycarbonyl, ethoxycarbonyl, OCF$_3$, CN, or CONH$_2$.

18. A compound in accordance with claim 1, wherein Q is hydrogen, CH$_3$, —CH$_2$COOH, —CH$_2$CH$_2$OH or —CH$_2$COOC$_2$H$_5$.

19. A compound in accordance with claim 1, wherein X is the group X$^1$, T is CH$_2$, one of R$^1$ and R$^2$ is hydrogen and the other is hydrogen or —COO-methyl, —COO-ethyl, —COO-isobutyl or —COO-t-butyl.

20. A compound in accordance with claim 1, wherein X is the group X$^2$ and R$^{11}$ and R$^{21}$ are hydrogen.

21. A compound in accordance with claim 1, wherein M is the group M$^1$, R$^3$ is hydrogen, CH$_3$, propyl, isopropyl, butyl, pentyl, allyl, cyclopropyl, cyclopentyl, cyclohexyl, cyclopropylmethyl, cyclohexylmethyl, or benzyl, unsubstituted or substituted by chlorine or methoxy and R$^4$ is hydrogen, isopropyl, 2-butyl, isobutyl, phenyl, benzyl or cyclohexyl.

22. A compound in accordance with claim 1, wherein R$^5$ is the group (CH$_2$)$_{0-2}$—R$^{50}$ and R$^{50}$ is hydrogen, OH, —C(CH$_3$)$_2$OH, —COCH$_3$, —OCOCH$_3$, —COOH, —COOCH$_3$, —COOC$_2$H$_5$, —NHCOOCH$_3$, —NHCOCH$_3$, —CONH$_2$, —OCH$_3$, benzyloxy, —CONHOCH$_3$, —CONHO-benzyl, —CONHSO$_2$CH$_3$, —CONH-cyclopropyl, —CONHCH$_2$CH$_2$—C$_6$H$_3$(OH)$_2$, —CONHCH$_2$CH$_2$OH, —NHCOCOOH, —NHCOCOOCH$_3$, —NHCOCOOC$_2$H$_5$, —NHSO$_3$H, —NHSO$_2$CH$_3$, —NHCOO-benzyl, —NHCOCH$_2$Cl, —NHCOCH$_2$OC$_6$H$_5$, —NHCOCOC$_6$H$_5$, —NHCOCOCH$_3$, —NHCOCH$_2$C$_6$H$_3$(OH)$_2$, —NH- PO(OC$_6$H$_5$)$_2$, —NHPO(OC$_2$H$_5$)$_2$, —NH-(3,4-dioxo-2-hydroxycyclobut-1-enyl) or —NH-(2-allyloxy-3,4-dioxocyclobut-1-enyl).

23. A compound in accordance with claim 1, selected from the group consisting of:
   N-[N 4-[[(S)-1-Amidino-3-piperidinyl]methyl]-N2-(2-naphthylsulfonyl)-L-asparaginyl]-N-cyclopropylglycine,
   (S)-[[3-[(S)-1-(amino-imino-methyl)piperidin-3-ylmethylcarbamoyl]-2-(naphthalene-2-sulfonylamino)-propionyl]cyclopropylamino]propionic acid, and
   [(S)-3-[(S)-1-(amino-imino-methyl)piperidin-3-ylmethylcarbamoyl]-2-(4-trifluoromethyl-phenylsulfonylamino)-propionyl- cyclopropyl-amino]acetic acid.

24. A compound in accordance with claim 1, selected from the group consisting of:
   (S)-N4-[(S)-1-(Amino-imino-methyl)piperidin-3-ylmethyl]-N1-carboxymethyl-N1-cyclopentyl-2-(naphthalene-2-sulfonylamino) succinamide,
   [(S)-3-[(S)-2-(amino-imino-methyl)piperidin-3-ylmethylcarbamoyl]-2-(naphthalene-2-sulfonylamino)-propionyl]-propylaminoacetic acid,
   N-[N4-[[(S)-1-amidino-3-piperidinyl]methyl]-N2-(2naphthylsulfonyl)-L-asparaginyl]-N-(o-chlorobenzyl)glycine,
   [2-[[(S)-3-[(S)-1-(amino-imino-methyl)piperidin-3-ylmethylcarbamoyl]-2-(naphthalene-2-sulfonylamino)-propionyl]butyl-amino]ethyl]oxamic acid,
   (S)-N4-[(S)-1-(amino-imino-methyl)piperidin-3-ylmethyl]-N1-butyl-2-(naphthalene-2-sulfonylamino)-N1-(2-sulfoamino-ethyl)succinamide, and
   [(S)-3-[(S)-1-(amino-imino-methyl)piperidin-3-ylmethylcarbamoyl]-2-(4-t-butylphenylsulfonylamino)-propionyl-cyclopropyl-amino]-acetic acid.

25. A pharmaceutical composition, in accordance with claim 4, wherein
   X is a group X$^1$ in which the guanidino group is unprotected,
   Y is hydrogen,
   A is aryl,
   Q has the same significance as in claim 4 and
   M is either the group M$^1$ in which R$^3$ and R$^4$ have the same significance as in claim 4, with the proviso that R$^4$ must not be hydrogen or phenyl, when Q, R$^3$ and R$^5$ are simultaneously hydrogen, and
   R$^5$ is hydrogen, lower-alkyl or a group R$^{52}$ optionally bonded via lower-alkylene,
   R$^{52}$ is —COOH, —COO-lower-alkyl, lower-alkanoyl, OH, lower-alkanoyloxy, —NH$_2$, —NHCOO-lower-alkyl, —NHSO$_3$H, (—NHSO$_2$ or —NHSO$_3$)-lower-alkyl, —NH-lower-alkanoyl, -NHCOCOOH, —NHCOCOO-lower-alkyl or —NH-PO$_3$(R$^9$,R$^{10}$).

26. A pharmaceutical composition, in accordance with claim 4, wherein Y is hydrogen, X is the group X$^1$ and M is the group M$^1$ and, where at least one of R$^1$ and R$^2$, in X$^1$, is not hydrogen and/or where Q is not hydrogen and/or where A is alkyl or cycloalkyl, then M can also be a group M$^2$.

27. A pharmaceutical composition, in accordance with claim 4, wherein Y is hydrogen, X is the group X$^2$ and M is the group M$^1$ or M$^2$.

28. A pharmaceutical composition, in accordance with claim 4, wherein R$^5$ is the group (CH$_2$)$_{0-2}$—R$^{50}$ and R$^{50}$ is hydrogen, OH, —C(CH$_3$)$_2$OH, —COCH$_3$, OCOCH$_3$, —COOH, —COOCH$_3$, —COOC$_2$H$_5$, —NHCOOCH$_3$, —NHCOCH$_3$, —CONH$_2$, —OCH$_3$, benzyloxy, —CONHOCH$_3$, —CONHO-benzyl, —CONHSO$_2$CH$_3$, —CONH-cyclopropyl, —CONHCH$_2$CH$_2$—C$_6$H$_3$(OH)$_2$, —CONHCH$_2$CH$_2$OH, —NHCOCOOH, —NHCOCOOCH$_3$, —NHCOCOOC$_2$H$_5$, —NHSO$_3$H, —NHSO$_2$CH$_3$, —NHCOO-benzyl, —NHCOCH$_2$Cl, —NHCOCH$_2$OC$_6$H$_5$, —NHCOCOC$_6$H$_5$, —NHCOCOCH$_3$, —NHCOCH$_2$C$_6$H$_3$(OH)$_2$, —NHPO(OC$_6$H$_5$)$_2$, —NHPO(OC$_2$H$_5$)$_2$, —NH—(3,4-dioxo-2-hydroxycyclobut-1-enyl) or —NH—(2-allyloxy-3,4-dioxocyclobut-1-enyl).

29. A pharmaceutical composition in accordance with claim 4, wherein the compound of formula I is selected from the group consisting of:
   N-[N4-[[(S)-1-Amidino-3-piperidinyl]methyl]-N2-(2-naphthylsulfonyl)-L-asparaginyl]-N-cyclopropylglycine,
   (S)-[[3-[(S)-1-(amino-imino-methyl)piperidin-3-ylmethylcarbamoyl]-2-(naphthalene-2-sulfonylamino)-propionyl]cyclopropylamino]propionic acid, and
   [(S)-3-[(S)-1-(amino-imino-methyl)piperidin-3-ylmethylcarbamoyl]-2-(4-trifluoromethyl-phenylsulfonylamino)-propionyl-cyclopropyl-amino]acetic acid.

30. A pharmaceutical composition in accordance with claim 4, wherein the compound of formula I is selected from the group consisting of:
   (S)-N4-[(S)-1-(Amino-imino-methyl)piperidin-3-ylmethyl]-N1-carboxymethyl-N1-cyclopentyl-2-(naphthalene-2-sulfonylamino) succinamide,
   [(S)-3-[(S)-2-(amino-imino-methyl)piperidin-3-ylmethylcarbamoyl]-2-(naphthalene-2-sulfonylamino)-propionyl]-propylaminoacetic acid,
   N-[N4-[[(S)-1-amidino-3-piperidinyl]methyl]-N2-(2-naphthylsulfonyl)-L-asparaginyl]-N-(o-chlorobenzyl)glycine,
   [2-[[(S)-3-[(S)-1-(amino-imino-methyl)piperidin-3-ylmethylcarbamoyl]-2-(naphthalene-2-sulfonylamino)-propionyl]butyl-amino]ethyl]oxamic acid,
   (S)-N4-[(S)-1-(amino-imino-methyl)piperidin-3-ylmethyl]-N1-butyl-2-(naphthalene-2-sulfonylamino)-N1-(2-sulfoamino-ethyl)succinamide, and
   [(S)-3-[(S)-1-(amino-imino-methyl)piperidin-3-ylmethylcarbamoyl]-2-(4-t-butylphenylsulfonylamino)-propionyl-cyclo-propyl-amino]-acetic acid.

31. A method in accordance with claim 7, wherein
   X is a group X$^1$ in which the guanidino group is unprotected,
   Y is hydrogen,
   A is aryl,
   Q has the same significance as in claim 1 and
   M is either the group M$^1$ in which R$^3$ and R$^4$ have the same significance as in claim 1, with the proviso that R$^4$ must not be hydrogen or phenyl, when Q, R$^3$ and R$^5$ are simultaneously hydrogen, and
   R$^5$ is hydrogen, lower-alkyl or a group R$^{52}$ optionally bonded via alkylene,
   R$^{52}$is —COOH, —COO-lower-alkyl, lower-alkanoyl, OH, lower-alkanoyloxy, —NH$_2$, —NHCOO-lower-alkyl, —NHSO$_3$H, (—NHSO$_2$ or —NHSO$_3$)-lower-alkyl, —NH-lower-alkanoyl, —NHCOCOOH, —NHCOCOO-lower-alkyl or —NHPO$_3$(R$^9$,R$^{10}$).

32. A method in accordance with claim 7, wherein Y is hydrogen, X is the group X$^1$ and M is the group M$^1$ and, where at least one of R$^1$ and R$^2$, in X$^1$, is not hydrogen and/or where Q is not hydrogen and/or where A is alkyl or cycloalkyl, then M can also be a group $M^2$.

33. A method in accordance with claim 7, wherein Y is hydrogen, X is the group $X^2$ and M is the group $M^1$ or $M^2$.

34. A method in accordance with claim 7, wherein $R^5$ is the group $(CH_2)_{0-2}$—$R^{50}$ and $R^{50}$ is hydrogen, OH, —$C(CH_3)_2OH$, —$COCH_3$, —$OCOCH_3$, —COOH, —$COOCH_3$, —$COOC_2H_5$, —$NHCOOCH_3$, -$NHCOCH_3$, —$CONH_2$, —$OCH_3$, benzyloxy, —$CONHOCH_3$, —CONHO-benzyl, —$CONHSO_2CH_3$, —CONH-cyclopropyl, —$CONHCH_2CH_2$—$C_6H_3(OH)_2$, —$CONHCH_2CH_2OH$, —NHCOCOOH, —$NHCOCOOCH_3$, —$NHCOCOOC_2H_5$, —$NHSO_3H$, —$NHSO_2CH_3$, —NHCOO-benzyl, —$NHCOCH_2Cl$, —$NHCOCH_2OC_6H_5$, —$NHCOCOC_6H_5$, —$NHCOCOCH_3$, —$NHCOCH_2C_6H_3(OH)_2$, —$NHPO(OC_6H_5)_2$, —$NHPO(OC_2H_5)_2$, —NH—(3,4-dioxo-2-hydroxycyclobut-1-enyl) or —NH—(2-allyloxy-3,4-dioxocyclobut-1-enyl).

35. A method in accordance with claim 7, wherein the compound of formula I is selected from the group consisting of:

N-[N4-[[(S)-1-Amidino-3-piperidinyl]methyl]-N2-(2-naphthylsulfonyl)-L-asparaginyl]-N-cyclopropylglycine, (S)-[[3-[(S)-1-(amino-imino-methyl)piperidin-3-ylmethylcarbamoyl]-2-(naphthalene-2-sulfonylamino)-propionyl]cyclopropylamino]propionic acid, and

[(S)-3-[(S)-1-(amino-imino-methyl)piperidin-3-ylmethylcarbamoyl]-2-(4-trifluoromethyl-phenylsulfonylamino )-propionyl-cyclopropyl-amino]acetic acid.

36. A method in accordance with claim 7, wherein the compound of formula I is selected from the group consisting of:

(S)-N4-[(S)-1-(Amino-imino-methyl)piperidin-3-ylmethyl]-N1-carboxymethyl-N1-cyclopentyl-2-(naphthalene-2-sulfonylamino) succinamide,

[(S)-3-[(S)-2-(amino-imino-methyl)piperidin-3-ylmethylcarbamoyl]-2-(naphthalene-2-sulfonylamino)-propionyl]-propylaminoacetic acid, N-[N4-[[(S)-1-amidino-3-piperidinyl]methyl]-N2-(2-naphthylsulfonyl)-L-asparaginyl]-N-(o-chlorobenzyl)glycine,

[2-[[(S)-3-[(S)-1-(amino-imino-methyl)piperidin-3-ylmethylcarbamoyl]-2-(naphthalene-2-sulfonylamino)-propionyl]butyl-amino]ethyl]oxamic acid, (S)-N4-[(S)-1-(amino-imino-methyl)piperidin-3-ylmethyl]-N1-butyl-2-(naphthalene-2-sulfonylamino)-N1-(2-sulfoamino-ethyl)succinamide, and

[(S)-3-[(S)-1-(amino-imino-methyl)piperidin-3-ylmethylcarbamoyl]-2-(4-t-butylphenylsulfonylamino )-propionyl-cyclopropyl-amino]-acetic acid.

* * * * *